(12) United States Patent
Noe

(10) Patent No.: US 6,608,104 B2
(45) Date of Patent: Aug. 19, 2003

(54) GEM SUBSTITUTED HYDROXAMIC ACIDS

(75) Inventor: Mark C. Noe, Mystic, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/818,056

(22) Filed: Mar. 27, 2001

(65) Prior Publication Data

US 2002/0019534 A1 Feb. 14, 2002

Related U.S. Application Data

(60) Provisional application No. 60/192,963, filed on Mar. 29, 2000.

(51) Int. Cl.[7] ................................................ A61K 31/35
(52) U.S. Cl. ........................................ 514/459; 549/417
(58) Field of Search ........................... 549/417; 514/459

(56) References Cited

U.S. PATENT DOCUMENTS

| 5,753,653 A | 5/1998 | Bender et al. ........... 514/227.5 |
| 5,861,510 A | 1/1999 | Piscopio et al. ............ 544/131 |

FOREIGN PATENT DOCUMENTS

| EP | 606046 | 7/1994 | ......... C07D/213/42 |
| WO | 9808815 | 3/1998 | ......... C07D/207/48 |
| WO | 9808825 | 3/1998 | ......... C07D/241/04 |
| WO | 9834918 | 8/1998 | ......... C07D/211/62 |
| WO | 9958531 | 11/1999 | ......... C07D/417/12 |

*Primary Examiner*—Amelia Owens
(74) *Attorney, Agent, or Firm*—Peter C. Richardson; Paul H. Ginsburg; Krishna G. Banerjee

(57) ABSTRACT

A compound of the formula

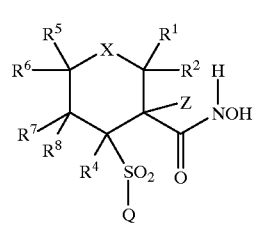

I wherein $R^1$–$R^{13}$, X, Z and Q are as defined above, useful in the treatment of arthritis, cancer, and other diseases involving the dysregulated production/release of reprolysins such as Aggrecanase and other diseases characterized by matrix metalloproteinase activity. In addition, the compounds of the present invention may be used in combination therapy with standard non-steroidal anti-inflammatory drugs (NSAID's), COX-2 inhibitors and analgesics, and in combination with cytotoxic drugs such as adriamycin, daunomycin, cis-platinum, etoposide, taxol, taxotere and other alkaloids, such as vincristine, in the treatment of cancer.

28 Claims, No Drawings

GEM SUBSTITUTED HYDROXAMIC ACIDS

The present application is a United States Non-Provisional Application which claims priority from U.S. Provisional Application No. 60/192,963, filed Mar. 29, 2000.

BACKGROUND OF THE INVENTION

The present invention relates to geminal disubstituted cyclic hydroxamic acids and derivatives thereof, and to pharmaceutical compositions comprising such derivatives and to the use of such derivatives in the treatment of arthritis, cancer and other diseases. The present invention also relates to treating arthritis in a mammal, comprising administering to such mammal an effective amount of an inhibitor with potent or differential MMP or reprolysin activity (preferably wherein said inhibitor is selective for Aggrecanase over MMP-1, or MMP-13 and/or Aggrecanase over MMP-1).

The compounds of the present invention are inhibitors of zinc metalloendopeptidases, especially those belonging to the matrix metalloproteinase (also called MMP or matrixin) and reprolysin (also known as adamylsin) subfamilies of the metzincins (Rawlings, et al., Methods in Enzymology, 248, 183–228 (1995) and Stocker, et al., Protein Science, 4, 823–840 (1995)).

The MMP subfamily of enzymes currently contains seventeen members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMP's are most well known for their role in regulating the turn-over of extracellular matrix proteins and as such play important roles in normal physiological processes such as reproduction, development and differentiation. In addition, the MMP's are expressed in many pathological situations in which abnormal connective tissue turnover is occurring. For example, MMP-13 an enzyme with potent activity at degrading type II collagen (the principal collagen in cartilage), has been demonstrated to be overexpressed in osteoarthritic cartilage (Mitchell, et al., J. Clin. Invest., 97, 761 (1996)). Other MMPs (MMP-2, MMP-3, MMP-8, MMP-9, MMP-12) are also overexpressed in osteoarthritic cartilage and inhibition of some or all of these MMP's is expected to slow or block the accelerated loss of cartilage typical of joint diseases such as osteoarthritis or rheumatoid arthritis.

The mammalian reprolysins are known as ADAMs (A Disintegrin And Metalloproteinase) (Wolfberg, et al., J. Cell Biol., 131, 275–278 (1995)) and contain a disintegrin domain in addition to a metalloproteinase-like domain. To date twenty-three distinct ADAM's have been identified.

ADAM-17, also known as tumor necrosis factor-alpha converting enzyme (TACE), is the most well known ADAM. ADAM-17 (TACE) is responsible for cleavage of cell bound tumor necrosis factor-alpha (TNF-α, also known as cachectin). TNF-α is recognized to be involved in many infectious and autoimmune diseases (W. Friers, FEBS Letters, 285, 199 (1991)). Furthermore, it has been shown that TNF-α is the prime mediator of the inflammatory response seen in sepsis and septic shock (Spooner, et al., Clinical Immunology and Immunopathology, 62 S11 (1992)). There are two forms of TNF-α, a type II membrane protein of relative molecular mass 26,000 (26 kD) and a soluble 17 kD form generated from the cell bound protein by specific proteolytic cleavage. The soluble 17 kD form of TNF-α is released by the cell and is associated with the deleterious effects of TNF-α. This form of TNF-α is also capable of acting at sites distant from the site of synthesis. Thus, inhibitors of TACE prevent the formation of soluble TNF-α and prevent the deleterious effects of the soluble factor (see U.S. Pat. No. 5,830,742 issued Nov. 3, 1998).

Select compounds of the invention are potent inhibitors of Aggrecanase, an enzyme important in the degradation of cartilage aggrecan. Aggrecanase is also believed to be an ADAM. The loss of aggrecan from the cartilage matrix is an important factor in the progression of joint diseases such as osteoarthritis and rheumatoid arthritis and inhibition of Aggrecanase is expected to slow or block the loss of cartilage in these diseases.

Other ADAMs that have shown expression in pathological situations include ADAM TS-1 (Kuno, et al., J. Biol. Chem., 272, 556–562 (1997)), and ADAM's 10, 12 and 15 (Wu, et al., Biochem. Biophys. Res. Comm., 235, 437–442, (1997)). As knowledge of the expression, physiological substrates and disease association of the ADAM's increases the full significance of the role of inhibition of this class of enzymes will be appreciated.

The compounds of the present invention are useful in the treatment of diseases in which inhibition of MMP's and/or ADAM's will provide therapeutic benefit, such as those characterized by matrix metalloproteinase or ADAM expression.

The present inventor has also discovered that it is possible to identify inhibitors with differential metalloprotease and reprolysin activity (preferably MMP-13 or Aggrecanase inhibitory activity). One group of preferred inhibitors include those molecules which selectively inhibit Aggrecanase and matrix metalloprotease-13 (MMP-13) preferentially over MMP-1. Another group of preferred inhibitors include those molecules which selectively inhibit Aggrecanase preferentially over MMP-1. Another group of preferred inhibitors include those molecules which selectively inhibit MMP-13 preferentially over MMP-1.

Matrix metalloproteinase and reprolysin inhibitors are well known in the literature. Specifically, European Patent Publication 606,046, published Jul. 13, 1994 refers to certain heterocyclic MMP inhibitors. PCT Publication WO 98/08825 and WO 98/08815, both published Mar. 5, 1998, refer to certain cyclic hydroxamic acid MMP inhibitors. U.S. Pat. No. 5,861,510, issued Jan. 19, 1999, refers to cyclic arylsulfonylamino hydroxamic acids that are useful as MMP inhibitors. PCT Publication WO 98/34918, published Aug. 13, 1998, refers to cyclic hydroxamic acids including certain dialkyl substituted compounds that are useful as MMP inhibitors. PCT publications WO 96/27583 and WO 98/07697, published Mar. 7, 1996 and Feb. 26, 1998, respectively, refer to arylsulfonyl hydroxamic acids. PCT publication WO 98/03516, published Jan. 29, 1998, refers to phosphinates with MMP activity. PCT publication 98/33768, published Aug. 6, 1998, refers to N-unsubstituted arylsulfonylamino hydroxamic acids. European Patent Publication EP 935,963, published Aug. 18, 1999 refers to the use of MMP-13 selective inhibitors for the treatment of osteoarthritis. European Patent Publications 949,245; 949, 246 and 952,148, published Oct. 13, 1999, Oct. 13, 1999 and Oct. 27, 1999, respectively, refer to methods of preparing hydroxamic acids. U.S. Provisional Patent Application No. 60/148464 entitled "Selective Inhibitors of Aggecanase in Osteoarthritis Treatment," filed Aug. 12, 1999 refers to MMP, Aggrecanase and TACE inhibitors and to additional methods of preparing hydroxamic acids. PCT Publications WO 00/09485 and WO 00/09492, both published Feb. 24, 2000, refer to heterocyclic hydroxamic acids. PCT Publication WO 99/05291, published Feb. 4, 1999, refers to Aggrecanase. Each of the above referenced publications and applications is hereby incorporated by reference in its entirety.

SUMMARY OF THE INVENTION

The present invention relates to a compound of the formula

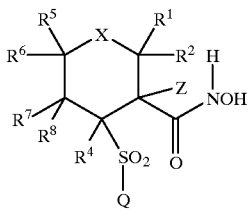

I or the pharmaceutically acceptable salts thereof, wherein

X is oxygen, sulfur, >SO, >SO$_2$ or >NR$^3$;

Z is —OR$^{11}$, —NR$^{12}$R$^{13}$ or (C$_1$–C$_6$)alkyl optionally substituted with one to three substituents (preferably zero, one or two substituents, most preferably zero or one substituent) independently selected from the group consisting of halo, hydroxy, —CN, (C$_1$–C$_6$) alkyl, (C$_2$–C$_6$)alkenyl, (C$_6$–C$_{10}$)aryl(C$_2$–C$_6$)alkenyl, (C$_1$–C$_9$) heteroaryl (C$_2$–C$_6$)alkenyl, (C$_2$–C$_6$) alkynyl, (C$_6$–C$_{10}$) aryl(C$_2$–C$_6$)alkynyl, (C$_1$–C$_9$)heteroaryl(C$_2$–C$_6$) alkynyl, amino, (C$_1$–C$_6$) alkylamino, [(C$_1$–C$_6$)alkyl]$_2$ amino, mercapto, (C$_1$–C$_6$)alkylthio, (C$_1$–C$_6$)alkoxy, perfluoro(C$_1$–C$_6$) alkyl, perfluoro(C$_1$–C$_6$)alkoxy, (C$_6$–C$_{10}$)aryl, (C$_1$–C$_9$)heteroaryl, (C$_3$–C$_9$)heterocyclic, (C$_3$–C$_9$)cycloalkyl, (C$_6$–C$_{10}$)arylamino, (C$_5$–C$_{10}$) arylthio, (C$_6$–C$_{10}$)aryloxy, (C$_1$–C$_9$) heteroarylamino, (C$_1$–C$_9$)heteroarylthio, (C$_1$–C$_9$)heteroaryloxy, (C$_3$–C$_9$) heterocyclic-amino, (C$_3$–C$_9$)heterocyclic-S—, (C$_3$–C$_9$) heterocyclic-O—, (C$_3$–C$_9$)cycloalkylamino, (C$_3$–C$_9$) cycloalkyl-S—, (C$_3$–C$_9$)cycloalkyl-O—, (C$_1$–C$_6$) alkyl-(C=O)—, (C$_1$–C$_6$)alkyl-(C=O)—NH—, (C$_1$–C$_6$)alkyl-(C=O)—S—, (C,-C$_6$)alkyl-(C=O)—O—, (C$_1$–C$_6$)alkoxy-(C=O)—, —CO$_2$H, H$_2$N—(C=O)—, (C$_1$–C$_6$)alkyl-NH—(C=O)— and [(C$_1$–C$_6$)alkyl]$_2$-N—(C=O)—;

R$^1$, R$^2$, R$^5$ and R$^6$ are each independently selected from the group consisting of hydrogen, —CN, (C$_1$–C$_6$)alkyl, (C$_2$–C$_6$)alkenyl, (C$_6$–C$_{10}$)aryl(C$_2$–C$_6$)alkenyl, (C$_1$–C$_9$) heteroaryl(C$_2$–C$_6$) alkenyl, (C$_2$–C$_6$)alkynyl, (C$_6$–C$_{10}$) aryl(C$_2$–C$_6$)alkynyl, (C$_1$–C$_9$)heteroaryl(C$_2$–C$_6$) alkynyl, perfluoro(C$_1$–C$_6$)alkyl, (C$_6$–C$_{10}$)aryl, (C$_1$–C$_9$) heteroaryl, (C$_3$–C$_6$)cycloalkyl, (C$_3$–C$_9$)heterocyclic, (C$_1$–C$_6$)alkyl(C=O)—, (C$_1$–C$_6$)alkoxy-(C=O)—, —CO$_2$H, H$_2$N—(C=O)—, (C$_1$–C$_6$)alkyl-NH—(C=O)— and [(C$_1$–C$_6$)alkyl]$_2$-N—(C=O)—;

wherein said R$^1$, R$^2$, R$^5$ and R$^6$ (C$_1$–C$_6$)alkyl groups are each independently optionally substituted by one to three groups (preferably one or two groups, more preferably one group) selected from halo, trifluoromethyl, hydroxy, amino, —CN, (C$_1$–C$_6$) alkylthio, (C$_1$–C$_6$)alkoxy, (C$_6$–C$_{10}$) aryl, (C$_1$–C$_9$) heteroaryl, (C$_3$–C$_6$)cycloalkyl, (C$_3$–C$_9$)heterocyclic, (C$_6$–C$_{10}$)arylamino, (C$_6$–C$_{10}$)arylthio, (C$_6$–C$_{10}$) aryloxy, (C$_1$–C$_9$)heteroarylamino, (C$_1$–C$_9$) heteroarylthio, (C$_1$–C$_9$) heteroaryloxy, (C$_3$–C$_9$) heterocyclic-amino, (C$_3$–C$_9$)heterocyclic-S—,(C$_3$–C$_9$) heterocyclic-O—, (C$_3$–C$_9$)cycloalkylamino, (C$_3$–C$_9$) cycloalkyl-S—, (C$_3$–C$_9$)cycloalkyl-O—, (C$_6$–C$_{10}$)aryl (C$_1$–C$_2$)alkoxy, (C$_1$–C$_9$)heteroaryl(C$_1$–C$_2$)alkoxy, (C$_1$–C$_6$)alkyl-(C=O)—NH—, (C$_1$–C$_6$)alkyl-(C=O)—S—, (C$_1$–C$_6$)alkyl-(C=O)—O—, (C$_1$–C$_6$) alkylsulfinyl, (C$_6$–C$_{10}$)arylsulfinyl, (C$_1$–C$_6$) alkylsulfonyl, (C$_6$–C$_{10}$)arylsulfonyl, (C$_1$–C$_6$) alkylamino, or ((C$_1$–C$_6$)alkyl)$_2$amino;

R$^3$ is hydrogen; (C$_1$–C$_6$)alkyl optionally substituted by one or more of —CN, perfluoro(C$_1$–C$_6$)alkyl, (C$_6$–C$_{10}$) aryl, (C$_3$–C$_6$)cycloalkyl, (C$_1$–C$_6$)alkyl(C=O)—, (C$_1$–C$_6$)alkoxy-(C=O)—, —CO$_2$H, (C$_1$–C$_6$)alkyl-NH—(C=O)—, and [(C$_1$–C$_6$)alkyl]$_2$-N—(C=O)—; (C$_6$–C$_{10}$)arylsulfonyl; (C$_1$–C$_6$)alkylsulfonyl; (C$_1$–C$_6$) alkyl-NH—(C=O)—; [(C$_1$–C$_6$)alkyl]$_2$-N—(C=O)—; or (R$^{10}$R$^9$N)—(C=O)— wherein R$^9$ and R$^{10}$ are taken together with the nitrogen to which they are attached to form a ring selected from azetidinyl, pyrrolidinyl, piperidinyl, morpholinyl and thiomorpholinyl; (more preferably R$^3$ is hydrogen or (C$_1$–C$_3$)alkyl);

R$^4$ is hydrogen or (C$_1$–C$_4$)alkyl;

R$^7$ and R$^8$ are each independently selected from the group consisting of hydrogen, hydroxy, halo, —CN, (C$_1$–C$_6$) alkyl, (C$_2$–C$_6$)alkenyl, (C$_2$–C$_6$)alkynyl, amino, (C$_1$–C$_6$)alkylamino, [(C$_1$–C$_6$)alkyl]$_2$amino, (C$_1$–C$_6$) alkylthio, (C$_1$–C$_6$)alkoxy, perfluoro(C$_1$–C$_6$)alkyl, perfluoro(C$_1$–C$_6$) alkoxy, (C$_3$–C$_6$)cycloalkyl, (C$_6$–C$_{10}$) aryl, (C$_3$–C$_9$)heterocyclic, (C$_1$–C$_9$)heteroaryl, (C$_6$–C$_{10}$,) arylamino, (C$_6$–C$_{10}$)arylthio, (C$_6$–C$_{10}$) aryloxy, (C$_1$–C$_9$)heteroarylamino, (C$_1$–C$_9$) heteroarylthio, (C$_1$–C$_9$)heteroaryloxy, (C$_3$–C$_9$) heterocyclic-amino, (C$_3$–C$_9$)heterocyclic-S—, (C$_3$–C$_9$) heterocyclic-O—, (C$_3$–C$_9$)cycloalkylamino, (C$_3$–C$_9$) cycloalkyl-S—, (C$_3$–C$_9$)cycloalkyl-O—, (C$_6$–C$_{10}$)aryl (C$_2$–C$_6$) alkenyl, (C$_1$–C$_9$)heteroaryl(C$_2$–C$_6$)alkenyl, (C$_6$–C$_{10}$)aryl(C$_2$–C$_6$)alkynyl, (C$_1$–C$_9$)heteroaryl (C$_2$–C$_6$) alkynyl, (C$_1$–C$_6$)alkyl(C=O)—, (C$_1$–C$_6$)alkyl (C=O)—NH—, (C$_1$–C$_6$)alkyl(C=O)—S—, (C$_1$–C$_6$) alkyl(C=O)—O—, (C$_1$–C$_6$)alkoxy-(C=O)—O—, C$_1$–C$_6$) alkyl-NH—(C=O)— and [(C$_1$–C$_6$)alkyl]$_2$-N—(C=O)—;

wherein each of said R$^7$ and R$^8$ (C$_1$–C$_6$)alkyl groups are independently optionally substituted by one to three substituents (preferably one to two substituents, more preferably one substituent) independently selected from halo, hydroxy, —CN, (C$_1$–C$_6$)alkoxy, (C$_1$–C$_6$) alkylthio, trifluoromethyl, (C$_3$–C$_6$)cycloalkyl, (C$_6$–C$_{10}$)aryl, (C$_3$–C$_9$)heterocyclic, (C$_1$–C$_9$) heteroaryl, (C$_6$–C$_{10}$)arylamino, (C$_6$–C$_{10}$)arylthio, (C$_6$–C$_{10}$)aryloxy, (C$_1$–C$_9$)heteroarylamino, (C$_1$–C$_9$) heteroarylthio, (C$_1$–C$_9$)heteroaryloxy, (C$_3$–C$_9$) heterocyclic-amino, (C$_3$–C$_9$)heterocyclic-S—, (C$_3$–C$_9$) heterocyclic-O—, (C$_3$–C$_9$)cycloalkylamino, (C$_3$–C$_9$) cycloalkyl-S—, (C$_3$–C$_9$)cycloalkyl-O—, (C$_6$–C$_{10}$)aryl (C$_1$–C$_2$)alkoxy, (C$_1$–C$_9$)heteroaryl(C$_1$–C$_2$)alkoxy, (C$_1$–C$_6$)alkyl(C=O)—NH—, (C$_1$–C$_6$) alkyl(C=O)—S—, (C$_1$–C$_6$)alkyl(C=O)—O—, (C$_1$–C$_6$) alkylsulfinyl, (C$_6$–C$_{10}$)arylsulfinyl, (C$_1$–C$_6$) alkylsulfonyl, (C$_6$–C$_{10}$)arylsulfonyl, amino, (C$_1$–C$_6$) alkylamino and ((C$_1$–C$_6$)alkyl)$_2$amino;

or R$^1$ and R$^2$, R$^5$ and R$^6$ or R$^7$ and R$^8$ may be taken together to form a carbonyl group or an optionally substituted (C$_3$–C$_6$)cycloalkyl ring optionally containing 1 or 2 heteroatoms; wherein said heteroatoms may be selected from the group consisting of —S—, —O— or >NH or >N(C$_1$–C$_6$)alkyl; and said optional substituents (i.e. 1–3 substituents per ring) may be selected from $(C_1–C_4)$alkyl, fluoro, chloro, hydroxy, $(C_1–C_4)$ alkoxy and —$NR^{14}R^{15}$;

or $R^5$ and $R^7$, $R^5$ and $R^8$, $R^6$ and $R^7$ or $R^6$ and $R^8$ may be taken together to form an optionally substituted $(C_4–C_6)$cycloalkyl ring optionally containing 1 or 2 heteroatoms; wherein said heteroatoms may be selected from the group consisting of —S—, —O— or >NH or >N$(C_1–C_6)$ alkyl; and said optional substituents (i.e. 1–3 substituents) may be selected from $(C_1–C_4)$ alkyl, fluoro, chloro, hydroxy, $(C_1–C_4)$alkoxy and —$NR^{14}R^{15}$;

$R^{11}$ is hydrogen, $(C_1–C_6)$alkyl, $(C_2–C_6)$alkenyl, $(C_6–C_{10})$ aryl$(C_2–C_6)$alkenyl, $(C_2–C_9)$ heteroaryl$(C_2–C_6)$ alkenyl, $(C_2–C_6)$alkynyl, $(C_6–C_{10})$aryl$(C_2–C_6)$alkynyl, $(C_1–C_9)$heteroaryl$(C_2–C_6)$ alkynyl, perfluoro$(C_1–C_6)$ alkyl, $(C_6–C_{10})$aryl, $(C_1–C_9)$heteroaryl, $(C_3–C_6)$ cycloalkyl, $(C_3–C_9)$ heterocyclic, $(C_1–C_6)$alkyl-(C=O)—, $(C_1–C_6)$alkoxy-(C=O)—, $(C_1–C_6)$alkyl-NH—(C=O)— and $[(C_1–C_6)$ alkyl$]_2$-N—(C=O)—;

$R^{12}$ is hydrogen, $(C_1–C_6)$alkyl, $(C_2–C_6)$alkenyl, $(C_6–C_{10})$ aryl$(C_2–C_6)$alkenyl, $(C_1–C_9)$ heteroaryl$(C_2–C_6)$ alkenyl, $(C_2–C_6)$alkynyl, $(C_6–C_{10})$aryl$(C_2–C_6)$alkynyl, $(C_1–C_9)$heteroaryl$(C_2–C_6)$ alkynyl, perfluoro$(C_1–C_6)$ alkyl, $(C_6–C_{10})$aryl, $(C_1–C_9)$heteroaryl, $(C_3–C_6)$ cycloalkyl, $(C_3–C_9)$ heterocyclic, $(C_1–C_6)$alkyl-(C=O)—, $(C_1–C_6)$alkoxy-(C=O)—, $H_2N$—(C=O)—, $(C_1–C_6)$alkyl-NH—(C=O)— and $[(C_1–C_6)$alkyl$]_2$-N—(C=O)—;

$R^{13}$ is hydrogen, $(C_1–C_6)$alkyl, $(C_2–C_6)$alkenyl, $(C_6–C_{10})$ aryl$(C_2–C_6)$alkenyl, $(C_1–C_9)$ heteroaryl$(C_2–C_6)$ alkenyl, $(C_2–C_6)$alkynyl, $(C_6–C_{10})$aryl$(C_2–C_6)$alkynyl, $(C_1–C_9)$heteroaryl$(C_2–C_6)$ alkynyl, perfluoro$(C_1–C_6)$ alkyl, $(C_8–C_{10})$aryl, $(C_1–C_9)$heteroaryl, $(C_3–C_6)$ cycloalkyl or $(C_3–C_9)$ heterocyclic;

$R^{14}$ is hydrogen, $(C_1–C_6)$alkyl, $(C_2–C_6)$alkenyl, $(C_6–C_{10})$ aryl$(C_2–C_6)$alkenyl, $(C_1–C_9)$ heteroaryl$(C_2–C_6)$ alkenyl, $(C_2–C_6)$alkynyl, $(C_6–C_{10})$aryl$(C_2–C_6)$alkynyl, $(C_1–C_9)$heteroaryl$(C_2–C_6)$ alkynyl, perfluoro$(C_1–C_6)$ alkyl, $(C_6–C_{10})$aryl, $(C_1–C_9)$heteroaryl, $(C_3–C_6)$ cycloalkyl, $(C_3–C_9)$ heterocyclic, $(C_1–C_6)$alkyl-(C=O)—, $(C_1–C_6)$alkoxy-(C=O)—, $H_2N$—(C=O)—, $(C_1–C_6)$alkyl-NH—(C=O)— and $[(C_1–C_6)$alkyl$]_2$-N—(C=O)—;

$R^{15}$ is hydrogen, $(C_1–C_6)$alkyl, $(C_2–C_6)$alkenyl, $(C_6–C_{10})$ aryl$(C_2–C_6)$alkenyl, $(C_1–C_9)$ heteroaryl$(C_2–C_6)$ alkenyl, $(C_2–C_6)$alkynyl, $(C_6–C_{10})$aryl$(C_2–C_6)$alkynyl, $(C_1–C_9)$heteroaryo$(C_2–C_6)$ alkynyl, perfluoro$(C_1–C_6)$ alkyl, $(C_6–C_{10})$aryl, $(C_1–C_9)$heteroaryl, $(C_3–C_6)$ cycloalkyl or $(C_3–C_9)$ heterocyclic;

Q is $(C_1–C_6)$alkyl, $(C_6–C_{10})$aryl, $(C_1–C_9)$heteroaryl, $(C_3–C_9)$heterocyclic, $(C_6–C_{10})$aryl$(C_1–C_6)$ alkyl, $(C_1–C_9)$heteroaryl$(C_1–C_6)$alkyl, $(C_3–C_9)$heterocyclic $(C_1–C_6)$alkyl, $(C_6–C_{10})$aryl$(C_6–C_{10})$aryl, $(C_6–C_{10})$aryl $(C_1–C_9)$heteroaryl, $(C_6–C_{10})$aryl$(C_3–C_9)$heterocyclic, $(C_1–C_9)$heteroaryl$(C_6–C_{10})$aryl, $(C_1–C_9)$ heteroaryl $(C_1–C_9)$heteroaryl, $(C_1–C_9)$heteroaryl$(C_3–C_9)$ heterocyclic, $(C_3–C_9)$heterocyclic$(C_6–C_{10})$ aryl, $(C_3–C_9)$heterocyclic$(C_1–C_9)$heteroaryl, $(C_3–C_9)$ heterocyclic$(C_3–C_9)$heterocyclic, $(C_6–C_{10})$ aryloxy $(C_1–C_6)$alkyl, $(C_6–C_{10})$aryloxy$(C_6–C_{10})$aryl, $(C_6–C_{10})$ aryloxy$(C_1–C_9)$heteroaryl, $(C_6–C_{10})$ aryloxy$(C_3–C_9)$ heterocyclic, $(C_1–C_9)$heteroaryloxy$(C_1–C_6)$alkyl, $(C_1–C_9)$heteroaryloxy$(C_6–C_{10})$ aryl, $(C_1–C_9)$ heteroaryloxy$(C_1–C_9)$heteroaryl, $(C_1–C_9)$ heteroaryloxy$(C_3–C_9)$heterocyclic, $(C_3–C_9)$ heterocyclic-O—$(C_1–C_6)$alkyl, $(C_3–C_9)$heterocyclic-O—$(C_6–C_{10})$aryl, $(C_3–C_9)$heterocyclic-O—$(C_1–C_9)$ heteroaryl, $(C_3–C_9)$heterocyclic-O—$(C_3–C_9)$ heterocyclic, $(C_6–C_{10})$aryl$(C_1–C_6)$alkyl$(C_6–C_{10})$aryl, $(C_6–C_{10})$aryl$(C_1–C_6)$alkyl$(C_1–C_9)$heteroaryl, $(C_6–C_{10})$ aryl$(C_1–C_6)$alkyl$(C_3–C_9)$heterocyclic, $(C_6–C_{10})$ aryl $(C_1–C_6)$alkoxy$(C_6–C_{10})$aryl, $(C_6–C_{10})$aryl$(C_1–C_6)$ alkoxy$(C_1–C_9)$heteroaryl, $(C_6–C_{10})$aryl$(C_1–C_6)$ alkoxy $(C_3–C_9)$heterocyclic, $(C_6–C_{10})$aryloxy$(C_1–C_6)$alkyl $(C_6–C_{10})$aryl, $(C_6–C_{10})$aryloxy$(C_1–C_6)$ alkyl$(C_1–C_9)$ heteroaryl, $(C_6–C_{10})$aryloxy$(C_1–C_6)$alkyl$(C_3–C_9)$ heterocyclic, $(C_1–C_9)$heteroaryl$(C_1–C_6)$ alkyl$(C_6–C_{10})$ aryl, $(C_1–C_9)$heteroaryl$(C_1–C_6)$alkyl$(C_1–C_9)$ heteroaryl, $(C_1–C_9)$heteroaryl$(C_1–C_6)$ alkyl$(C_3–C_9)$ heterocyclic, $(C_1–C_9)$heteroaryl$(C_1–C_6)$alkoxy $(C_6–C_{10})$aryl, $(C_1–C_9)$heteroaryl$(C_1–C_6)$ alkoxy $(C_1–C_9)$heteroaryl, $(C_1–C_9)$heteroaryl$(C_1–C_6)$alkoxy $(C_3–C_9)$heterocyclic, $(C_1–C_9)$ heteroaryloxy$(C_1–C_6)$ alkyl$(C_6–C_{10})$aryl, $(C_1–C_9)$heteroaryloxy$(C_1–C_6)$alkyl $(C_1C_9)$heteroaryl, $(C_1–C_9)$ heteroaryloxy$(C_1–C_6)$alkyl $(C_3–C_9)$heterocyclic, $(C_3–C_9)$heterocyclic$(C_1–C_6)$ alkyl$(C_6–C_{10})$aryl, $(C_3–C_9)$ heterocyclic$(C_1–C_6)$alkyl $(C_1–C_9)$heteroaryl, $(C_3–C_9)$heterocyclic$(C_1–C_6)$alkyl $(C_3C_9)$heterocyclic, $(C_3–C_9)$heterocyclic$(C_1–C_6)$ alkoxy$(C_6–C_{10})$aryl, $(C_3–C_9)$heterocyclic$(C_1–C_9)$ alkoxy$(C_1–C_9)$heteroaryl, $(C_3–C_9)$heterocyclic$(C_1–C_6)$ alkoxy$(C_3–C_9)$heterocyclic, $(C_3–C_9)$heterocyclic-O—$(C_1–C_6)$alkyl$(C_6–C_{10})$ aryl, $(C_3–C_9)$heterocyclic-O—$(C_1–C_6)$alkyl$(C_1–C_9)$heteroaryl, $(C_3–C_9)$heterocyclic-O—$(C_1–C_6)$ alkyl$(C_3–C_9)$heterocyclic, $(C_6–C_{10})$aryl $(C_6–C_{10})$aryl$(C_1–C_6)$alkyl, $(C_6–C_{10})$aryl-NH—$(C_1–C_6)$alkyl, $(C_6–C_{10})$aryl-NH—$(C_6–C_{10})$aryl, $(C_6–C_{10})$aryl-NH—$(C_1–C_9)$heteroaryl, $(C_6–C_{10})$aryl-NH—$(C_3–C_9)$ heterocyclic, $(C_1–C_9)$heteroaryl-NH—$(C_1–C_6)$alkyl, $(C_1–C_9)$heteroaryl-NH—$(C_6–C_{10})$aryl, $(C_1–C_9)$ heteroaryl-NH—$(C_1–C_9)$heteroaryl, $(C_1–C_9)$ heteroaryl-NH—$(C_3–C_9)$heterocyclic, $(C_3–C_9)$ heterocyclic-NH—$(C_1–C_6)$alkyl, $(C_3–C_9)$heterocyclic-NH—$(C_6–C_{10})$aryl, $(C_3–C_9)$heterocyclic-NH—$(C_1–C_9)$ heteroaryl, $(C_3–C_9)$heterocyclic-NH—$(C_3–C_9)$heterocyclic, $(C_6–C_{10})$aryl$(C_1–C_6)$alkyl-NH—$(C_6–C_{10})$ aryl, $(C_6–C_{10})$aryl$(C_1–C_6)$alkyl-NH—$(C_1–C_9)$heteroaryl, $(C_6–C_{10})$aryl$(C_1–C_6)$alkyl-NH—$(C_3–C_9)$ heterocyclic, $(C_6–C_{10})$aryl-NH—$(C_1–C_6)$ alkyl$(C_6–C_{10})$aryl, $(C_6–C_{10})$aryl-NH—$(C_1–C_9)$alkyl $(C_1–C_9)$ heteroaryl, $(C_6–C_{10})$aryl-NH—$(C_1–C_6)$alkyl $(C_3–C_9)$heterocyclic, $(C_1–C_9)$heteroaryl$(C_1–C_6)$alkyl-NH—$(C_6–C_{10})$ aryl, $(C_1–C_9)$heteroaryl$(C_1–C_9)$alkyl-NH—$(C_1–C_9)$heteroaryl, $(C_1–C_9)$heteroaryl$(C_1–C_6)$ alkyl-NH—$(C_3–C_9)$ heterocyclic, $(C_1–C_9)$heteroaryl-NH—$(C_1–C_6)$alkyl$(C_6–C_{10})$aryl, $(C_1–C_9)$heteroaryl-NH—$(C_1–C_6)$ alkyl$(C_1–C_9)$heteroaryl, $(C_1–C_9)$ heteroaryl-NH—$(C_1–C_6)$alkyl$(C_3–C_9)$heterocyclic, $(C_3–C_9)$ heterocyclic$(C_1–C_9)$alkyl-NH—$(C_6–C_{10})$aryl, $(C_3–C_9)$heterocyclic$(C_1–C_6)$alkyl-NH—$(C_1–C_9)$ heteroaryl, $(C_3–C_9)$heterocyclic$(C_1–C_6)$alkyl-NH—$(C_3–C_9)$heterocyclic, $(C_3–C_9)$heterocyclic-NH—$(C_1–C_6)$ alkyl$(C_6–C_{10})$aryl, $(C_3–C_9)$heterocyclic-NH—$(C_1–C_6)$alkyl$(C_1–C_9)$heteroaryl, $(C_3–C_9)$ heterocyclic-NH—$(C_1–C_6)$alkyl$(C_3–C_9)$heterocyclic, $(C_6–C_{10})$aryl$(C_1–C_6)$alkyl-NH—$(C_1–C_6)$alkyl or $(C_6–C_{10})$aryl$(C_1–C_6)$alkoxy$(C_1–C_6)$alkyl, wherein each of said $(C_6–C_{10})$aryl, $(C_1–C_9)$heteroaryl or $(C_3–C_9)$heterocyclic groups (where ever they occur) may optionally be substituted by one or more substituents, preferably one to three substituents per ring, most preferably one to three substituents on the terminal ring independently selected from the group consisting of halo, —CN, $(C_1-C_6)$alkyl optionally substituted with one or more fluorine atoms, hydroxy, hydroxy-$(C_1-C_6)$ alkyl, $(C_1-C_6)$alkoxy optionally substituted with one or more fluorine atoms, $(C_1-C_6)$ alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$ alkyl-O—(C=O)—$(C_1-C_6)$alkyl, $(C_1-C_6)$alkyl-(C=O)—O—, $(C_1-C_6)$alkyl-(C=O)—O—$(C_1-C_6)$ alkyl, H(O=C)—, H(O=C)—$(C_1-C_6)$alkyl, $(C_1-C_6)$ alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$ amino, amino$(C_1-C_6)$alkyl, $(C_1-C_6)$alkylamino $(C_1-C_9)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$ alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$ alkyl(C=O)—[N$(C_1-C_6)$alkyl]$(C_1-C_6)$alkyl, $(C_1-C_6)$ alkyl-S—, $(C_1-C_6)$alkyl-(S=O)—, $(C_1-C_6)$alkyl-$SO_2$—, $(C_1-C_6)$alkyl-$SO_2$—NH—, $(C_1-C_6)$alkyl-$SO_2$-[N—$(C_1-C_9)$alkyl]-, $H_2N$—$SO_2$—, $H_2N$—$SO_2$-$(C_1-C_9)$alkyl, $(C_1-C_6)$alkylHN—$SO_2$-$(C_1-C_6)$alkyl, $[(C_1-C_6)$alkyl$]_2N$—$SO_2$-$(C_1-C_6)$alkyl, $CF_3SO_2$—, $(C_1-C_6)$alkyl-$SO_2$—, phenyl, phenyl$(C_1-C_9)$alkyl, $(C_3-C_{10})$cycloalkyl, $(C_1-C_9)$heterocycloalkyl, and $(C_1-C_9)$heteroaryl.

The term "D- or L-amino acid", as used herein, unless otherwise indicated, includes glycine, alanine, valine, leucine, isoleucine, phenylalanine, asparagine, glutamine, tryptophan, proline, serine, threonine, tyrosine, hydroxyproline, cysteine, cystine, methionine, aspartic acid, glutamic acid, lysine, arginine or histidine.

The positions on the ring of formula I, as used herein, are defined as follows:

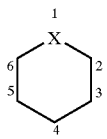

The compound of formula I may have chiral centers and therefore exist in different enantiomeric forms. This invention relates to all optical isomers, diasteriomers, atropisomers, stereoisomers and tautomers of the compounds of formula I and mixtures thereof. The preferred stereochemistry is as follows:

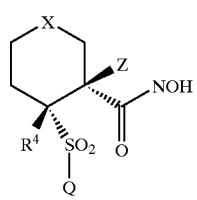

I'

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitantrate, succinate, maleate, fumarate, gluconate, saccharate, benzoate, methanesulfonate, ethanesulfonate, benzenesulfonate, p-toluenesulfonate and pamoate [ie., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (eg, potassium and sodium) and alkaline earth metal cations (eg., calcium and magnesium), ammonium or water-soluble amine addition salts such as N-methylglucamine-(meglumine), and the lower alkanolammonium and other base salts of pharmaceutically acceptable organic amines.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labelled compounds of Formula I of this invention and prodrugs thereof can generally be prepared by carrying out the procedures disclosed in the Schemes and/or in the Examples and Preparations below, by substituting a readily available isotopically-labelled reagent for a non-isotopically-labelled reagent.

As used herein, the term "alkyl," as well as the alkyl moieties of other groups referred to herein (eg., alkoxy), may be linear or branched (such as methyl, ethyl, n-propyl, isopropyl, n-butyl, iso-butyl, secondary-butyl, tertiary-butyl), and they may also be cyclic (e.g., cyclopropyl or cyclobutyl); optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. The phrase "each of said alkyl" as used herein refers to any of the preceding alkyl moieties within a group such alkoxy, alkenyl or alkylamino. Preferred alkyls include $(C_1-C_4)$alkyl, most preferably methyl.

As used herein, the term "cycloalkyl" refers to a mono or bicyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1] heptanyl, bicyclo[3.2.1]octanyl and bicyclo[5.2.0]nonanyl, etc.); optionally containing 1–2 double bonds and optionally substituted by 1 to 3 suitable substituents as defined below such as fluoro, chloro, trifluoromethyl, $(C_1-C_6)$ alkoxy, $(C_6-C_{10})$aryloxy, trifluoromethoxy, difluoromethoxy or $(C_1-C_6)$alkyl, more preferably fluoro, chloro, methyl, ethyl and methoxy.

As used herein, the term "halogen" includes fluoro, chloro, bromo or iodo or fluoride, chloride, bromide or iodide.

As used herein, the term "mercapto" refers to the group —SH.

As used herein, the term "halo-substituted alkyl" refers to an alkyl radical as described above substituted with one or more halogens included, but not limited to, chloromethyl, dichloromethyl, fluoromethyl, difluoromethyl, trifluoromethyl, 2,2,2-trichloroethyl, and the like; optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined below such as fluoro, chloro, trifluoromethyl, $(C_1-C_9)$alkoxy, $(C_6-C_{10})$aryloxy, trifluoromethoxy, difluoromethoxy or $(C_1-C_6)$alkyl.

As used herein, the term "$(C_2-C_6)$alkynyl" is used herein to mean straight or branched hydrocarbon chain radicals having one triple bond including, but not limited to, ethynyl, propynyl, butynyl, and the like; optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "alkoxyiminyl" refers to a group of the formula —C=N—O—R, wherein R is alkyl or aryl optionally substituted with a suitable substituent. Examples of such groups are methoxyiminyl and phenoxyiminyl.

As used herein, the term "carbonyl" (as used in phrases such as alkylcarbonyl or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "$(C_1-C_6)$alkyl-[$(C_6-C_{10})$aryl-]N—(C=O)—" as used herein, refers to a disubstituted amide group of the formula

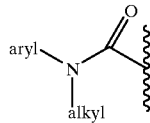

As used herein, the term "aryl" means aromatic radicals such as phenyl, naphthyl, tetrahydronaphthyl, indanyl and the like; optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl, more preferably fluoro, chloro, methyl, ethyl and methoxy.

As used herein, the term "heteroaryl" refers to an aromatic heterocyclic group usually with one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), tetrazole, quinolyl, isoquinolyl, benzothienyl, benzofuryl, indolyl, and the like; optionally substituted by 1 to 3 suitable substituents as defined below such as fluoro, chloro, trifluoromethyl, $(C_1-C_9)$alkoxy, $(C_6-C_{hd\ 10})$aryloxy, trifluoromethoxy, difluoromethoxy or $(C_1-C_6)$alkyl, more preferably fluoro, chloro, methyl, ethyl and methoxy. Particularly preferred heteroaryl groups include pyridyl, pyrimidinyl, pyrazinyl, quinolyl, isoquinolyl, thienyl and thiazolyl (these heteroaryls are the more preferred of the Q heteroaryls, more preferably the terminal Q heteroaryl moiety, most preferably optionally substituted pyridin-3-yl, pyridin-4-yl, quinolin-3-yl, quinolin-4-yl, quinolin-5-yl, quinolin-6-yl, isoquinolin-3-yl, isoquinolin-4-yl, isoquinolin-5-yl, isoquinolin-6-yl, pyrazinyl and pyrimidin-5-yl).

The term "heterocyclic" as used herein refers to a cyclic group containing 3–9 carbon atoms and 1–4 hetero atoms selected from N, O, S or NR'. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholine, 1,2-tetrahydrothiazin-2-yl, 1,3-tetrahydrothiazin-3-yl, tetrahydrothiadiazine, morpholine, 1,2-tetrahydrodiazin-2-yl, 1,3-tetrahydrodiazin-1-yl, 1,4-oxazin-2-yl, 1,2,5-oxathiazin-4-yl and the like; optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl, more preferably fluoro, chloro, methyl, ethyl and methoxy.

As used herein, the term "a suitable substituent" is intended to mean a chemically and pharmaceutically acceptable functional group i.e., a moiety that does not negate the inhibitory activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, —CO$_2$H groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, and arylsulfonyl groups and the like.

An embodiment of the present invention includes compounds of formula I, referred to as the Tetrahydropyran Group of compounds are those compounds wherein X is —O—. Another embodiment of the present invention includes compounds of formula I, referred to as the Tetrahydrothiopyran Group of compounds are those compounds wherein X is —S—. Another embodiment of the present invention includes compounds of formula 1, referred to as the Tetrahydrothiopyran oxide Group of compounds are those compounds wherein X is >S=O. Another embodiment of the present invention includes compounds of formula I, referred to as the Tetrahydrothiopyran-11-dioxide Group of compounds are those compounds wherein X is >$SO_2$. Another embodiment of the present invention includes compounds of formula I, referred to as the Piperidine Group of compounds are those compounds wherein X is >$NR^3$.

An embodiment of the present invention includes compounds of formula I, referred to as the hydroxy-Tetrahydropyran Group of compounds are those compounds wherein X is —O— and Z is —$OR^{11}$ and $R^{11}$ is hydrogen. Another embodiment of the present invention includes compounds of formula I, referred to as the hydroxy-Tetrahydrothiopyran Group of compounds are those compounds wherein X is —S— and Z is —$OR^{11}$ and $R^{11}$ is hydrogen. Another embodiment of the present invention includes compounds of formula I, referred to as the hydroxy-Tetrahydrothiopyran oxide Group of compounds are those compounds wherein X is >S=O and Z is —$OR^{11}$ and $R^{11}$ is hydrogen. Another embodiment of the present invention includes compounds of formula I, referred to as the hydroxy-Tetrahydrothiopyran-1,1-dioxide Group of compounds are those compounds wherein X is >$SO_2$ and Z is —$OR^{11}$ and $R^{11}$ is hydrogen. Another embodiment of the present invention includes compounds of formula I, referred to as the hydroxy-Piperidine Group of compounds are those compounds wherein X is >$NR^3$ and Z is —$OR^{11}$ and $R^{11}$ is hydrogen.

An embodiment of the present invention includes compounds of formula I, referred to as the Tetrahydropyran-Ether Group of compounds are those compounds wherein X is —O— and Z is —$OR^{11}$ and $R^{11}$ is other than hydrogen. Another embodiment of the present invention includes compounds of formula I, referred to as the Tetrahydrothiopyran-Ether Group of compounds are those compounds wherein X is —S— and Z is —$OR^{11}$ and $R^{11}$ is other than hydrogen. Another embodiment of the present invention includes compounds of formula I, referred to as the Tetrahydrothiopyran oxide-Ether Group of compounds are those compounds wherein X is >S=O and Z is —$OR^{11}$ and $R^{11}$ is other than hydrogen. Another embodiment of the present invention includes compounds of formula I, referred to as the Tetrahydrothiopyran-1,1-dioxide-Ether Group of compounds are those compounds wherein X is >$SO_2$ and Z is —$OR^{11}$ and $R^{11}$ is other than hydrogen. Another embodiment of the present invention includes compounds of formula I, referred to as the Piperidine-Ether Group of compounds are those compounds wherein X is >$NR^3$ and Z is —$OR^{11}$ and $R^{11}$ is other than hydrogen.

An embodiment of the present invention includes compounds of formula I, referred to as the Amino-Tetrahydropyran Group of compounds are those compounds wherein X is —O— and Z is —$NR^{12}R^{13}$. Another embodiment of the present invention includes compounds of formula I, referred to as the Amino-Tetrahydrothiopyran Group of compounds are those compounds wherein X is —S— and Z is —$NR^{12}R^{13}$. Another embodiment of the present invention includes compounds of formula I, referred to as the Amino-Tetrahydrothiopyran oxide Group of compounds are those compounds wherein X is >S=O and Z is —$NR^{12}R^{13}$. Another embodiment of the present invention includes compounds of formula I, referred to as the Amino-Tetrahydrothiopyran-1,1-dioxide Group of compounds are those compounds wherein X is >$SO_2$ and Z is —$NR^{12}R^{13}$. Another embodiment of the present invention includes compounds of formula I, referred to as the Amino-Piperidine Group of compounds are those compounds wherein X is >$NR^3$ and Z is —$NR^{12}R^{13}$.

An embodiment of the present invention includes compounds of formula I, referred to as the Alkyl-Tetrahydropyran Group of compounds are those compounds wherein X is —O— and Z is ($C_1$–$C_6$)alkyl. Another embodiment of the present invention includes compounds of formula I, referred to as the Alkyl-Tetrahydrothiopyran Group of compounds are those compounds wherein X is —S— and Z is ($C_1$–$C_6$)alkyl. Another embodiment of the present invention includes compounds of formula I, referred to as the Alkyl-Tetrahydrothiopyran oxide Group of compounds are those compounds wherein X is >S=O and Z is ($C_1$–$C_6$) alkyl. Another embodiment of the present invention includes compounds of formula I, referred to as the Alkyl-Tetrahydrothiopyran-1,1-dioxide-Ether Group of compounds are those compounds wherein X is >$SO_2$ and Z is ($C_1$–$C_6$)alkyl. Another embodiment of the present invention includes compounds of formula I, referred to as the Alkyl-Piperidine Group of compounds are those compounds wherein X is >$NR^3$ and Z is ($C_1$–$C_6$)alkyl.

Preferred compounds of the present invention are those wherein X is >$NR^3$, more preferably wherein $R^3$ is hydrogen.

Other preferred compounds of the present invention are those wherein X is —O—.

Most preferred compounds of the present invention are those wherein Z is —$OR^{11}$, more preferably wherein $R^{11}$ is hydrogen, ($C_1$–$C_6$)alkyl, ($C_2$–$C_6$)alkenyl, ($C_2$–$C_6$)alkynyl, perfluoro($C_1$–$C_6$)alkyl, ($C_6$–$C_{10}$)aryl, ($C_1$–$C_9$)heteroaryl, ($C_3$–$C_6$)cycloalkyl, ($C_3$–$C_9$)heterocyclic, ($C_1$–$C_6$)alkyl-(C=O)—, ($C_1$–$C_6$)alkoxy-(C=O)— or ($C_1$–$C_6$)alkyl-NH—(C=O)—; more preferably hydrogen, ($C_1$–$C_4$)alkyl or ($C_2$–$C_4$)alkenyl; most preferably wherein $R^{11}$ is hydrogen.

Other preferred compounds of the present invention are those wherein Z is —$NR^{12}R^{13}$, more preferably wherein $R^{12}$ is hydrogen, ($C_1$–$C_6$)alkyl, ($C_2$–$C_6$)alkenyl, ($C_2$–$C_6$)alkynyl, ($C_6$–$C_{10}$) aryl, ($C_1$–$C_9$)heteroaryl, ($C_3$–$C_6$)cycloalkyl, ($C_3$–$C_9$)heterocyclic, ($C_1$–$C_6$)alkyl-(C=O)—, ($C_1$–$C_6$) alkoxy-(C=O)—, $H_2N$—(C=O)—, ($C_1$–$C_6$)alkyl-NH—(C=O)—, or [($C_1$–$C_6$)alkyl]$_2$-N—(C=O)—; more preferably wherein $R^{12}$ is hydrogen, ($C_1$–$C_6$)alkyl, ($C_2$–$C_6$)alkenyl, ($C_2$–$C_6$)alkynyl, ($C_6$–$C_{10}$)aryl; more preferably wherein $R^{12}$ is hydrogen, ($C_1$–$C_6$)alkyl or ($C_2$–$C_6$)alkenyl; and wherein $R^{13}$ is hydrogen, ($C_1$–$C_6$)alkyl, ($C_2$–$C_6$)alkenyl, ($C_2$–$C_6$)alkynyl, ($C_6$–$C_{10}$)aryl, ($C_1$–$C_9$)heteroaryl, ($C_3$–$C_6$)cycloalkyl or ($C_3$–$C_9$)heterocyclic; more preferably wherein $R^{13}$ is hydrogen, ($C_1$–$C_6$)alkyl, ($C_2$–$C_6$)alkenyl, ($C_2$–$C_6$)alkynyl or ($C_6$–$C_{10}$)aryl; more preferably wherein $R^{13}$ is hydrogen, ($C_1$–$C_6$) alkyl or ($C_2$–$C_6$)alkenyl; most preferably wherein $R^{13}$ is hydrogen. Most preferred compounds of formula I, wherein Z is —$NR^{12}R^{13}$, are those wherein both $R^{12}$ and $R^{13}$ are hydrogen.

Preferred compounds wherein Z is optionally substituted ($C_1$–$C_6$)alkyl are those wherein the substituents are halo, hydroxy, ($C_1$–$C_6$)alkyl, amino, ($C_1$–$C_6$)alkylamino, [($C_1$–$C_6$) alkyl]$_2$amino, ($C_1$–$C_6$)alkoxy, ($C_6$–$C_{10}$)aryl, ($C_1$–$C_9$)heteroaryl; more preferably wherein said Z ($C_1$–$C_6$) alkyl group is mono or disubstituted (except for halo), most preferably wherein said substituent is selected from hydroxy, ($C_1$–$C_4$)alkyl, amino, ($C_1$–$C_2$)alkylamino, [($C_1$–$C_2$) alkyl]$_2$amino, ($C_1$–$C_3$)alkoxy and phenyl.

Most preferred compounds of the present invention are those wherein X is —O— and Z is —$OR^{11}$.

Other preferred compounds of the present invention are those wherein X is —O— and Z is —$NR^{12}R^{13}$.

Another embodiment of the invention (referred to as the Alkyl or Aryl Q's) include compounds of formula I wherein Q is $(C_1-C_6)$alkyl, $(C_6-C_{10})$aryl, $(C_1-C_9)$heteroaryl, $(C_3-C_9)$ heterocyclic, $(C_6-C_{10})$aryl$(C_1-C_6)$alkyl, $(C_1-C_9)$heteroaryl$(C_1-C_6)$alkyl, $(C_3-C_9)$heterocyclic$(C_1-C_6)$ alkyl, $(C_6-C_{10})$aryl$(C_6-C_{10})$aryl, $(C_6-C_{10})$aryl$(C_1-C_9)$heteroaryl, $(C_6-C_{10})$aryl$(C_3-C_9)$heterocyclic, $(C_1-C_9)$heteroaryl $(C_6-C_{10})$aryl, $(C_1-C_9)$heteroaryl$(C_1-C_9)$heteroaryl, $(C_1-C_9)$heteroaryl$(C_3-C_9)$ heterocyclic, $(C_3-C_9)$ heterocyclic$(C_6-C_{10})$aryl, $(C_1-C_9)$heteroaryl$(C_3-C_9)$ heterocyclic, $(C_3-C_9)$ heterocyclic$(C_3-C_9)$heterocyclic or $(C_6-C_{10})$aryl$(C_6-C_{10})$aryl$(C_1-C_6)$alkyl.

Another embodiment of the invention (referred to as the Aryl-Ethers) include compounds of formula I wherein Q is $(C_6-C_{10})$aryloxy$(C_1-C_6)$alkyl, $(C_6-C_{10})$aryloxy$(C_6-C_{10})$ aryl, $(C_6-C_{10})$aryloxy$(C_1-C_9)$heteroaryl, $(C_6-C_{10})$aryloxy $(C_3-C_9)$heterocyclic, $(C_1-C_9)$heteroaryloxy$(C_1-C_6)$ alkyl, $(C_1-C_9)$heteroaryloxy$(C_6-C_{10})$aryl, $(C_1-C_9)$heteroaryloxy $(C_1-C_9)$heteroaryl $(C_1-C_9)$ heteroaryloxy$(C_3-C_9)$ heterocyclic, $(C_3-C_9)$heterocyclic-O—$(C_1-C_6)$alkyl, $(C_3-C_9)$heterocyclic-O—$(C_6-C_{10})$ aryl, $(C_3-C_9)$heterocyclic-O—$(C_1-C_9)$heteroaryl or $(C_3-C_9)$heterocyclic-O—$(C_3-C_9)$ heterocyclic.

Another embodiment of the invention (referred to as the Aryl-Alkyl-Ethers) include compounds of formula I wherein Q is $(C_6-C_{10})$aryl$(C_1-C_6)$alkoxy$(C_6-C_{10})$aryl, $(C_6-C_{10})$aryl $(C_1-C_6)$ alkoxy$(C_1-C_9)$heteroaryl, $(C_6-C_{10})$aryl$(C_1-C_6)$ alkoxy$(C_3-C_9)$heterocyclic, $(C_1-C_9)$heteroaryl$(C_1-C_6)$ alkoxy$(C_6-C_{10})$aryl, $(C_1-C_9)$heteroaryl$(C_1-C_6)$alkoxy $(C_1-C_9)$heteroaryl, $(C_1-C_9)$heteroaryl$(C_1-C_6)$ alkoxy $(C_3-C_9)$heterocyclic, $(C_3-C_9)$heterocyclic$(C_1-C_6)$alkoxy $(C_6-C_{10})$aryl, $(C_3-C_9)$ heterocyclic$(C_1-C_6)$alkoxy$(C_1-C_9)$ heteroaryl or $(C_3-C_9)$heterocyclic$(C_1-C_6)$alkoxy$(C_3-C_9)$ heterocyclic.

Another embodiment of the invention (referred to as the Reverse-ethers) include compounds of formula I wherein Q is $(C_6-C_{10})$aryloxy$(C_1-C_6)$alkyl$(C_6-C_{10})$aryl, $(C_6-C_{10})$ aryloxy$(C_1-C_6)$ alkyl$(C_1-C_9)$heteroaryl, $(C_6-C_{10})$aryloxy $(C_1-C_6)$alkyl$(C_3-C_9)$heterocyclic, $(C_1-C_9)$heteroaryloxy $(C_1-C_6)$alkyl$(C_6-C_{10})$aryl, $(C_1-C_9)$heteroaryloxy$(C_1-C_6)$ alkyl$(C_1-C_9)$heteroaryl, $(C_1-C_9)$ heteroaryloxy$(C_1-C_6)$ alkyl$(C_3-C_9)$heterocyclic, $(C_3-C_9)$heterocyclic-O—$(C_1-C_6)$alkyl$(C_6-C_{10})$aryl, $(C_3-C_9)$heterocyclic-O—$(C_1-C_9)$alkyl$(C_1-C_9)$heteroaryl or $(C_3-C_9)$heterocyclic-O—$(C_1-C_6)$alkyl$(C_3-C_9)$ heterocyclic.

Another embodiment of the invention (referred to as the Chain-Aryls) include compounds of formula I wherein Q is $(C_6-C_{10})$aryl$(C_1-C_6)$alkyl$(C_6-C_{10})$aryl, $(C_6-C_{10})$aryl $(C_1-C_6)$ alkyl$(C_1-C_9)$heteroaryl, $(C_6-C_{10})$aryl$(C_1-C_6)$alkyl $(C_3-C_9)$heterocyclic, $(C_1-C_9)$heteroaryl$(C_1-C_6)$ alkyl $(C_6-C_{10})$aryl, $(C_1-C_9)$heteroaryl$(C_1-C_6)$alkyl$(C_1-C_9)$ heteroaryl, $(C_1-C_9)$heteroaryl$(C_1-C_6)$ alkyl$(C_3-C_9)$ heterocyclic, $(C_3-C_9)$heterocyclic$(C_1-C_6)$alkyl$(C_6-C_{10})$ aryl, $(C_3-C_9)$heterocyclic$(C_1-C_6)$ alkyl$(C_1-C_9)$heteroaryl or $(C_3-C_9)$heterocyclic$(C_1-C_6)$alkyl$(C_3-C_9)$heterocyclic.

Another embodiment of the invention (referred to as the Amino-aryls) include compounds of formula I wherein Q is $(C_6-C_{10})$aryl-NH—$(C_1-C_6)$alkyl, $(C_6-C_{10})$aryl-NH—$(C_6-C_{10})$aryl, $(C_6-C_{10})$aryl-NH—$(C_1-C_9)$heteroaryl, $(C_6-C_{10})$aryl-NH—$(C_3-C_9)$heterocyclic, $(C_1-C_9)$ heteroaryl-NH—$(C_1-C_6)$ alkyl, $(C_1-C_9)$heteroaryl-NH—$(C_6-C_{10})$aryl, $(C_1-C_9)$heteroaryl-NH—$(C_1-C_9)$heteroaryl, $(C_1-C_9)$heteroaryl-NH—$(C_3-C_9)$heterocyclic, $(C_3-C_9)$ heterocyclic-NH—$(C_1-C_6)$alkyl, $(C_3-C_9)$heterocyclic-NH—$(C_6-C_{10})$aryl, $(C_3-C_9)$heterocyclic-NH—$(C_1-C_9)$ heteroaryl, $(C.-C_9)$heterocyclic-NH—$(C_3-C_9)$ heterocyclic, $(C_6-C_{10})$aryl$(C_1-C_6)$alkyl-NH—$(C_6-C_{10})$aryl, $(C_6-C_{10})$ aryl$(C_1-C_6)$alkyl-NH—$(C_1-C_9)$ heteroaryl, $(C_6-C_{10})$aryl $(C_1-C_6)$alkyl-NH—$(C_3-C_9)$heterocyclic, $(C_6-C_{10})$aryl-NH—$(C_1-C_6)$alkyl$(C_6-C_{10})$ aryl, $(C_6-C_{10})$aryl-NH—$(C_1-C_6)$alkyl$(C_1-C_9)$heteroaryl, $(C_6-C_{10})$aryl-NH—$(C_1-C_6)$alkyl$(C_3-C_9)$ heterocyclic, $(C_1-C_9)$heteroaryl $(C_1-C_6)$alkyl-NH—$(C_6-C_{10})$aryl, $(C_1-C_9)$heteroaryl $(C_1-C_6)$alkyl-NH—$(C_1-C_9)$ heteroaryl, $(C_1-C_9)$heteroaryl $(C_1-C_6)$alkyl-NH—$(C_3-C_9)$heterocyclic, $(C_1-C_9)$ heteroaryl-NH—$(C_1-C_6)$ alkyl$(C_6-C_{10})$aryl, $(C_1-C_9)$ heteroaryl-NH—$(C_1-C_6)$alkyl$(C_1-C_9)$heteroaryl, $(C_1-C_9)$ heteroaryl-NH—$(C_1-C_6)$alkyl$(C_3-C_9)$heterocyclic, $(C_3-C_9)$ heterocyclic$(C_1-C_6)$alkyl-NH—$(C_6-C_{10})$aryl, $(C_3-C_9)$ heterocyclic$(C_1-C_6)$alkyl-NH—$(C_1-C_9)$heteroaryl, $(C_3-C_9)$ heterocyclic$(C_1 -C_9)$alkyl-NH—$(C_3-C_9)$ heterocyclic, $(C_3-C_9)$heterocyclic-NH—$(C_1-C_6)$alkyl$(C_6-C_{10})$aryl, $(C_3-C_9)$heterocyclic-NH—$(C_1-C_6)$ alkyl$(C_1-C_9)$heteroaryl, $(C_3-C_9)$heterocyclic-NH—$(C_1-C_6)$alkyl$(C_3-C_9)$ heterocyclic, $(C_6-C_{10})$ aryl$(C_1-C_6)$alkyl-NH—$(C_1-C_6)$ alkyl or $(C_6-C_{10})$aryl$(C_1-C_6)$alkoxy$(C_1-C_6)$alkyl. One skilled in the art will appreciate that each of the aforementioned Q embodiments can be combined with any of the aforementioned embodiments (e.g., tetrahydropyrans, tetrahydrothiopyrans, hydroxy-tetrahydrothiopyrans, tetrahydropyran-ethers, etc.).

Preferred compounds of the invention wherein Q contains two or more pendant rings, are those compounds wherein the rings are each connected in a para orientation, more preferably wherein the ring connected to the nucleus (i.e. the "X" containing ring) through the $SO_2$— group is substituted in the para orientation.

Other preferred compounds of the present invention are those wherein Q is $(C_6-C_{10})$ aryl$(C_1-C_6)$alkoxy$(C_6-C_{10})$ aryl, $(C_6-C_{10})$aryl$(C_1-C_6)$alkoxy$(C_1-C_9)$heteroaryl, $(C_1-C_9)$ heteroaryl$(C_1-C_6)$alkoxy$(C_6-C_{10})$aryl, $(C_1-C_9)$ heteroaryl$(C_1-C_9)$alkoxy$(C_1-C_9)$heteroaryl, optionally substituted by one or more, preferably one to three substituents per ring, most preferably one to three substituents on the terminal ring, wherein said substituent is selected from halo, $(C_1-C_6)$alkyl, $(C_1-C_6)$alkoxy or perfluoro$(C_1-C_3)$alkyl.

Other preferred compounds of the present invention are those wherein Q is piperidinyl, piperazinyl, pyrrolidino, morpholinyl, thiomorpholinyl, $(C_6-C_{10})$arylpiperidinyl, $(C_1-C_9)$ heteroarylpiperidinyl, $(C_6-C_{10})$aryloxypiperidinyl, $(C_1-C_9)$heteroaryloxypiperidinyl, $(C_1-C_{10})$ aryl$(C_1-C_6)$ alkoxypiperidinyl, $(C_1-C_9)$heteroaryl$(C_1-C_9)$ alkoxypiperidinyl, $(C_6-C_{10})$ arylpiperazinyl or $(C_1-C_9)$ heteroarylpiperazinyl optionally substituted by one or more, preferably one to three substituents per ring, most preferably one to three substituents on the terminal ring, wherein said substituent is selected from halo, $(C_1-C_6)$alkyl, $(C_1-C_9)$ alkoxy or perfluoro$(C_1-C_3)$alkyl.

Other preferred compounds of the present invention are those wherein Q is $(C_6-C_{10})$ arylmethoxy$(C_6-C_{10})$aryl, $(C_6-C_{10})$arylmethoxy$(C_2-C_9)$heteroaryl, $(C_2-C_9)$ heteroarylmethoxy$(C_6-C_{10})$aryl or $(C_2-C_9)$ heteroarylmethoxy$(C_2-C_9)$heteroaryl optionally substituted by one or more, preferably one to three substituents per ring, most preferably one to three substituents on the terminal ring, wherein said substituent is selected from halo, $(C_1-C_6)$ alkyl, $(C_1-C_9)$alkoxy or perfluoro$(C_1-C_3)$alkyl.

More preferred compounds of the invention are those wherein Q is optionally substituted $(C_6-C_{10})$ arylmethoxyphenyl, $(C_6-C_{10})$arylmethoxypyridyl, $(C_6-C_{10})$ arylmethoxyfuryl, $(C_6-C_{10})$arylmethoxypyroyl, $(C_6-C_{10})$ arylmethoxythienyl, $(C_6-C_{10})$arylmethoxyisothiazolyl, $(C_6-C_{10})$arylmethoxyimidazolyl, $(C_6-C_{10})$ arylmethoxypyrazinyl, $(C_1-C_{10})$arylmethoxypyrimidyl, ($C_6$–$C_{10}$) arylmethoxyquinolyl, ($C_6$–$C_{10}$) arylmethoxypyrazolyl, ($C_6$–$C_{10}$)arylmethoxyisoxazolyl, ($C_6$–$C_{10}$) arylmethoxythiazolyl, ($C_6$–$C_{10}$) arylmethoxyoxazolyl, pyridylmethoxyphenyl, furylmethoxyphenyl, pyrroylmethoxyphenyl, thienylmethoxyphenyl, isothiazolylmethoxyphenyl, imidazolylmethoxyphenyl, benzimidazolylmethoxyphenyl, tetrazolylmethoxyphenyl, pyrazinylmethoxyphenyl, pyrimidylmethoxyphenyl, quinolylmethoxyphenyl, isoquinolylmethoxyphenyl, benzofurylmethoxyphenyl, isobenzofurylmethoxyphenyl, benzothienylmethoxyphenyl, pyrazolylmethoxyphenyl, indolylmethoxyphenyl, isoindolylmethoxyphenyl, purinylmethoxyphenyl, carbazolylmethoxyphenyl, isoxazolylmethoxyphenyl, thiazolylmethoxyphenyl, oxazolylmethoxyphenyl, benzthiazolylmethoxyphenyl, benzoxazolylmethoxyphenyl, pyridylmethoxypyridyl, pyridylmethoxyfuryl, pyridylmethoxypyroyl, pyridylmethoxythienyl, pyridylmethoxyisothiazolyl, pyridylmethoxyimidazolyl, pyridylmethoxypyrazinyl, pyridylmethoxypyrimidyl, pyridylmethoxyquinolyl, pyridylmethoxypyrazolyl, pyridylmethoxyisoxazolyl, pyridylmethoxythiazolyl, pyridylmethoxyoxazolyl, furylmethoxypyridyl, furylmethoxyfuryl, furylmethoxypyroyl, furylmethoxythienyl, furylmethoxyisothiazolyl, furylmethoxyimidazolyl, furylmethoxypyrazinyl, furylmethoxypyrimidyl, furylmethoxyquinolyl, furylmethoxypyrazolyl, furylmethoxyisoxazolyl, furylmethoxythiazolyl, furylmethoxyoxazolyl, pyrroylmethoxypyridyl, pyrroylmethoxyfuryl, pyrroylmethoxypyroyl, pyrroylmethoxythienyl, pyrroylmethoxyisothiazolyl, pyrroylmethoxyimidazolyl, pyrroylmethoxypyrazinyl, pyrroylmethoxypyrimidyl, pyrroylmethoxyquinolyl, pyrroylmethoxypyrazolyl, pyrroylmethoxyisoxazolyl, pyrroylmethoxythiazolyl, pyrroylmethoxyoxazolyl, thienylmethoxypyridyl, thienylmethoxyfuryl, thienylmethoxypyroyl, thienylmethoxythienyl, thienylmethoxyisothiazolyl, thienylmethoxyimidazolyl, thienylmethoxypyrazinyl, thienylmethoxypyrimidyl, thienylmethoxyquinolyl, thienylmethoxyisoxazolyl, thienylmethoxythiazolyl, thienylmethoxyoxazolyl, pyrazinylmethoxypyridyl, pyrazinylmethoxyfuryl, pyrazinylmethoxypyroyl, pyrazinylmethoxythienyl, pyrazinylmethoxyisothiazolyl, pyrazinylmethoxyimidazolyl, pyrazinylmethoxypyrazinyl, pyrazinylmethoxypyrimidyl, pyrazinylmethoxyquinolyl, pyrazinylmethoxyisoxazolyl, pyrazinylmethoxythiazolyl, pyrazinylmethoxyoxazolyl, pyrimidylmethoxypyridyl, pyrimidylmethoxyfuryl, pyrimidylmethoxypyroyl, pyrimidylmethoxythienyl, pyrimidylmethoxyisothiazolyl, pyrimidylmethoxyimidazolyl, pyrimidylmethoxypyrazinyl, pyrimidylmethoxypyrimidyl, pyrimidylmethoxyquinolyl, pyrimidylmethoxyisoxazolyl, pyrimidylmethoxythiazolyl, pyrimidylmethoxyoxazolyl, thiazolylmethoxypyridyl, thiazolylmethoxyfuryl, thiazolylmethoxypyroyl, thiazolylmethoxythienyl, thiazolylmethoxyisothiazolyl, thiazolylmethoxyimidazolyl, thiazolylmethoxypyrazinyl, thiazolylmethoxypyrimidyl, thiazolylmethoxyquinolyl, thiazolylmethoxyisoxazolyl, thiazolylmethoxythiazolyl, thiazolylmethoxyoxazolyl, and oxazolylmethoxypyridyl, oxazolylmethoxyfuryl, oxazolylmethoxypyroyl, oxazolylmethoxythienyl, oxazolylmethoxyisothiazolyl, oxazolylmethoxyimidazolyl, oxazoiylmethoxypyrazinyl, oxazolylmethoxypyrimidyl, oxazolylmethoxyquinolyl, oxazolylmethoxyisoxazolyl, oxazolylmethoxythiazolyl or oxazolylmethoxyoxazolyl.

More preferred compounds of the invention are those wherein Q is optionally substituted ($C_6$–$C_{10}$) arylmethoxyphenyl, ($C_6$–$C_{10}$)arylmethoxypyridyl, ($C_6$–$C_{10}$) arylmethoxyfuryl, ($C_6$–$C_{10}$)arylmethoxypyroyl, ($C_6$–$C_{10}$) arylmethoxythienyl, ($C_1$–$C_{10}$)arylmethoxyisothiazolyl, ($C_6$–$C_{10}$) arylmethoxyimidazolyl, ($C_6$–$C_{10}$) arylmethoxypyrazinyl, ($C_6$–$C_{10}$)arylmethoxypyrimidyl, ($C_6$–$C_{10}$) arylmethoxyquinolyl, ($C_6$–$C_{10}$) arylmethoxyisoxazolyl, ($C_6$–$C_{10}$)arylmethoxythiazolyl, ($C_6$–$C_{10}$) arylmethoxyoxazolyl, pyridylmethoxyphenyl, furylmethoxyphenyl, pyroylmethoxyphenyl, thienylmethoxyphenyl, isothiazolylmethoxyphenyl, imidazolylmethoxyphenyl, benzimidazolylmethoxyphenyl, tetrazolylmethoxyphenyl, pyrazinylmethoxyphenyl, pyrimidylmethoxyphenyl, quinolylmethoxyphenyl, isoquinolylmethoxyphenyl, benzofurylmethoxyphenyl, isobenzofurylmethoxyphenyl, benzothienylmethoxyphenyl, pyrazolylmethoxyphenyl, indolylmethoxyphenyl, isoindolylmethoxyphenyl, purinylmethoxyphenyl, carbazolylmethoxyphenyl, isoxazolylmethoxyphenyl, thiazolylmethoxyphenyl, oxazolylmethoxyphenyl, benzthiazolylmethoxyphenyl or benzoxazolylmethoxyphenyl.

More preferred compounds of the present invention are those wherein Q is optionally substituted ($C_6$–$C_{10}$) arylmethoxyphenyl, pyridylmethoxyphenyl, furylmethoxyphenyl, pyroylmethoxyphenyl, thienylmethoxyphenyl, isothiazolylmethoxyphenyl, imidazolylmethoxyphenyl, benzimidazolylmethoxyphenyl, tetrazolylmethoxyphenyl, pyrazinylmethoxyphenyl, pyrimidylmethoxyphenyl, quinolylmethoxyphenyl, isoquinolylmethoxyphenyl, benzofurylmethoxyphenyl, isobenzofurylmethoxyphenyl, benzothienylmethoxyphenyl, pyrazolylmethoxyphenyl, indolylmethoxyphenyl, isoindolylmethoxyphenyl, purinylmethoxyphenyl, carbazolylmethoxyphenyl, isoxazolylmethoxyphenyl, thiazolylmethoxyphenyl, oxazolylmethoxyphenyl, benzthiazolylmethoxyphenyl or benzoxazolylmethoxyphenyl.

More preferred compounds of the invention are those wherein Q is optionally substituted 4-(($C_6$–$C_{10}$) arylmethoxy)-phenyl, 4-(pyridylmethoxy)-phenyl, 4-(thienylmethoxy)-phenyl, 4-(pyrazinylmethoxy)-phenyl, 4-(pyrimidylmethoxy)-phenyl, 4-(pyridazinylmethoxy)-phenyl, 4-(thiazolylmethoxy)-phenyl, 4-(oxazolylmethoxy)-phenyl.

Most preferred compounds of the present invention are those wherein Q is 4-($C_6$–$C_{10}$) arylmethoxy)-phenyl optionally substituted by one or more, preferably one to three substituents per ring, most preferably one to three substituents on the terminal ring, wherein said substituents are independently selected from halo, ($C_1$–$C_6$)alkyl, ($C_1$–$C_6$) alkoxy or perfluoro($C_1$–$C_3$)alkyl.

Other more preferred compounds of the present invention are those wherein Q is 4-(($C_6$–$C_{10}$) arylmethoxy)-($C_2$–$C_9$) heteroaryl optionally substituted by one or more, preferably one to three substituents per ring, most preferably one to three substituents on the terminal ring, wherein said substituents are independently selected from halo, ($C_1$–$C_6$) alkyl, ($C_1$–$C_6$)alkoxy or perfluoro($C_1$–$C_3$)alkyl.

Other more preferred compounds of the present invention are those wherein Q is 4-(($C_2$–$C_9$) heteroarylmethoxy)-phenyl optionally substituted by one or more, preferably one to three substituents per ring, most preferably one to three substituents on the terminal ring, wherein said substituents are independently selected from halo, $(C_1-C_6)$alkyl, $(C_1-C_9)$alkoxy or perfluoro$(C_1-C_3)$alkyl.

Other more preferred compounds of the present invention are those wherein Q is 4-(($C_2-C_9$) heteroarylmethoxy)-$(C_2-C_9)$heteroaryl optionally substituted by one or more, preferably one to three substituents per ring, most preferably one to three substituents on the terminal ring, wherein said substituents are independently selected from halo, $(C_1-C_6)$ alkyl, $(C_1-C_6)$ alkoxy or perfluoro$(C_1-C_3)$alkyl.

Other preferred compounds of the present invention are those wherein $R^1$, $R^2$, $R^5$ and $R^6$ are each independently selected from the group consisting of hydrogen, $(C_1-C_6)$ alkyl, $(C_2-C_6)$ alkenyl, $(C_2-C_6)$alkynyl, perfluoro$(C_1-C_6)$ alkyl, $(C_6-C_{10})$aryl, $(C_1-C_9)$heteroaryl, $(C_3-C_6)$ cycloalkyl, $(C_3-C_{10})$heterocyclic, $(C_1-C_6)$alkyl(C=O)—, $(C_1-C_6)$ alkoxy-(C=O)—, —CO$_2$H, H$_2$N—(C=O)—, $(C_1-C_6)$ alkyl-NH—(C=O)—, and $[(C_1-C_6)$alkyl$]_2$—N—(C=O)—; wherein each of said $(C_1-C_{10})$ alkyl groups are each independently optionally substituted by one to three groups selected from halo, trifluoromethyl, hydroxy, amino, $(C_1-C_6)$alkoxy, $(C_6-C_{10})$aryl, $(C_1-C_9)$heteroaryl, $(C_3-C_6)$ cycloalkyl, $(C_3-C_{10})$heterocyclic, $(C_1-C_6)$alkyl-(C=O)—NH—, $(C_1-C_6)$alkyl-(C=O)—O—, $(C_1-C_6)$ alkylamino or $((C_1-C_6)$alkyl$)_2$amino; more preferably wherein $R^1$, $R^2$, $R^5$ and $R^6$ are each independently selected from the group consisting of hydrogen, $(C_1-C_9)$alkyl, $(C_2-C_6)$alkenyl, perfluoro$(C_1-C_6)$alkyl, $(C_1-C_6)$alkyl(C=O)—, $(C_1-C_6)$ alkoxy-(C=O)—, $(C_1-C_6)$alkyl-NH—(C=O)—, and $[(C_1-C_6)$alkyl$]_2$-N—(C=O)—; wherein each of said $(C_1-C_6)$alkyl groups are each independently optionally substituted by one to three groups selected from halo, trifluoromethyl, hydroxy, amino, $(C_1-C_6)$alkoxy, $(C_6-C_{10})$ aryl, $(C_1-C_9)$heteroaryl, $(C_3-C_6)$cycloalkyl, $(C_3-C_9)$ heterocyclic, $(C_1-C_6)$alkyl-(C=O)—NH—, $(C_1-C_6)$alkyl-(C=O)—O—, $(C_1-C_6)$alkylamino or $((C_1-C_9)$alkyl$)_2$ amino; more preferably wherein $R^1$, $R^2$, $R^5$ and $R^6$ are each independently selected from the group consisting of hydrogen, $(C_1-C_6)$alkyl and $(C_2-C_6)$alkenyl; wherein said $(C_1-C_6)$alkyl groups are each independently optionally substituted by one to three groups (more preferably one to two groups) selected from halo, hydroxy, amino, $(C_1-C_6)$alkoxy or $(C_6-C_{10})$aryl; most preferably wherein $R^1$, $R^2$, $R^5$ and $R^6$ are each independently selected from the group consisting of hydrogen or $(C_1-C_4)$alkyl.

Other preferred compounds of the present invention are those wherein $R^7$ and $R^8$ are each independently selected from the group consisting of hydrogen, hydroxy, halo, $(C_1-C_6)$ alkyl, $(C_2-C_6)$alkenyl, $(C_2-C_6)$alkynyl, amino, $(C_1-C_6)$alkylamino, $[(C_1-C_6)$alkyl$]_2$amino, $(C_1-C_6)$ alkoxy, perfluoro$(C_1-C_6)$alkyl, perfluoro$(C_1-C_6)$alkoxy, $(C_3-C_6)$ cycloalkyl, $(C_6-C_{10})$aryl, $(C_3-C_{10})$ heterocyclic, $(C_1-C_9)$ heteroaryl, $(C_1-C_6)$alkyl (C=O)—, $(C_1-C_6)$alkyl(C=O)—NH—, $(C_1-C_6)$ alkyl(C=O)—O—, $(C_1-C_6)$alkoxy-(C=O)—, —CO$_2$H, H$_2$N—(C=O)—, $(C_1-C_6)$alkyl-NH—(C=O)—, and $[(C_1-C_6)$alkyl$]_2$-N—(C=O)—; more preferably wherein $R^7$ and $R^8$ are each independently selected from the group consisting of hydrogen, hydroxy, halo, $(C_1-C_6)$alkyl, $(C_2-C_6)$alkenyl, amino, $(C_1-C_6)$ alkylamino, $[(C_1-C_6)$alkyl$]_2$amino, $(C_1-C_6)$alkoxy, perfluoro$(C_1-C_6)$alkyl and perfluoro$(C_1-C_6)$ alkoxy; most preferably preferably wherein $R^7$ and $R^8$ are each independently selected from the group consisting of hydrogen, hydroxy, $(C_1-C_4)$alkyl, amino, $(C_1-C_4)$alkoxy, trifluoromethyl and trifluoromethoxy.

Other preferred compounds of the present invention are those wherein at least one of $R^1$ and $R^2$, $R^5$ and $R^6$ or $R^7$ and $R^8$ are taken together to form a carbonyl group or an optionally substituted $(C_3-C_6)$cycloalkyl ring; more preferably wherein one of $R^1$ and $R^2$, $R^5$ and $R^6$ or $R^7$ and $R^8$ is taken together to form a carbonyl group.

Other compounds of the present invention are those wherein one of $R^5$ and $R^7$, $R^5$ and $R^{8, \, R6}$ and $R^7$ or $R^6$ and $R^8$ are taken together to form an optionally substituted $(C_4-C_6)$cycloalkyl ring, preferably cis fused.

Other more preferred compounds of the present invention are those wherein $R^1$ or $R^2$ are hydrogen.

Other more preferred compounds of the present invention are those wherein at least one of $R^1$ or $R^2$ is other than hydrogen.

Other more preferred compounds of the present invention are those wherein at least one of $R^1$–$R^6$ is $(C_1-C_6)$alkyl, more preferably methyl or ethyl.

Other compounds of the present invention are those wherein at least one of $R^1$–$R^6$ is other than hydrogen or $(C_1-C_6)$alkyl.

Other more preferred compounds of the present invention are those wherein at least one of $R^1$–$R^2$ is $(C_1-C_6)$alkyl, preferably methyl or ethyl.

Other more preferred compounds of the present invention are those wherein $R^1$ is hydrogen or $(C_1-C_6)$alkyl, preferably hydrogen, methyl or ethyl.

Other more preferred compounds of the present invention are those wherein $R^2$ is hydrogen or $(C_1-C_6)$alkyl, preferably hydrogen, methyl or ethyl.

Other more preferred compounds of the present invention are those wherein $R^3$ is hydrogen or $(C_1-C_9)$alkyl, preferably hydrogen, methyl or ethyl.

Other more preferred compounds of the present invention are those wherein $R^5$ is hydrogen or $(C_1-C_6)$alkyl, preferably hydrogen, methyl or ethyl.

Other more preferred compounds of the present invention are those wherein $R^6$ is hydrogen or $(C_1-C_6)$alkyl, preferably hydrogen, methyl or ethyl.

Other more preferred compounds of the present invention are those wherein $R^7$ is hydrogen or $(C_1-C_9)$alkyl, preferably hydrogen, methyl or ethyl.

Other more preferred compounds of the present invention are those wherein $R^8$ is $(C_1-C_6)$alkyl, preferably methyl or ethyl.

Other more preferred compounds of the present invention are those wherein $R^4$ is hydrogen.

Other more preferred compounds of the present invention are those wherein $R^4$ and $R^2$ are each $(C_1-C_6)$alkyl, preferably methyl or ethyl.

Other more preferred compounds of the present invention are those wherein $R^5$ and $R^6$ are each $(C_1-C_6)$alkyl, preferably methyl or ethyl.

Other more preferred compounds of the present invention are those wherein $R^7$ and $R^8$ are each $(C_1-C_6)$alkyl, preferably methyl or ethyl.

Most preferred compounds of the invention are those wherein $R^1$–$R^8$ are each hydrogen, or $R^1$ or $R^2$ are each methyl or ethyl.

Specific most preferred compounds of the present invention are selected from the group consisting of:
- 4-[4-(4-Fluoro-2-methyl-benzyloxy)-benzenesulfonyl]-3-hydroxy-tetrahydro-pyran-3-carboxylic acid hydroxyamide;
- 4-[4-(3-Chloro-benzyloxy)-benzenesulfonyl]-3-hydroxy-tetrahydro-pyran-3-carboxylic acid hydroxyamide;
- 4-[4-(4-Chloro-benzyloxy)-benzenesulfonyl]-3-hydroxy-tetrahydro-pyran-3-carboxylic acid hydroxyamide;
- 4-[4-(2-Chloro-benzyloxy)-benzenesulfonyl]-3-hydroxy-tetrahydro-pyran-3-carboxylic acid hydroxyamide;

4-[4-(3-Fluoro-benzyloxy)-benzenesulfonyl]-3-hydroxy-tetrahydro-pyran-3-carboxylic acid hydroxyamide;

3-Hydroxy-4-[4-(2-methyl-benzyloxy)-benzenesulfonyl]-tetrahydro-pyran-3-carboxylic acid hydroxyamide; and 4-[4-(4-Fluoro-2-methyl-benzyloxy)-benzenesulfonyl]-3-hydroxy-tetrahydro-pyran-3-carboxylic acid hydroxyamide.

Other specific pyran compounds of the invention are:

4-(2'-Chloro-biphenyl-4-sulfonyl)-3-hydroxy-tetrahydro-pyran-3-carboxylic acid hydroxyamide, 4-(3'-Chloro-biphenyl-4-sulfonyl)-3-hydroxy-tetrahydro-pyran-3-carboxylic acid hydroxyamide, 4-(4'-Chloro-biphenyl-4-sulfonyl)-3-hydroxy-tetrahydro-pyran-3-carboxylic acid hydroxyamide, 3-Hydroxy-4-(4'-methyl-biphenyl-4-sulfonyl)-tetrahydro-pyran-3-carboxylic acid hydroxyamide, 3-Hydroxy-4-(3'-methyl-biphenyl-4-sulfonyl)-tetrahydro-pyran-3-carboxylic acid hydroxyamide, 3-Hydroxy-4-(2'-methyl-biphenyl-4-sulfonyl)-tetrahydro-pyran-3-carboxylic acid hydroxyamide, 4-(2'-Fluoro-biphenyl-4-sulfonyl)-3-hydroxy-tetrahydro-pyran-3-carboxylic acid hydroxyamide, 4-(3'-Fluoro-biphenyl-4-sulfonyl)-3-hydroxy-tetrahydro-pyran-3-carboxylic acid hydroxyamide, 4-(4'-Fluoro-biphenyl-4-sulfonyl)-3-hydroxy-tetrahydro-pyran-3-carboxylic acid hydroxyamide, 3-Hydroxy-4-(4-pyridin-4-yl-benzenesulfonyl)-tetrahydro-pyran-3-carboxylic acid hydroxyamide, 3-Hydroxy-4-(4-pyridin-3-yl-benzenesulfonyl)-tetrahydro-pyran-3-carboxylic acid hydroxyamide, 3-Hydroxy-4-(4-pyridin-2-yl-benzenesulfonyl)-tetrahydro-pyran-3-carboxylic acid hydroxyamide, 3-Hydroxy-4-(4'-methoxy-biphenyl-4-sulfonyl)-tetrahydro-pyran-3-carboxylic acid hydroxyamide, 3-Hydroxy-4-(3'-methoxy-biphenyl-4-sulfonyl)-tetrahydro-pyran-3-carboxylic acid hydroxyamide, 3-Hydroxy-4-(2'-methoxy-biphenyl-4-sulfonyl)-tetrahydro-pyran-3-carboxylic acid hydroxyamide, 4-(Biphenyl-4-sulfonyl)-3-hydroxy-tetrahydro-pyran-3-carboxylic acid hydroxyamide, 3-Hydroxy-4-(4-phenyl-piperidine-1-sulfonyl)-tetrahydro-pyran-3-carboxylic acid hydroxyamide, 4-[4-(2-Chloro-phenyl)-piperidine-1-sulfonyl]-3-hydroxy-tetrahydro-pyran-3-carboxylic acid hydroxyamide, 4-[4-(3-Chloro-phenyl)-piperidine-1-sulfonyl]-3-hydroxy-tetrahydro-pyran-3-carboxylic acid hydroxyamide, 4-[4-(4-Chloro-phenyl)-piperidine-1-sulfonyl]-3-hydroxy-tetrahydro-pyran-3-carboxylic acid hydroxyamide, 3-Hydroxy-4-(4-o-tolyl-piperidine-1-sulfonyl)-tetrahydro-pyran-3-carboxylic acid hydroxyamide, 3-Hydroxy-4-(4-m-tolyl-piperidine-1-sulfonyl)-tetrahydro-pyran-3-carboxylic acid hydroxyamide, 3-Hydroxy-4-(4-p-tolyl-piperidine-1-sulfonyl)-tetrahydro-pyran-3-carboxylic acid hydroxyamide, 4-[4-(2-Fluoro-phenyl)-piperidine-1-sulfonyl]-3-hydroxy-tetrahydro-pyran-3-carboxylic acid hydroxyamide, 4-[4-(3-Fluoro-phenyl)-piperidine-1-sulfonyl]-3-hydroxy-tetrahydro-pyran-3-carboxylic acid hydroxyamide, 4-[4-(4-Fluoro-phenyl)-piperidine-1-sulfonyl]-3-hydroxy-tetrahydro-pyran-3-carboxylic acid hydroxyamide, 3-Hydroxy-4-[4-(2-methoxy-phenyl)-piperidine-1-sulfonyl]-tetrahydro-pyran-3-carboxylic acid hydroxyamide, 3-Hydroxy-4-[4-(4-methoxy-phenyl)-piperidine-1-sulfonyl]-tetrahydro-pyran-3-carboxylic acid hydroxyamide, 3-Hydroxy-4-[4-(3-methoxy-phenyl)-piperidine-1-sulfonyl]-tetrahydro-pyran-3-carboxylic acid hydroxyamide, 3-Hydroxy-4-(3',4',5',6'-tetrahydro-2'H-[2,4']bipyridinyl-1'-sulfonyl)-tetrahydro-pyran-3-carboxylic acid hydroxyamide, 3-Hydroxy-4-(3',4',5',6'-tetrahydro-2'H-[3,4']bipyridinyl-1'-sulfonyl)-tetrahydro-pyran-3-carboxylic acid hydroxyamide, 3-Hydroxy-4-(3,4,5,6-tetrahydro-2H-[4,4']bipyridinyl-1-sulfonyl)-tetrahydro-pyran-3-carboxylic acid hydroxyamide, 4-(2',6'-Dimethyl-3,4,5,6-tetrahydro-2H-[4,4']bipyridinyl-1-sulfonyl)-3-hydroxy-tetrahydro-pyran-3-carboxylic acid hydroxyamide, 4-[4-(2,6-Dimethyl-pyridin-4-yl)-benzenesulfonyl]-3-hydroxy-tetrahydro-pyran-3-carboxylic acid hydroxyamide, 3-Hydroxy-4-(4-phenoxy-benzenesulfonyl)-tetrahydro-pyran-3-carboxylic acid hydroxyamide, 4-[4-(2-Chloro-phenoxy)-benzenesulfonyl]-3-hydroxy-tetrahydro-pyran-3-carboxylic acid hydroxyamide, 4-[4-(3-Chloro-phenoxy)-benzenesulfonyl]-3-hydroxy-tetrahydro-pyran-3-carboxylic acid hydroxyamide, 4-[4-(4-Chloro-phenoxy)-benzenesulfonyl]-3-hydroxy-tetrahydro-pyran-3-carboxylic acid hydroxyamide, 3-Hydroxy-4-(4-o-tolyloxy-benzenesulfonyl)-tetrahydro-pyran-3-carboxylic acid hydroxyamide, 3-Hydroxy-4-(4-m-tolyloxy-benzenesulfonyl)-tetrahydro-pyran-3-carboxylic acid hydroxyamide, 3-Hydroxy-4-(4-p-tolyloxy-benzenesulfonyl)-tetrahydro-pyran-3-carboxylic acid hydroxyamide, 4-[4-(2-Fluoro-phenoxy)-benzenesulfonyl]-3-hydroxy-tetrahydro-pyran-3-carboxylic acid hydroxyamide, 4-[4-(3-Fluoro-phenoxy)-benzenesulfonyl]-3-hydroxy-tetrahydro-pyran-3-carboxylic acid hydroxyamide, 4-[4-(4-Fluoro-phenoxy)-benzenesulfonyl]-3-hydroxy-tetrahydro-pyran-3-carboxylic acid hydroxyamide, 3-Hydroxy-4-[4-(2-methoxy-phenoxy)-benzenesulfonyl]-tetrahydro-pyran-3-carboxylic acid hydroxyamide, 3-Hydroxy-4-[4-(3-methoxy-phenoxy)-benzenesulfonyl]-tetrahydro-pyran-3-carboxylic acid hydroxyamide, 3-Hydroxy-4-[4-(4-methoxy-phenoxy)-benzenesulfonyl]-tetrahydro-pyran-3-carboxylic acid hydroxyamide, 3-Hydroxy-4-[4-(pyridin-2-yloxy)-benzenesulfonyl]-tetrahydro-pyran-3-carboxylic acid hydroxyamide, 3-Hydroxy-4-[4-(pyridin-3-yloxy)-benzenesulfonyl]-tetrahydro-pyran-3-carboxylic acid hydroxyamide, 3-Hydroxy-4-[4-(pyridin-4-yloxy)-benzenesulfonyl]-tetrahydro-pyran-3-carboxylic acid hydroxyamide, 4-[4-(2,6-Dimethyl-pyridin-4-yloxy)-benzenesulfonyl]-3-hydroxy-tetrahydro-pyran-3-carboxylic acid hydroxyamide, 4-[4-(2,6-Dimethyl-pyridin-4-yloxy)-piperidine-1-sulfonyl]-3-hydroxy-tetrahydro-pyran-3-carboxylic acid hydroxyamide,
3-Hydroxy-4-[4-(pyridin-4-yloxy)-piperidine-1-sulfonyl]-tetrahydro-pyran-3-carboxylic acid hydroxyamide,
3-Hydroxy-4-[4-(pyridin-3-yloxy)-piperidine-1-sulfonyl]-tetrahydro-pyran-3-carboxylic acid hydroxyamide,
3-Hydroxy-4-[4-(pyridin-2-yloxy)-piperidine-1-sulfonyl]-tetrahydro-pyran-3-carboxylic acid hydroxyamide,
4-[4-(2-Chloro-phenoxy)-piperidine-1-sulfonyl]-3-hydroxy-tetrahydro-pyran-3-carboxylic acid hydroxyamide,
4-[4-(3-Chloro-phenoxy)-piperidine-1-sulfonyl]-3-hydroxy-tetrahydro-pyran-3-carboxylic acid hydroxyamide,
4-[4-(4-Chloro-phenoxy)-piperidine-1-sulfonyl]-3-hydroxy-tetrahydro-pyran-3-carboxylic acid hydroxyamide,
4-[4-(2-Fluoro-phenoxy)-piperidine-1-sulfonyl]-3-hydroxy-tetrahydro-pyran-3-carboxylic acid hydroxyamide,
4-[4-(3-Fluoro-phenoxy)-piperidine-1-sulfonyl]-3-hydroxy-tetrahydro-pyran-3-carboxylic acid hydroxyamide,
4-[4-(4-Fluoro-phenoxy)-piperidine-1-sulfonyl]-3-hydroxy-tetrahydro-pyran-3-carboxylic acid hydroxyamide,
3-Hydroxy-4-(4-o-tolyloxy-piperidine-1-sulfonyl)-tetrahydro-pyran-3-carboxylic acid hydroxyamide,
3-Hydroxy-4-(4-m-tolyloxy-piperidine-1-sulfonyl)-tetrahydro-pyran-3-carboxylic acid hydroxyamide,
3-Hydroxy-4-(4-p-tolyloxy-piperidine-1-sulfonyl)-tetrahydro-pyran-3-carboxylic acid hydroxyamide,
3-Hydroxy-4-[4-(2-methoxy-phenoxy)-piperidine-1-sulfonyl]-tetrahydro-pyran-3-carboxylic acid hydroxyamide,
3-Hydroxy-4-[4-(3-methoxy-phenoxy)-piperidine-1-sulfonyl]-tetrahydro-pyran-3-carboxylic acid hydroxyamide,
3-Hydroxy-4-[4-(4-methoxy-phenoxy)-piperidine-1-sulfonyl]-tetrahydro-pyran-3-carboxylic acid hydroxyamide,
3-Hydroxy-4-(4-phenoxy-piperidine-1-sulfonyl)-tetrahydro-pyran-3-carboxylic acid hydroxyamide,
4-(4-Benzyloxy-piperidine-1-sulfonyl)-3-hydroxy-tetrahydro-pyran-3-carboxylic acid hydroxyamide,
4-[4-(2-Chloro-benzyloxy)-piperidine-1-sulfonyl]-3-hydroxy-tetrahydro-pyran-3-carboxylic acid hydroxyamide,
4-[4-(3-Chloro-benzyloxy)-piperidine-1-sulfonyl]-3-hydroxy-tetrahydro-pyran-3-carboxylic acid hydroxyamide,
4-[4-(4-Chloro-benzyloxy)-piperidine-1-sulfonyl]-3-hydroxy-tetrahydro-pyran-3-carboxylic acid hydroxyamide,
4-[4-(2-Fluoro-benzyloxy)-piperidine-1-sulfonyl]-3-hydroxy-tetrahydro-pyran-3-carboxylic acid hydroxyamide,
4-[4-(3-Fluoro-benzyloxy)-piperidine-1-sulfonyl]-3-hydroxy-tetrahydro-pyran-3-carboxylic acid hydroxyamide,
4-[4-(4-Fluoro-benzyloxy)-piperidine-1-sulfonyl]-3-hydroxy-tetrahydro-pyran-3-carboxylic acid hydroxyamide,
3-Hydroxy-4-[4-(2-methyl-benzyloxy)-piperidine-1-sulfonyl]-tetrahydro-pyran-3-carboxylic acid hydroxyamide,
3-Hydroxy-4-[4-(3-methyl-benzyloxy)-piperidine-1-sulfonyl]-tetrahydro-pyran-3-carboxylic acid hydroxyamide,
3-Hydroxy-4-[4-(4-methyl-benzyloxy)-piperidine-1-sulfonyl]-tetrahydro-pyran-3-carboxylic acid hydroxyamide,
3-Hydroxy-4-[4-(2-methoxy-benzyloxy)-piperidine-1-sulfonyl]-tetrahydro-pyran-3-carboxylic acid hydroxyamide,
3-Hydroxy-4-[4-(3-methoxy-benzyloxy)-piperidine-1-sulfonyl]-tetrahydro-pyran-3-carboxylic acid hydroxyamide,
3-Hydroxy-4-[4-(4-methoxy-benzyloxy)-piperidine-1-sulfonyl]-tetrahydro-pyran-3-carboxylic acid hydroxyamide,
3-Hydroxy-4-[4-(pyridin-2-ylmethoxy)-piperidine-1-sulfonyl]-tetrahydro-pyran-3-carboxylic acid hydroxyamide,
3-Hydroxy-4-[4-(pyridin-3-ylmethoxy)-piperidine-1-sulfonyl]-tetrahydro-pyran-3-carboxylic acid hydroxyamide,
3-Hydroxy-4-[4-(pyridin-4-ylmethoxy)-piperidine-1-sulfonyl]-tetrahydro-pyran-3-carboxylic acid hydroxyamide,
4-[4-(2,6-Dimethyl-pyridin-4-ylmethoxy)-piperidine-1-sulfonyl]-3-hydroxy-tetrahydro-pyran-3-carboxylic acid hydroxyamide,
4-[4-(2,6-Dimethyl-pyridin-4-ylmethoxy)-benzenesulfonyl]-3-hydroxy-tetrahydro-pyran-3-carboxylic acid hydroxyamide,
3-Hydroxy-4-[4-(pyridin-4-ylmethoxy)-benzenesulfonyl]-tetrahydro-pyran-3-carboxylic acid hydroxyamide,
3-Hydroxy-4-[4-(pyridin-3-ylmethoxy)-benzenesulfonyl]-tetrahydro-pyran-3-carboxylic acid hydroxyamide,
3-Hydroxy-4-[4-(pyridin-2-ylmethoxy)-benzenesulfonyl]-tetrahydro-pyran-3-carboxylic acid hydroxyamide,
4-(4-Benzyloxy-benzenesulfonyl)-3-hydroxy-tetrahydro-pyran-3-carboxylic acid hydroxyamide,
4-[4-(2-Chloro-benzyloxy)-benzenesulfonyl]-3-hydroxy-tetrahydro-pyran-3-carboxylic acid hydroxyamide,
4-[4-(3-Chloro-benzyloxy)-benzenesulfonyl]-3-hydroxy-tetrahydro-pyran-3-carboxylic acid hydroxyamide,
4-[4-(4-Chloro-benzyloxy)-benzenesulfonyl]-3-hydroxy-tetrahydro-pyran-3-carboxylic acid hydroxyamide,
4-[4-(2-Fluoro-benzyloxy)-benzenesulfonyl]-3-hydroxy-tetrahydro-pyran-3-carboxylic acid hydroxyamide,
4-[4-(3-Fluoro-benzyloxy)-benzenesulfonyl]-3-hydroxy-tetrahydro-pyran-3-carboxylic acid hydroxyamide,
4-[4-(4-Fluoro-benzyloxy)-benzenesulfonyl]-3-hydroxy-tetrahydro-pyran-3-carboxylic acid hydroxyamide,
3-Hydroxy-4-[4-(2-methyl-benzyloxy)-benzenesulfonyl]-tetrahydro-pyran-3-carboxylic acid hydroxyamide,
3-Hydroxy-4-[4-(3-methyl-benzyloxy)-benzenesulfonyl]-tetrahydro-pyran-3-carboxylic acid hydroxyamide, 3-Hydroxy-4-[4-(4-methyl-benzyloxy)-benzenesulfonyl]-tetrahydro-pyran-3-carboxylic acid hydroxyamide,
3-Hydroxy-4-[4-(2-methoxy-benzyloxy)-benzenesulfonyl]-tetrahydro-pyran-3-carboxylic acid hydroxyamide,
3-Hydroxy-4-[4-(3-methoxy-benzyloxy)-benzenesulfonyl]-tetrahydro-pyran-3-carboxylic acid hydroxyamide, and
3-Hydroxy-4-[4-(4-methoxy-benzyloxy)-benzenesulfonyl]-tetrahydro-pyran-3-carboxylic acid hydroxyamide.

Other specific piperidine compounds of the invention are:
4-(2'-Chloro-biphenyl4-sulfonyl)-3-hydroxy-piperidin-3-carboxylic acid hydroxyamide,
4-(3'-Chloro-biphenyl-4-suffonyl)-3-hydroxy-piperidin-3-carboxylic acid hydroxyamide,
4-(4'-Chloro-biphenyl-4-sulfonyl)-3-hydroxy-piperidin-3-carboxylic acid hydroxyamide,
3-Hydroxy-4-(4'-methyl-biphenyl)4-sulfonyl)-piperidin-3-carboxylic acid hydroxyamide,
3-Hydroxy-4-(3'-methyl-biphenyl-4-sulfonyl)-piperidin-3-carboxylic acid hydroxyamide,
3-Hydroxy-4-(2'-methyl-biphenyl-4-sulfonyl)-piperidin-3-carboxylic acid hydroxyamide,
4-(2'-Fluoro-biphenyl-4-sulfonyl)-3-hydroxy-piperidin-3-carboxylic acid hydroxyamide,
4-(3'-Fluoro-biphenyl-4-sulfonyl)-3-hydroxy-piperidin-3-carboxylic acid hydroxyamide,
4-(4'-Fluoro-biphenyl-4-sulfonyl)-3-hydroxy-piperidin-3-carboxylic acid hydroxyamide,
3-Hydroxy-4-(4-pyridin-4-yl-benzenesulfonyl)-piperidin-3-carboxylic acid hydroxyamide,
3-Hydroxy-4-(4-pyridin-4-yl-benzenesulfonyl)-piperidin-3-carboxylic acid hydroxyamide,
3-Hydroxy-4-(4-pyridin-2-yl-benzenesulfonyl)-piperidin-3-carboxylic acid hydroxyamide,
3-Hydroxy-4-(4'-methoxy-biphenyl-4-sulfonyl)-piperidin-3-carboxylic acid hydroxyamide,
3-Hydroxy-4-(3'-methoxy-biphenyl-4-sulfonyl)-piperidin-3-carboxylic acid hydroxyamide,
3-Hydroxy-4-(2'-methoxy-biphenyl-4-sulfonyl)-piperidin-3-carboxylic acid hydroxyamide,
4-(Biphenyl-4-sulfonyl)-3-hydroxy-piperidin-3-carboxylic acid hydroxyamide,
3-Hydroxy-4-(4-phenyl-piperidine-1-sulfonyl)-piperidin-3-carboxylic acid hydroxyamide,
4-[4-(2-Chloro-phenyl)-piperidine-1-sulfonyl]-3-hydroxy-piperidin-3-carboxylic acid hydroxyamide,
4-[4-(3-Chloro-phenyl)-piperidine-1-sulfonyl]-3-hydroxy-piperidin-3-carboxylic acid hydroxyamide,
4-[4-(4-Chloro-phenyl)-piperidine-1-sulfonyl]-3-hydroxy-piperidin-3-carboxylic acid hydroxyamide,
3-Hydroxy-4-(4-o-tolyl-piperidine-1-sulfonyl)-piperidin-3-carboxylic acid hydroxyamide,
3-Hydroxy-4-(4-m-tolyl-piperidine-1-sulfonyl)-piperidin-3-carboxylic acid hydroxyamide,
3-Hydroxy-4-(4-p-tolyl-piperidine-1-sulfonyl)-piperidin-3-carboxylic acid hydroxyamide,
4-[4-(2-Fluoro-phenyl)-piperidine-1-sulfonyl]-3-hydroxy-piperidin-3-carboxylic acid hydroxyamide,
4-[4-(3-Fluoro-phenyl)-piperidine-1-sulfonyl]-3-hydroxy-piperidin-3-carboxylic acid hydroxyamide,
4-[4-(4-Fluoro-phenyl)-piperidine-1-sulfonyl]-3-hydroxy-piperidin-3-carboxylic acid hydroxyamide,
3-Hydroxy-4-[4-(2-methoxy-phenyl)-piperidine-1-sulfonyl]-piperidin-3-carboxylic acid hydroxyamide,
3-Hydroxy-4-[4-(4-methoxy-phenyl)-piperidine-1-sulfonyl]-piperidin-3-carboxylic acid hydroxyamide,
3-Hydroxy-4-[4-(3-methoxy-phenyl)-piperidine-1-sulfonyl]-piperidin-3-carboxylic acid hydroxyamide,
3-Hydroxy-4-(3',4',5',6'-tetrahydro-2'H-[2,4']bipyridinyl-1'-sulfonyl)-piperidin-3-carboxylic acid hydroxyamide,
3-Hydroxy-4-(3',4',5',6'-tetrahydro-2'H-[3,4']bipyridinyl-1'-sulfonyl)-piperidin-3-carboxylic acid hydroxyamide,
3-Hydroxy-4-(3,4,5,6-tetrahydro-2H-[4,4']bipyridinyl-1-sulfonyl)-piperidin-3-carboxylic acid hydroxyamide,
4-(2',6'-Dimethyl-3,4,5,6-tetrahydro-2H-[4,4']bipyridinyl-1-sulfonyl)-3-hydroxy-piperidin-3-carboxylic acid hydroxyamide,
4-[4-(2,6-Dimethyl-pyridin-4-yl)-benzenesulfonyl]-3-hydroxy-piperidin-3-carboxylic acid hydroxyamide,
3-Hydroxy-4-(4-phenoxy-benzenesulfonyl)-piperidin-3-carboxylic acid hydroxyamide,
4-[4-(2-Chloro-phenoxy)-benzenesulfonyl]-3-hydroxy-piperidin-3-carboxylic acid hydroxyamide,
4-[4-(3-Chloro-phenoxy)-benzenesulfonyl]-3-hydroxy-piperidin-3-carboxylic acid hydroxyamide,
4-[4-(4-Chloro-phenoxy)-benzenesulfonyl]-3-hydroxy-piperidin-3-carboxylic acid hydroxyamide,
3-Hydroxy-4-(4-o-tolyloxy-benzenesulfonyl)-piperidin-3-carboxylic acid hydroxyamide,
3-Hydroxy-4-(4-m-tolyloxy-benzenesulfonyl)-piperidin-3-carboxylic acid hydroxyamide,
3-Hydroxy4-(4-p-tolyloxy-benzenesulfonyl)-piperidin-3-carboxylic acid hydroxyamide,
4-[4-(2-Fluoro-phenoxy)-benzenesulfonyl]-3-hydroxy-piperidin-3-carboxylic acid hydroxyamide,
4-[4-(3-Fluoro-phenoxy)-benzenesulfonyl]-3-hydroxy-piperidin-3-carboxylic acid hydroxyamide,
4-[4-(4-Fluoro-phenoxy)-benzenesulfonyl]-3-hydroxy-piperidin-3-carboxylic acid hydroxyamide,
3-Hydroxy-4-[4-(2-methoxy-phenoxy)-benzenesulfonyl]-piperidin-3-carboxylic acid hydroxyamide,
3-Hydroxy-4-[4-(3-methoxy-phenoxy)-benzenesulfonyl]-piperidin-3-carboxylic acid hydroxyamide,
3-Hydroxy-4-[4-(4-methoxy-phenoxy)-benzenesulfonyl]-piperidin-3-carboxylic acid hydroxyamide,
3-Hydroxy-4-[4-(pyridin-2-yloxy)-benzenesulfonyl]-piperidin-3-carboxylic acid hydroxyamide,
3-Hydroxy-4-[4-(pyridin-3-yloxy)-benzenesulfonyl]-piperidin-3-carboxylic acid hydroxyamide,
3-Hydroxy-4-[4-(pyridin-4-yloxy)-benzenesulfonyl]-piperidin-3-carboxylic acid hydroxyamide,
4-[4-(2,6-Dimethyl-pyridin-4-yloxy)-benzenesulfonyl]-3-hydroxy-piperidin-3-carboxylic acid hydroxyamide,
4-[4-(2,6-Dimethyl-pyridin-4-yloxy)-piperidine-1-sulfonyl]-3-hydroxy-piperidin-3-carboxylic acid hydroxyamide,
3-Hydroxy-4-[4-(pyridin-4-yloxy)-piperidine-1-sulfonyl]-piperidin-3-carboxylic acid hydroxyamide, 3-Hydroxy-4-[4-(pyridin-3-yloxy)-piperidine-1-sulfonyl]-piperidin-3-carboxylic acid hydroxyamide,
3-Hydroxy-4-[4-(pyridin-2-yloxy)-piperidine-1-sulfonyl]-piperidin-3-carboxylic acid hydroxyamide,
4-[4-(2-Chloro-phenoxy)-piperidine-1-sulfonyl]-3-hydroxy-piperidin-3-carboxylic acid hydroxyamide,
4-[4-(3-Chloro-phenoxy)-piperidine-1-sulfonyl]-3-hydroxy-piperidin-3-carboxylic acid hydroxyamide,
4-[4-(4-Chloro-phenoxy)-piperidine-1-sulfonyl]-3-hydroxy-piperidin-3-carboxylic acid hydroxyamide,
4-[4-(2-Fluoro-phenoxy)-piperidine-1-sulfonyl]-3-hydroxy-piperidin-3-carboxylic acid hydroxyamide,
4-[4-(3-Fluoro-phenoxy)-piperidine-1-sulfonyl]-3-hydroxy-piperidin-3-carboxylic acid hydroxyamide,
4-[4-(4-Fluoro-phenoxy)-piperidine-1-sulfonyl]-3-hydroxy-piperidin-3-carboxylic acid hydroxyamide,
3-Hydroxy-4-(4-o-tolyloxy-piperidine-1-sulfonyl)-piperidin-3-carboxylic acid hydroxyamide,
3-Hydroxy-4-(4-m-tolyloxy-piperidine-1-sulfonyl)-piperidin-3-carboxylic acid hydroxyamide,
3-Hydroxy-4-(4-p-tolyloxy-piperidine-1-sulfonyl)-piperidin-3-carboxylic acid hydroxyamide,
3-Hydroxy-4-[4-(2-methoxy-phenoxy)-piperidine-1-sulfonyl]-piperidin-3-carboxylic acid hydroxyamide,
3-Hydroxy-4-[4-(3-methoxy-phenoxy)-piperidine-1-sulfonyl]-piperidin-3-carboxylic acid hydroxyamide,
3-Hydroxy-4-[4-(4-methoxy-phenoxy)-piperidine-1-sulfonyl]-piperidin-3-carboxylic acid hydroxyamide,
3-Hydroxy-4-(4-phenoxy-piperidine-1-sulfonyl)-piperidin-3-carboxylic acid hydroxyamide,
4-(4-Benzyloxy-piperidine-1-sulfonyl)-3-hydroxy-piperidin-3-carboxylic acid hydroxyamide,
4-[4-(2-Chloro-benzyloxy)-piperidine-1-sulfonyl]-3-hydroxy-piperidin-3-carboxylic acid hydroxyamide,
4-[4-(3-Chloro-benzyloxy)-piperidine-1-sulfonyl]-3-hydroxy-piperidin-3-carboxylic acid hydroxyamide,
4-[4-(4-Chloro-benzyloxy)-piperidine-1-sulfonyl]-3-hydroxy-piperidin-3-carboxylic acid hydroxyamide,
4-[4-(2-Fluoro-benzyloxy)-piperidine-1-sulfonyl]-3-hydroxy-piperidin-3-carboxylic acid hydroxyamide,
4-[4-(3-Fluoro-benzyloxy)-piperidine-1-sulfonyl]-3-hydroxy-piperidin-3-carboxylic acid hydroxyamide,
4-[4-(4-Fluoro-benzyloxy)-piperidine-1-sulfonyl]-3-hydroxy-piperidin-3-carboxylic acid hydroxyamide,
3-Hydroxy-4-[4-(2-methyl-benzyloxy)-piperidine-1-sulfonyl]-piperidin-3-carboxylic acid hydroxyamide,
3-Hydroxy-4-[4-(3-methyl-benzyloxy)-piperidine-1-sulfonyl]-piperidin-3-carboxylic acid hydroxyamide,
3-Hydroxy-4-[4-(4-methyl-benzyloxy)-piperidine-1-sulfonyl]-piperidin-3-carboxylic acid hydroxyamide,
3-Hydroxy-4-[4-(2-methoxy-benzyloxy)-piperidine-1-sulfonyl]-piperidin-3-carboxylic acid hydroxyamide,
3-Hydroxy-4-[4-(3-methoxy-benzyloxy)-piperidine-1-sulfonyl]-piperidin-3-carboxylic acid hydroxyamide,
3-Hydroxy-4-[4-(4-methoxy-benzyloxy)-piperidine-1-sulfonyl]-piperidin-3-carboxylic acid hydroxyamide,
3-Hydroxy-4-[4-(pyridin-2-ylmethoxy)-piperidine-1-sulfonyl]-piperidin-3-carboxylic acid hydroxyamide,
3-Hydroxy-4-[4-(pyridin-3-ylmethoxy)-piperidine-1-sulfonyl]-piperidin-3-carboxylic acid hydroxyamide,
3-Hydroxy-4-[4-(pyridin-4-ylmethoxy)-piperidine-1-sulfonyl]-piperidin-3-carboxylic acid hydroxyamide,
4-[4-(2,6-Dimethyl-pyridin-4-ylmethoxy)-piperidine-1-sulfonyl]-3-hydroxy-piperidin-3-carboxylic acid hydroxyamide,
4-[4-(2,6-Dimethyl-pyridin-4-yl methoxy)-benzenesulfonyl]-3-hydroxy-piperidin-3-carboxylic acid hydroxyamide,
3-Hydroxy-4-[4-(pyridin-4-ylmethoxy)-benzenesulfonyl]-piperidin-3-carboxylic acid hydroxyamide,
3-Hydroxy-4-[4-(pyridin-3-ylmethoxy)-benzenesulfonyl]-piperidin-3-carboxylic acid hydroxyamide,
3-Hydroxy-4-[4-(pyridin-2-ylmethoxy)-benzenesulfonyl]-piperidin-3-carboxylic acid hydroxyamide,
4-(4-Benzyloxy-benzenesulfonyl)-3-hydroxy-piperidin-3-carboxylic acid hydroxyamide,
4-[4-(2-Chloro-benzyloxy)-benzenesulfonyl]-3-hydroxy-piperidin-3-carboxylic acid hydroxyamide,
4-[4-(3-Chloro-benzyloxy)-benzenesulfonyl]-3-hydroxy-piperidin-3-carboxylic acid hydroxyamide,
4-[4-(4-Chloro-benzyloxy)-benzenesulfonyl]-3-hydroxy-piperidin-3-carboxylic acid hydroxyamide,
4-[4-(2-Fluoro-benzyloxy)-benzenesulfonyl]-3-hydroxy-piperidin-3-carboxylic acid hydroxyamide,
4-[4-(3-Fluoro-benzyloxy)-benzenesulfonyl]-3-hydroxy-piperidin-3-carboxylic acid hydroxyamide,
4-[4-(4-Fluoro-benzyloxy)-benzenesulfonyl]-3-hydroxy-piperidin-3-carboxylic acid hydroxyamide,
3-Hydroxy-4-[4-(2-methyl-benzyloxy)-benzenesulfonyl]-piperidin-3-carboxylic acid hydroxyamide,
3-Hydroxy-4-[4-(3-methyl-benzyloxy)-benzenesulfonyl]-piperidin-3-carboxylic acid hydroxyamide,
3-Hydroxy-4-[4-(4-methyl-benzyloxy)-benzenesulfonyl]-piperidin-3-carboxylic acid hydroxyamide,
3-Hydroxy-4-[4-(2-methoxy-benzyloxy)-benzenesulfonyl]-piperidin-3-carboxylic acid hydroxyamide,
3-Hydroxy-4-[4-(3-methoxy-benzyloxy)-benzenesulfonyl]-piperidin-3-carboxylic acid hydroxyamide, and
3-Hydroxy-4-[4-(4-methoxy-benzyloxy)-benzenesulfonyl]-piperidin-3-carboxylic acid hydroxyamide.

Other specific compounds of the invention are:
4-[4-(4-Fluoro-2-methyl-benzyloxy)-benzenesulfonyl]-3-hydroxy-2,2-dimethyl-tetrahydro-pyran-3-carboxylic acid hydroxyamide,
4-[4-(4-Fluoro-2-chloro-benzyloxy)-benzenesulfonyl]-3-hydroxy-2,2-dimethyl-tetrahydro-pyran-3-carboxylic acid hydroxyamide,
4-[4-(2,4-Dichloro-benzyloxy)-benzenesulfonyl]-3-hydroxy-2,2-dimethyl-tetrahydro-pyran-3-carboxylic acid hydroxyamide,
4-[4-(5-Fluoro-2-methyl-benzyloxy)-benzenesulfonyl]-3-hydroxy-2,2-dimethyl-tetrahydro-pyran-3-carboxylic acid hydroxyamide,
4-[4-(4-Fluoro-benzyloxy)-benzenesulfonyl]-3-hydroxy-2,2-dimethyl-tetrahydro-pyran-3-carboxylic acid hydroxyamide, 3-Amino-4-[4-(4-fluoro-2-methyl-benzyloxy)-benzenesulfonyl]-tetrahydro-pyran-3-carboxylic acid hydroxyamide, 3-Amino-4-[4-(4-fluoro-2-chloro-benzyloxy)-benzenesulfonyl]-tetrahydro-pyran-3-carboxylic acid hydroxyamide, 3-Amino-4-[4-(2,4-dichloro-benzyloxy)-benzenesulfonyl]-tetrahydro-pyran-3-carboxylic acid hydroxyamide, 3-Amino-4-[4-(5-fluoro-2-methyl-benzyloxy)-benzenesulfonyl]-tetrahydro-pyran-3-carboxylic acid hydroxyamide, 3-Amino-4-[4-(4-fluoro-benzyloxy)-benzenesulfonyl]-tetrahydro-pyran-3-carboxylic acid hydroxyamide, 4-[4-(4-Fluoro-2-methyl-benzyloxy)-benzenesulfonyl]-3-methoxy-tetrahydro-pyran-3-carboxylic acid hydroxyamide, 4-[4-(4-Fluoro-2-chloro-benzyloxy)-benzenesulfonyl]-3-methoxy-tetrahydro-pyran-3-carboxylic acid hydroxyamide, 4-[4-(2,4-Dichloro-benzyloxy)-benzenesulfonyl]-3-methoxy-tetrahydro-pyran-3-carboxylic acid hydroxyamide, 4-[4-(5-Fluoro-2-methyl-benzyloxy)-benzenesulfonyl]-3-methoxy-tetrahydro-pyran-3-carboxylic acid hydroxyamide, 4-[4-(4-Fluoro-benzyloxy)-benzenesulfonyl]-3-methoxy-tetrahydro-pyran-3-carboxylic acid hydroxyamide, 4-[4-(4-Fluoro-2-methyl-benzyloxy)-benzenesulfonyl]-3-ethoxy-tetrahydro-pyran-3-carboxylic acid hydroxyamide, 4-[4-(4-Fluoro-2-chloro-benzyloxy)-benzenesulfonyl]-3-ethoxy-tetrahydro-pyran-3-carboxylic acid hydroxyamide, 4-[4-(2,4-Dichloro-benzyloxy)-benzenesulfonyl]-3-ethoxy-tetrahydro-pyran-3-carboxylic acid hydroxyamide, 4-[4-(5-Fluoro-2-methyl-benzyloxy)-benzenesulfonyl]-3-ethoxy-tetrahydro-pyran-3-carboxylic acid hydroxyamide, 4-[4-(4-Fluoro-benzyloxy)-benzenesulfonyl]-3-ethoxy-tetrahydro-pyran-3-carboxylic acid hydroxyamide, 3-Amino-4-[4-(4-fluoro-2-methyl-benzyloxy)-benzenesulfonyl]-2,2-dimethyl-tetrahydro-pyran-3-carboxylic acid hydroxyamide, 3-Amino-4-[4-(4-fluoro-2-chloro-benzyloxy)-benzenesulfonyl]-2,2-dimethyl-tetrahydro-pyran-3-carboxylic acid hydroxyamide, 3-Amino-4-[4-(2,4-dichloro-benzyloxy)-benzenesulfonyl]-2,2-dimethyl-tetrahydro-pyran-3-carboxylic acid hydroxyamide, 3-Amino-4-[4-(5-fluoro-2-methyl-benzyloxy)-benzenesulfonyl]-2,2-dimethyl-tetrahydro-pyran-3-carboxylic acid hydroxyamide, 3-Amino-4-[4-(4-fluoro-benzyloxy)-benzenesulfonyl]-2,2-dimethyl-tetrahydro-pyran-3-carboxylic acid hydroxyamide, 4-[4-(4-Fluoro-2-methyl-benzyloxy)-benzenesulfonyl]-3-methyl-2,2-dimethyl-tetrahydro-pyran-3-carboxylic acid hydroxyamide, 4-[4-(4-Fluoro-2-chloro-benzyloxy)-benzenesulfonyl]-3-methyl-2,2-dimethyl-tetrahydro-pyran-3-carboxylic acid hydroxyamide, 4-[4-(2,4-Dichloro-benzyloxy)-benzenesulfonyl]-3-methyl-2,2-dimethyl-tetrahydro-pyran-3-carboxylic acid hydroxyamide, 4-[4-(5-Fluoro-2-methyl-benzyloxy)-benzenesulfonyl]-3-methyl-2,2-dimethyl-tetrahydro-pyran-3-carboxylic acid hydroxyamide, 4-[4-(4-Fluoro-benzyloxy)-benzenesulfonyl]-3-methyl-2,2-dimethyl-tetrahydro-pyran-3-carboxylic acid hydroxyamide, 4-[4-(4-Fluoro-2-methyl-benzyloxy)-benzenesulfonyl]-3-hydroxy-2-oxo-tetrahydro-pyran-3-carboxylic acid hydroxyamide, 4-[4-(4-Fluoro-2-chloro-benzyloxy)-benzenesulfonyl]-3-hydroxy-2-oxo-tetrahydro-pyran-3-carboxylic acid hydroxyamide, 4-[4-(2,4-Dichloro-benzyloxy)-benzenesulfonyl]-3-hydroxy-2-oxo-tetrahydro-pyran-3-carboxylic acid hydroxyamide, 4-[4-(5-Fluoro-2-methyl-benzyloxy)-benzenesulfonyl]-3-hydroxy-2-oxo-tetrahydro-pyran-3-carboxylic acid hydroxyamide, 4-[4-(4-Fluoro-benzyloxy)-benzenesulfonyl]-3-hydroxy-2-oxo-tetrahydro-pyran-3-carboxylic acid hydroxyamide, 4-[4-(4-Fluoro-2-methyl-benzyloxy)-benzenesulfonyl]-3-hydroxy-2,2-dimethyl-piperidin-3-carboxylic acid hydroxyamide, 4-[4-(4-Fluoro-2-chloro-benzyloxy)-benzenesulfonyl]-3-hydroxy-2,2-dimethyl-piperidin-3-carboxylic acid hydroxyamide, 4-[4-(2,4-Dichloro-benzyloxy)-benzenesulfonyl]-3-hydroxy-2,2-dimethyl-piperidin-3-carboxylic acid hydroxyamide, 4-[4-(5-Fluoro-2-methyl-benzyloxy)-benzenesulfonyl]-3-hydroxy-2,2-dimethyl-piperidin-3-carboxylic acid hydroxyamide, 4-[4-(4-Fluoro-benzyloxy)-benzenesulfonyl]-3-hydroxy-2,2-dimethyl-piperidin-3-carboxylic acid hydroxyamide, 3-Amino-4-[4-(4-fluoro-2-methyl-benzyloxy)-benzenesulfonyl]-piperidin-3-carboxylic acid hydroxyamide, 3-Amino-4-[4-(4-fluoro-2-chloro-benzyloxy)-benzenesulfonyl]-piperidin-3-carboxylic acid hydroxyamide, 3-Amino-4-[4-(2,4-dichloro-benzyloxy)-benzenesulfonyl]-piperidin-3-carboxylic acid hydroxyamide, 3-Amino-4-[4-(5-fluoro-2-methyl-benzyloxy)-benzenesulfonyl]-piperidin-3-carboxylic acid hydroxyamide, 3-Amino-4-[4-(4-fluoro-benzyloxy)-benzenesulfonyl]-piperidin-3-carboxylic acid hydroxyamide, 4-[4-(4-Fluoro-2-methyl-benzyloxy)-benzenesulfonyl]-3-methoxy-piperidin-3-carboxylic acid hydroxyamide, 4-[4-(4-Fluoro-2-chloro-benzyloxy)-benzenesulfonyl]-3-methoxy-piperidin-3-carboxylic acid hydroxyamide, 4-[4-(2,4-Dichloro-benzyloxy)-benzenesulfonyl]-3-methoxy-piperidin-3-carboxylic acid hydroxyamide, 4-[4-(5-Fluoro-2-methyl-benzyloxy)-benzenesulfonyl]-3-methoxy-piperidin-3-carboxylic acid hydroxyamide, 4-[4-(4-Fluoro-benzyloxy)-benzenesulfonyl]-3-methoxy-piperidin-3-carboxylic acid hydroxyamide, 4-[4-(4-Fluoro-2-methyl-benzyloxy)-benzenesulfonyl]-3-ethoxy-piperidin-3-carboxylic acid hydroxyamide, 4-[4-(4-Fluoro-2-chloro-benzyloxy)-benzenesulfonyl]-3-ethoxy-piperidin-3-carboxylic acid hydroxyamide, 4-[4-(2,4-Dichloro-benzyloxy)-benzenesulfonyl]-3-ethoxy-piperidin-3-carboxylic acid hydroxyamide, 4-[4-(5-Fluoro-2-methyl-benzyloxy)-benzenesulfonyl]-3-ethoxy-piperidin-3-carboxylic acid hydroxyamide, 4-[4-(4-Fluoro-benzyloxy)-benzenesulfonyl]-3-ethoxy-piperidin-3-carboxylic acid hydroxyamide, 3-Amino-4-[4-(4-fluoro-2-methyl-benzyloxy)-benzenesulfonyl]-2,2-dimethyl-piperidin-3-carboxylic acid hydroxyamide, 3-Amino-4-[4-(4-fluoro-2-chloro-benzyloxy)-benzenesulfonyl]-2,2-dimethyl-piperidin-3-carboxylic acid hydroxyamide, 3-Amino-4-[4-(2,4-dichloro-benzyloxy)-benzenesulfonyl]-2,2-dimethyl-piperidin-3-carboxylic acid hydroxyamide, 3-Amino-4-[4-(5-fluoro-2-methyl-benzyloxy)-benzenesulfonyl]-2,2-dimethyl-piperidin-3-carboxylic acid hydroxyamide, 3-Amino-4-[4-(4-fluoro-benzyloxy)-benzenesulfonyl]-2,2-dimethyl-piperidin-3-carboxylic acid hydroxyamide, 4-[4-(4-Fluoro-2-methyl-benzyloxy)-benzenesulfonyl]-3-methyl-2,2-dimethyl-piperidin-3-carboxylic acid hydroxyamide, 4-[4-(4-Fluoro-2-chloro-benzyloxy)-benzenesulfonyl]-3-methyl-2,2-dimethyl-piperidin-3-carboxylic acid hydroxyamide, 4-[4-(2,4-Dichloro-benzyloxy)-benzenesulfonyl]-3-methyl-2,2-dimethyl-piperidin-3-carboxylic acid hydroxyamide, 4-[4-(5-Fluoro-2-methyl-benzyloxy)-benzenesulfonyl]-3-methyl-2,2-dimethyl-piperidin-3-carboxylic acid hydroxyamide, 4-[4-(4-Fluoro-benzyloxy)-benzenesulfonyl]-3-methyl-2,2-dimethyl-piperidin-3-carboxylic acid hydroxyamide, 4-[4-(4-Fluoro-2-methyl-benzyloxy)-benzenesulfonyl]-3-hydroxy-2-oxo-piperidin-3-carboxylic acid hydroxyamide, 4-[4-(4-Fluoro-2-chloro-benzyloxy)-benzenesulfonyl]-3-hydroxy-2-oxo-piperidin-3-carboxylic acid hydroxyamide, 4-[4-(2,4-Dichloro-benzyloxy)-benzenesulfonyl]-3-hydroxy-2-oxo-piperidin-3-carboxylic acid hydroxyamide, 4-[4-(5-Fluoro-2-methyl-benzyloxy)-benzenesulfonyl]-3-hydroxy-2-oxo-piperidin-3-carboxylic acid hydroxyamide, and 4-[4-(4-Fluoro-benzyloxy)-benzenesulfonyl]-3-hydroxy-2-oxo-piperidin-3-carboxylic acid hydroxyamide.

The present invention also relates to a pharmaceutical composition for the treatment of a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising an amount of a compound of formula I or a pharmaceutically acceptable salt thereof effective in such treatments and a pharmaceutically acceptable carrier.

The present invention also relates to a pharmaceutical composition for the treatment of diseases characterized by metalloproteinase activity (preferably MMP-13) and other diseases characterized by mammalian reprolysin activity (preferably Aggrecanase activity most preferably Aggrecanase activity) in a mammal, including a human, comprising an amount of a compound of formula I or a pharmaceutically acceptable salt thereof effective in such treatments and a pharmaceutically acceptable carrier.

The present invention also relates to a pharmaceutical composition for the inhibition of (a) matrix metalloproteinases or other metalloproteinases involved in matrix degradation, or (b) a mammalian reprolysin (such as aggrecanase or ADAM's TS-1, 10, 12, 15 and 17, most preferably Aggrecanase) in a mammal, including a human, comprising an effective amount of a compound of formula I or a pharmaceutically acceptable salt thereof and a pharmaceutically acceptable carrier.

The present invention also relates to a method for treating a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising administering to said mammal an amount of a compound of formula I or a pharmaceutically acceptable salt thereof effective in treating such a condition.

The present invention also relates to the treatment of diseases characterized by matrix metalloproteinase activity (preferably MMP-13 activity) and other diseases characterized by mammalian reprolysin activity (preferably Aggrecanase activity) in a mammal, including a human, comprising administering to said mammal an amount of a compound of formula I or a pharmaceutically acceptable salt thereof effective in treating such a condition.

The present invention also relates to a method for the inhibition of (a) matrix metalloproteinases or other metalloproteinases involved in matrix degradation, or (b) a mammalian reprolysin (such as aggrecanase or ADAM's TS-1, 10, 12, 15 and 17, preferably Aggrecanase) in a mammal, including a human, comprising administering to said mammal an effective amount of a compound of formula I or a pharmaceutically acceptable salt thereof.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

This invention also encompasses pharmaceutical compositions containing prodrugs of compounds of the formula I. This invention also encompasses methods of treating or preventing disorders that can be treated or prevented by the inhibition of matrix metalloproteinases or the inhibition of mammalian reprolysin comprising administering prodrugs of compounds of the formula I. Compounds of formula I having free amino, amido, hydroxy, hydroxamic acid or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and esters which are covalently bonded to the above substituents of formula I through the carbonyl carbon prodrug sidechain.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TACE inhibitors, TNF-α inhibitors such as anti-TNF monoclonal antibodies and TNF receptor immunoglobulin molecules (such as Enbrel®), COX-2 inhibitors low dose methotrexate, lefunimide, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, paracoxib and rofecoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, requip, mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metryfonate.

The compounds of the present invention may also be used in combination with osteoporosis agents such as roloxifene, droloxifene or fosomax and immunosuppressant agents such as FK-506 and rapamycin.

DETAILED DESCRIPTION OF THE INVENTION

The following reaction Schemes illustrate the preparation of the compounds of the present invention. Unless otherwise indicated $R^1$–$R^5$, X, Z and Q in the reaction Schemes and the discussion that follow are defined as above.

SCHEME 1

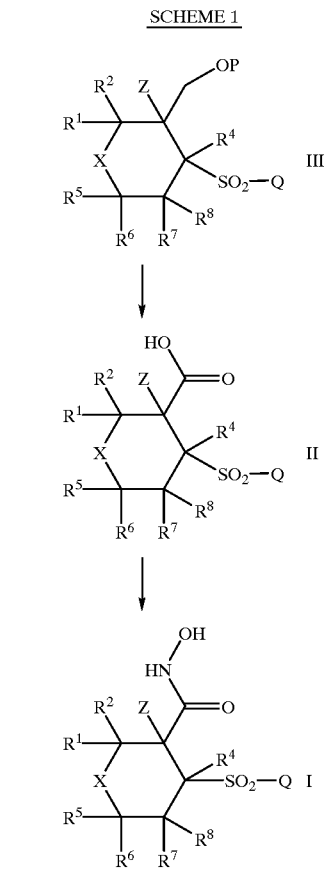

SCHEME 2
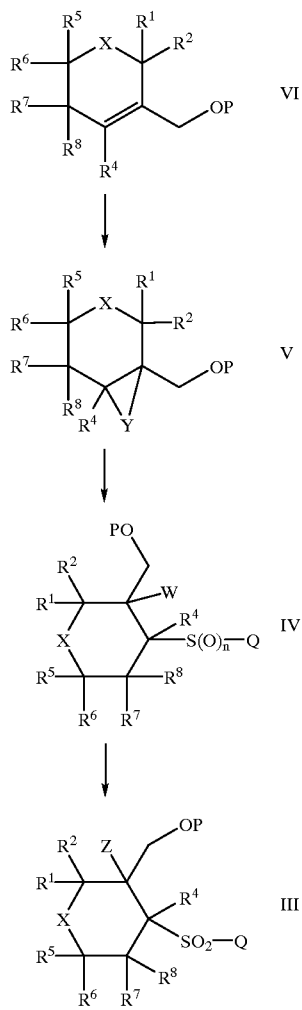
SCHEME 3
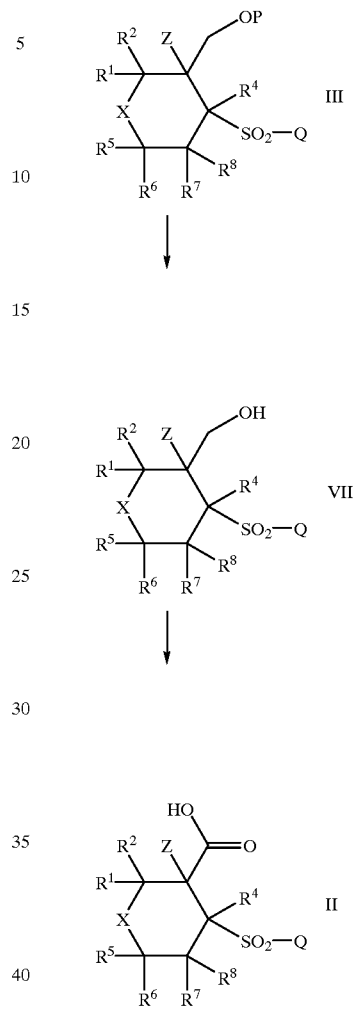
SCHEME 4
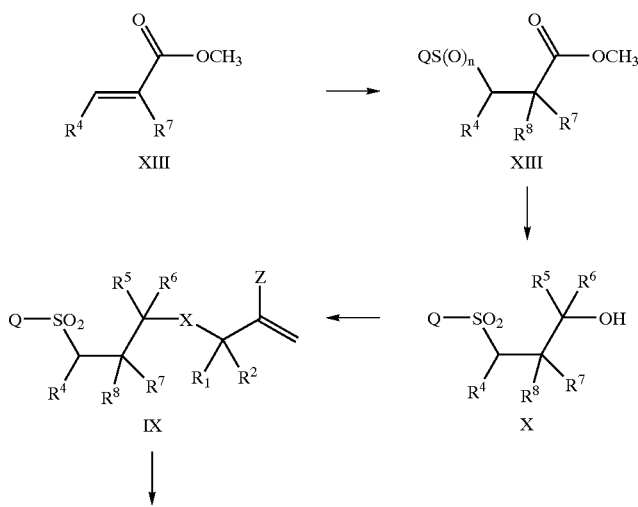

-continued

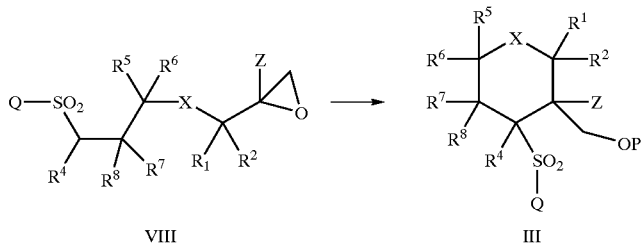

VIII → III

SCHEME 5

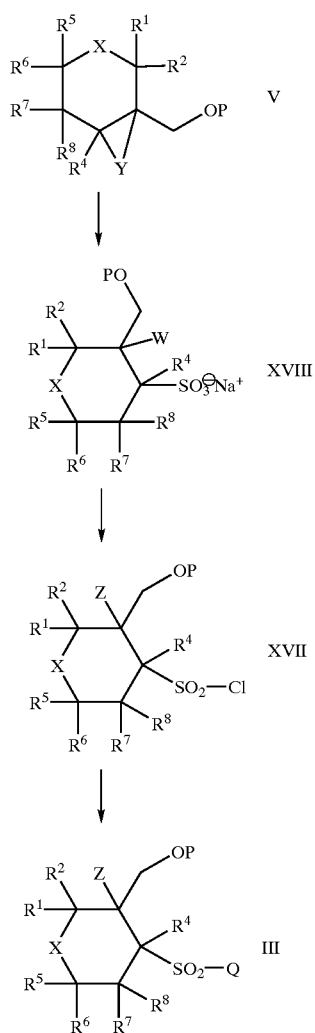

V → XVIII → XVII → III

SCHEME 6

Q—SO₂Cl  XV

↓

Q—SH  XIV

SCHEME 7

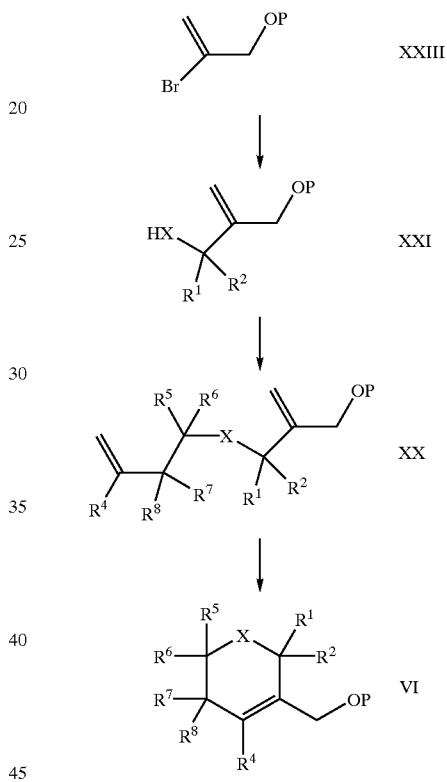

XXIII → XXI → XX → VI

Scheme I refers to preparation of compounds of the formula I. Compounds of the formula I possess specific stereochemistry about the chiral hydroxamic acid carbon and sulfonyl carbon. The stereochemistry of the final product of formula I is determined by the stereochemistry at the epoxidation or aziridination step in Scheme 2. One of ordinary skill in the art will understand that after opening the epoxide or aziridine that subsequent intermediates may be epimerized so as to produce stereoisomeric mixtures that can be separated into individual stereoisomers, such as enantiomers or diastereomers, by methods well known to those skilled in the art.

Referring to Scheme 1, the compound of formula I is prepared from the carboxylic acid of formula II by treatment with an activating agent such as 1-(3-dimethylaminopropyl)-3-ethylcarbodiimide and 1-hydroxybenztriazole in a polar solvent, such as N,N-dimethylformamide, followed by the addition of hydroxylamine to the reaction mixture after a time period between about 15 minutes to about 1 hour, preferably about 30 minutes. The aforesaid reaction is conducted at a temperature of about 0° C. to about 50° C. preferably about 20° C. to about 23° C. The hydroxylamine is preferably generated in situ from a salt form, such as hydroxylamine hydrochloride, in the presence of a base, such as triethylamine.

Alternatively the compound of formula I can be prepared from a compound of formula II by reaction with a protected derivative of hydroxylamine or its salt form, where the hydroxyl group is protected as a tert-butyl, benzyl, allyl or 2-trimethylsilylethyl ether. Removal of the hydroxyl protecting group is carried out by hydrogenolysis for a benzyl protecting group (5% palladium on barium sulfate is the preferred catalyst) or treatment with a strong acid, such as trifluoroacetic acid, for a tert-butyl protecting group. The allyl protecting group may be removed by treatment with triethylamine and formic acid in the presence of catalytic tetrakis(triphenylphosphine) palladium(0) or tributyltinhydride and acetic acid in the presence of catalytic bis (triphenylphosphine) palladium(II)chloride. The 2-trimethylsilylethyl ether may be removed by reaction with a strong acid such as trifluoroacetic acid or by reaction with a fluoride source such as boron trifluoride etherate.

The reaction of a compound of formula II with hydroxylamine, a salt of hydroxylamine, a protected derivative of hydroxylamine or a salt of a protected derivative of hydroxylamine may also be carried out in the presence of (benztriazol-1-yloxy)tris(dimethylamino)-phosphonium hexafluorophosphate and a base such as triethylamine in an inert solvent, such as methylene chloride. The reaction mixture is stirred at a temperature between about 0° C. to about 50° C., preferably room temperature, for a time period between about 1 hour to about 3 days, preferably about 1 day.

Another procedure for converting a compound of formula II to a compound of formula I is to react the compound of formula II with O-benzylhydroxylamine hydrochloride in the presence of (benztriazol-1-yloxy)tris(dimethylamino) phosphonium hexafluorophosphate and triethylamine using methylene chloride as solvent. Subsequent removal of the O-benzyl protecting group to afford a compound of formula I is then carried out by hydrogenolysis under 3 atmospheres hydrogen at room temperature using 5% palladium on barium sulfate as a catalyst. The preferred solvent is methanol. The reaction time may vary from about 1 hour to about 2 days (8 hours is preferred).

Another alternative procedure for converting a compound of formula II to a compound of formula I is to react the compound of formula II with oxalyl chloride in methylene chloride in the presence of a catalytic amount of DMF for 16 hours. The resulting acid chloride is reacted at 0° C. with N, O-bis trimethylsilyl hydroxylamine formed by reacting hydroxyamine hydrochloride with chlorotrimethyl-silane in pyridine at 0° C. to room temperature. The product of formula I is obtained after a few hours reaction at about 0° C. to about 20–23° C. (i.e. room temperature) followed by an acidic aqueous workup which removes all trimethyl silyl residues.

In certain instances, it is preferred to obtain the compound of formula I by reaction of hydroxylamine, a salt of hydroxylamine, a protected derivative of hydroxylamine or a salt of a protected derivative of hydroxylamine with an activated ester equivalent of formula II. The reaction is carried out in an inert solvent, such as N,N-dimethylformamide at a temperature ranging from about 20–23° C. (i.e. room temperature) to about 80° C., preferably about 60° C. for a time period of about 1 hour to about 2 days. If a protected derivative of hydroxylamine or a salt of a protected derivative of hydroxylamine is used, removal of the protecting group is carried out as described above. The activated ester equivalent derivative of formula II is obtained by treatment of the compound of formula II with (benztriazol-1-yloxy)tris(dimethylamino)-phosphonium hexafluorophosphate and a base such as triethylamine in an inert solvent, such as methylene chloride. The reaction mixture is stirred at a temperature between about 0° C. to about 50° C., preferably room temperature, for a time period between about 1 hour to about 3 days, preferably about 1 day.

A compound of the formula II, wherein Z is $-OR^{11}$, $>NR^{12}R^{13}$ or optionally substituted alkyl (suitably protected where appropriate) and $R^{11}$, $R^{12}$ and $R^{13}$ are each hydrogen, may be prepared from a compound of the formula III, wherein wherein Z is $-OR^{11}$, $>NR^{12}R^{13}$ or optionally substituted alkyl (suitably protected where appropriate) and $R^{11}$, $R^{12}$ and $R^{13}$ are each hydrogen and P is hydrogen, by treatment with a suitable oxidant, such as Jones Reagent or under other known conditions employing an alkali metal chlorite salt, preferably sodium chlorite in the presence of a suitable catalyst, such as a mixture of 2,2,6,6-tetramethyl-1-piperidinyloxy free radical (TEMPO) and sodium hypochlorite in a pH 7 buffered aqueous solution, with an appropriate aprotic polar co-solvent, preferably acetonitrile, from about 0° C. to about 50° C., for about 4 to about 12 hours.

A compound of the formula II, wherein Z is $-OR^{11}$ or $-NR^{12}R^{13}$ and $R^{11}$ is other than hydrogen or at least one of $R^{12}$ and $R^{13}$ is other than hydrogen can be prepared by the methods of Scheme 3.

A compound of the formula III, wherein Z is $-OR^{11}$ or $-NR^{12}R^{13}$ and $R^{11}$, $R^{12}$ and $R^{13}$ are each hydrogen can be prepared according to the methods of Scheme 2. Compounds of the formula III, wherein Z is optionally substituted alkyl can be prepared according to the methods of Scheme 4.

Scheme 2 refers to the preparation of compounds of the formula III, wherein Z is $-OR^{11}$ or $-NR^{12}R^{13}$ and $R^{11}$, $R^{12}$ and $R^{13}$ are each hydrogen and P is hydrogen or a protecting group. Compounds of the formula III can be converted into compounds of the formula I according to the methods of Scheme 1.

A compound of the formula III, wherein Z is $-OR^{11}$ or $-NR^{12}R^{13}$ and $R^{11}$, $R^{12}$ and $R^{13}$ are each hydrogen and P is hydrogen, may be prepared from a compound of the formula III, wherein Z is $-OR^{11}$ or $>NR^{12}R^{13}$ and $R^{11}$, $R^{12}$ and $R^{13}$ are each hydrogen and P is a protecting group, by removal of the protecting group. Suitable protecting groups, including methods for their formation and cleavage, are described in detail in Greene and Wuts, *"Protective Groups in Organic Synthesis"* (Willey Interscience, 2nd Ed.) (1991), see Chapter 2, incorporated herein by reference. When the protecting group is a silyl ether (such as t-butyl-dimethyl silyl ether), the reaction is carried out in a solvent such as THF, acetonitrile or methylene chloride with an excess of a fluoride source such as tetrabutyl ammonium fluoride, hydrogen fluoride in pyridine, boron trifluoride etherate, or cesium fluoride, preferably tetrabutyl ammonium fluoride in THF or in a solvent such as wet THF or wet methanol with an excess of a protic acid such as dilute hydrochloric acid, acetic acid or toluene sulfonic acid, preferably dilute hydrochloric acid. The reaction mixture is stirred at a temperature of from about 0° C. to about 80° C., preferably about 20° C. (room temperature) for a time period of about 10 minutes to about 2 days, preferably about 1 hour.

A compound of the formula III, wherein Z is —OR$^{11}$, R$^{11}$ is hydrogen and P is a protecting group, may be prepared from a compound of the formula IV, wherein W is —OR$^{11}$, R$^{11}$ is hydrogen, P is a protecting group and n is zero, by treatment with a suitable oxidant such as a peroxide or peroxyacid, preferably peroxyacetic acid, in the presence of a suitable buffer salt, such as sodium acetate in a polar solvent such as methylene chloride at a temperature from about −20° C. to about 50° C. for a period from about 2 hours to about 4 hours.

A compound of the formula III, wherein Z is —NR$^{12}$R$^{13}$ and R$^{12}$ and R$^{13}$ are each hydrogen and P is protecting group such as a silyl ether (such as t-butyl-dimethyl silyl ether), may be prepared from a compound of the formula IV, wherein W is —NHR$^{14}$ and R$^{14}$ is alkyl-O—(C=O)— and P is a protecting group and n is 2, by treatment with a suitable strong base, such as an alkoxide base, preferably potassium hydroxide, in a polar aprotic solvent such as an alcohol water mixture, at a temperature range of about 50° C. to about 120° C., for a period from about 12 to about 48 hours.

Alternatively, a compound of the formula III, wherein Z is —NR$^{12}$R$^{13}$ and R$^{12}$ and R$^{13}$ are each hydrogen and P is protecting group such as a silyl ether (such as t-butyl-dimethyl silyl ether), may be prepared from a compound of the formula IV, wherein W is —NHR$^{14}$, R$^{14}$ is —(SO$_2$)-aryl and n is 2, by employment of a dissolving metal reduction, using an appropriate alkali metal such as sodium metal in liquid ammonia ethanol solution at a temperature of about −33° C. to about 50° C., for a period from about 1 hour to about 3 hours.

A compound of the formula IV, wherein W is —NHR$^{14}$ and R$^{14}$ is alkyl-O—(C=O)— or —(SO$_2$)-aryl, P is a protecting group such as a silyl ether (such as t-butyl-dimethyl silyl ether) and n is 2, may be prepared from a compound of the formula IV, wherein W is —NHR$^{14}$ and R$^{14}$ is alkyl-O—(C=O)— or —(SO$_2$)-aryl, P is a protecting group such as a silyl ether (such as t-butyl-dimethyl silyl ether) and n is zero, by treatment with a suitable oxidant such as a peroxide or peroxyacid, preferably peroxyacetic acid, in the presence of a suitable buffer salt, such as sodium acetate in a polar solvent such as methylene chloride at a temperature from about −20° C. to about 50° C. for a period from about 2 hours to about 4 hours.

The compound of the formula IV, wherein W is —OR$^{11}$ or —NHR$^{14}$ and R$^{11}$ is hydrogen and R$^{14}$ is alkyl-O—(C=O)— or —(SO$_2$)-aryl, P is hydrogen or a protecting group such as a silyl ether (such as t-butyl-dimethyl silyl ethers) and n is zero, may be prepared from a compound of the formula V, wherein Y is —O— or >NR$'^4$ and R$'^4$ is alkyl-O—(C=O)— or aryl(SO$_2$)— and P is a protecting group or hydrogen, by treatment with a compound of formula QSH in the presence of a suitable base, such as an alkali metal hydride, tertiary amine base or alkoxide base, preferably sodium hydride or triethylamine, in a polar solvent such as acetonitrile, DMSO, DMF, methanol or an ethereal solvent, preferably THF, at a temperature range of about 0° C. to about 70° C., for a period from about 4 hours to about 48 hours. Optionally such reactions can be performed in the presence of a perchlorate salt, such as lithium or magnesium perchlorate. Other similar methods are described in J. Org. Chem., 2514–2525 (1995).

The compound of the formula V, wherein Y is —O— and P is hydrogen or a protecting group, is prepared from a compound of the formula VI by epoxidation using a suitable oxidant such as a peracid or peroxide based oxidant. One of ordinary skill in the art will appreciate that such oxidations can be facilitated by a transition metal catalyst and can be performed enantioselectively under so-called Sharpless or Jacobsen conditions. Either enantiomer of V may be prepared by oxidation in the presence of the appropriate enantiomer of the chiral ligand. In the case of the Sharpless epoxidation, this would be either (D) or (L) diisopropyl tartrate. For preparation of the racemic compounds, suitable oxidants include tert-butylhydroperoxide. Suitable solvents include benzene or toluene in the presence of a metal catalyst, preferably a vanadium catalyst, most preferably vanadyl acetoacetonate at a temperature range from ambient temperature to the boiling point of the solvent, for a period from about 1 hours to about 12 hours.

The compound of the formula V, wherein Y is >NR$^{14}$ and R$^{14}$ is alkyl-O—(C=O)— or —(SO$_2$)-alkyl and P is hydrogen, is prepared from a compound of the formula VI by reaction with an aziridination reagent such as alkyl-O—(C=O)—NH-O—SO$_2$-aryl, aryl-SO$_2$—NH—Cl or alkyl-O—(C=O)—N$_3$, in the presence of a transition metal catalyst (such as a Cu(II) catalyst) or by photochemical irradiation. Suitable solvents include benzene or toluene. The aforesaid reaction may be performed at a temperature range from about about 10° C. to about the boiling point of the solvent (e.g. 100° C.), for a time sufficient for the full conversion (about 1 to about 12 hours). Similar methods are also described in Tetrahedron, 14105–14112 (1998).

A compound of the formula V, wherein Y is —O— or >NR$^{14}$ and R$^{14}$ is alkyl-(C=O)— or aryl(SO$_2$)— and P is a protecting group such as a silyl protecting group (such as t-butyl dimethyl silyl ether), may be prepared from a compound of the formula V, wherein Y is —O— or >NR$^{14}$ and R$^{14}$ is alkyl-(C=O)— or aryl(SO$_2$)— and P is hydrogen, by reaction with an activated protecting group such as t-butyl-dimethyl-silyl chloride or trimethylsilyl chloride in the presence of a base such as pyridine, 2,6-lutidine, imidazole or diisopropylethylamine, preferably triethylamine or imidazole. Suitable solvents include methylene chloride, DMF or toluene. The reaction is performed at a temperature of about 0° to about 22° C. (i.e., room temperature) for about 1 to about 12 hours, preferably about 1 hour.

Compounds of formula VI are well known in the literature or are commercially available. Compounds of the formula VI can also be prepared according to the methods of Scheme 7.

Scheme 3 refers to the preparation of compounds of the formula II, wherein Z is —OR$^{11}$ or >NR$^{12}$R$^{13}$ and R$^{11}$ is other than hydrogen or at least one of R$^{12}$ and R$^{13}$ is other than hydrogen. Said compounds of the formula II can be converted to compounds of formula I according to the methods of Scheme 1, for the conversion of compounds of the formula II to formula I.

Referring to Scheme 3, a compound compound of the formula II, wherein Z is —OR$^{11}$ or >NR$^{12}$R$^{13}$ and R$^{11}$ is other than hydrogen or at least one of R$^{12}$ and R$^{13}$ is other than hydrogen, may be prepared from a compound of the formula VII, wherein Z is —OR$^{11}$ or >NR$^{12}$R$^{13}$ and R$^{11}$ is other than hydrogen or at least one of R$^{12}$ and R$^{13}$ is other than hydrogen, by treatment with a suitable oxidant, such as Jones Reagent or under other known conditions employing an alkali metal chlorite salt, preferably sodium chlorite in the presence of a suitable catalyst, such as a mixture of 2,2,6,6-tetramethyl-1-piperidinyloxy free radical (TEMPO) and sodium hypochlorite in a pH 7 buffered aqueous solution, with an appropriate aprotic polar co-solvent, preferably acetonitrile, from about 0° C. to about 50° C., for about four to about 12 hours.

The compound of the formula VII, wherein Z is —OR$^{11}$ or >NR$^{12}$R$^{13}$ and R$^{11}$ is other than hydrogen or at least one of R$^{12}$ and R$^{13}$ is other than hydrogen, can be prepared from a compound of formula III, wherein Z is —OR$^{11}$ or >NR$^{12}$R$^{13}$ and R$^{11}$ is other than hydrogen or at least one of R$^{12}$ and R$^{13}$ is other than hydrogen and P is a protecting group (such as t-butyldimethylsilyl), by reaction with a strong acid such as trifluoroacetic acid or by reaction with a fluoride source such as boron trifluoride etherate.

The compound of the formula III, wherein Z is —OR$^{11}$ or —NR$^{12}$R$^{13}$ and R$^{11}$ is other than hydrogen or at least one of R$^{12}$ and R$^{13}$ is other than hydrogen and P is a protecting group, can be prepared from compounds of the formula III, from Scheme 1, wherein Z is —OR$^{11}$ or —NR$^{12}$R$^{13}$ and R$^{11}$, R$^{12}$ and R$^{13}$ are each hydrogen and P is a protecting group, by reaction with an alkylating or acylating agent. When the reactant is an alkylating reagent, such as R$^{11}$-L, R$^{12}$-L or R$^{13}$-L and L is a halogen such as iodo, bromo or chloro, and Z is —OR$^{11}$ then the reaction is performed in the presence of a suitable base, such as sodium hydride, potassium hydride, sodium hexamethydisalyzide, in a polar solvent such as tetrahydrofuran or dimethylformamide, at a temperature of about 0° C. to about the reflux temperature of the solvent for a period from about 15 minutes to about 4 hours. When the reactant is an alkylating reagent, such as R$^{11}$-L, R$^{12}$-L or R$^{13}$-L and L is a halogen such as iodo, bromo or chloro, and Z is >NR$^{12}$R$^{13}$, then the presence of a base is optional (i.e. the nitrogen atom may serve as the molecule's own base). When the alkylating agent is an aldehyde or ketone (such as alkyl(C=O)—H or alkyl (C=O)alkyl) then the condensation is performed in the presence of a reducing reagent such as sodium cyano borohydride. When the reactant is an acylating reagent (e.g., alkyl(C=O)-L, wherein L is halo) then the reaction is performed in the presence of a suitable base, such as triethylamine or pyridine, in a polar solvent such as methylene choride or THF, at a temperature of about 0° C. to about 40° C. for a period from about 15 minutes to about 4 hours.

Scheme 4 refers to the preparation of compounds of the formula III, wherein Z is optionally substituted alkyl and P is hydrogen. Said compounds of the formula III can be converted to compounds of the formula I according to the methods of Scheme 1.

Referring to Scheme 4, a compound of the formula III, wherein Z is optionally substituted alkyl and P is hydrogen, can be prepared from a compound of the formula VIII by reaction with a suitable base in a polar aprotic solvent. Suitable bases include lithium dialkylamides (e.g. lithium diisopropylamide). Suitable solvents include tetrahydrofuran, digylme or ether. The aforesaid reaction can be performed at a temperature of about about −78° C. to about 0° C. for a period from about 15 minutes to about 4 hours.

A compound of formula VIII can be prepared by epoxidation of a compound of formula IX using a suitable oxidant such as a peracid or peroxide based oxidant. One of ordinary skill in the art will appreciate that such oxidations can be facilitated by a transition metal catalyst and can be performed enantioselectively under so-called Jacobsen conditions. The epoxide may be formed as the racemate by treating the compound of formula IX with a suitable oxidant, such as metachloroperbenzoic acid in a suitable solvent, such as methylene chloride ether or toluene at a temperature range from about 0° C. to the boiling point of the solvent (100° C.), for a time sufficient for the full conversion.

A compound of formula IX can be prepared from a compound of formula X by reaction with a compound of the formula

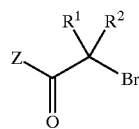

XI wherein Z is optionally substituted alkyl, in the presence of a suitable base and a suitable solvent. Suitable bases include sodium hydride or potassium hydride. Suitable solvents include tetrahydrofuran or DMF. The aforesaid reaction can be performed at a temperature of about about 0° C. to about 80° C. for a period from about 2 hours to about 24 hours.

Alternatively, a compound of formula IX can be prepared from a compound of formula X', wherein the hydroxy group in the compound of formula X has been converted to a leaving group such as tosylate according to methods well known to those skilled in the art, by reaction with a compound of the formula

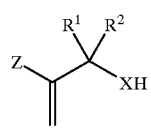

XI' wherein Z is optionally substituted alkyl, in the presence of a suitable base and a suitable solvent. Suitable bases include sodium hydride or potassium hydride. Suitable solvents include tetrahydrofuran or DMF. The aforesaid reaction can be performed at a temperature of about about 0° C. to about 80° C. for a period from about 2 hours to about 24 hours.

A compound of the formula X can be prepared from a compound of the formula XII by reaction with a hydride reagent such as lithium aluminum hydride, lithium triethyl borohydride or lithium borohydride, preferably lithium aluminum hydride, in an inert solvent solvent such as THF or ether, preferably THF, at a temperature of from about 0° C. to about 25° C., preferably about 20° C. to about room temperature for a period of time of from about 10 minutes to about 1 day, preferably about 1 hour.

A compound of formula XII, wherein n is 2, can be prepared from a compound of formula XII, wherein n is zero, by reaction with an oxidant such as m-CPBA or peracetic acid in an aprotic solvent such as methylene chloride at about 0° C. to about 40° C. for about 2 to about 24 hours.

A compound of the formula XII, wherein n is zero, can be prepared from a compound of the formula XIII by reaction with a compound of the formula QSH in the presence of a suitable base in a suitable solvent. Suitable bases include sodium hydride. Suitable solvents include tetrahydrofuran or DMF. The aforesaid reaction can be performed at a temperature of about about 0° C. to about the reflux temperature of the solvent (e.g., 50° C. for THF) for a period from about 2 hours to about 24 hours.

Compounds of the formula XIII are commercially available or can be made by methods well known to those skilled in the art.

Scheme 5 refers to an alternate preparation of compounds of the formula III, wherein Q is heterocyclic and the point of attachment of Q to the ring is through a heteroatom such as N.

Referring to Scheme 5, a compound of the formula III is prepared from a compound of formula XVII by reaction with a compound of the formula QH, wherein the H (i.e. hydrogen) is attached to a ring nitrogen atom in the presence of a base (such as pyridine or triethylamine), in a polar solvent such as methylene chloride DMF or THF. The temperature of the aforesaid reaction is form about 0° C. to about 50° C., and the reaction is run for about 10 minutes to about 4 hours.

The compound of formula XVII is prepared from a compound of formula XVIII by reaction with a chlorinating agent. Suitable chlorinating agents includes $POCl_3$, $PCl_5$ or $SOCl_2$ or mixtures of triphenylphosphine and hexachloroethane. The aforesaid reaction is run at a temperature of about 0° C. to about 100° C. for a period from about 1 hour to about 5 hours.

The compound of formula XVIII is prepared from a compound of formula V by reaction with sodium thiosulfate or sodium sulfite in a polar solvent. Suitable solvents include alcohols and water, preferably an ethanol water mixture such as 3:1 ethanol water. The reaction is run for about 5 hours to about 24 hours at a temperature from about 50° C. to about 100° C.

The compounds of the formula V can be prepared according to the methods of Scheme 2.

Scheme 6 refers to preparation of compounds of the formula XIV. Referring to Scheme 6, compounds of the formula XIV are prepared from a compound of the formula XV by reduction of the sulfonyl chloride using a suitable reducing agent, such as a metal reducing agent, preferably zinc, in an appropriate solvent, such as an acidic solvent, preferably acetic acid or mixtures of water and HCl at a temperature between 0° C. and 80° C. for a period of time sufficient to convert XV to XIV. Compounds of the formula XV are commercially available or can be prepared by methods well known to those skilled in the art.

Scheme 7 refers to preparation of compounds of the formula VI, which are intermediates in Scheme 2.

Referring to Scheme 7, compounds of the formula VI may be prepared under so-called Grubbs Metathesis conditions by treating a compound of the formula XX with a ruthenium catalyst, preferably bis (tricyclohexylphosphine) benzylidine ruthenium (IV) dichloride in a suitable solvent such as methylene chloride or dichloroethane at a temperature between about 23° C. and about 60° C. for about 2 to about 12 hours.

Compounds of the formula XX can be prepared by alkylation of compounds of the formula XXI, wherein X is O with a compound of the formula

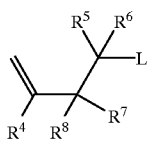

XXIIa wherein L is a leaving group, such as but-3-enyl-1-iodide, in the presence of a suitable base, such as sodium hydride or potassium hydride in a polar aprotic solvent, such as DMF or THF. In the case where X is N, similar conditions may be used. Alternatively the compound of formula XXI may be treated with the appropriate compound of formula XXIIb

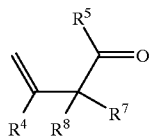

XXIIb such as 3-butenone, in the presence of a suitable reducing agent such as sodium cyanoborohydride in a polar solvent, preferably methanol.

Compounds of the formula XXI can be prepared by treating a compound of the formula XXIII with an alkyl lithium, such as n-butyllithium or t-butyllithium in an ethereal solvent, preferably THF or ether at a temperature between −78° C. to −50° C. The appropriately substituted ketone (such as $R^1R^2(C=O)$) or protected imine (such as $R^1R^2(C=N)$-benzyl) is then added and allowed to react at a temperature between about −78° C. and about 23° C. for about 2 to about 24 hours.

The ability of the compounds of formula I or their pharmaceutically acceptable salts (hereinafter also referred to as the compounds of the present invention) to inhibit metalloproteinases or mammalian reprolysin and, consequently, demonstrate their effectiveness for treating diseases characterized by metalloproteinase or mammalian reprolysin disregulation (e.g., the over production of tumor necrosis factor or aggrecanase preferably aggrecanase) is shown by the following in vitro assay tests.

BIOLOGICAL ASSAYS

The ability of the compounds of formula I or their pharmaceutically acceptable salts (hereinafter also referred to as the compounds of the present invention) to inhibit metalloproteinases or mammalian reprolysin and, consequently, demonstrate their effectiveness for treating diseases characterized by metalloproteinase or the mammalian reprolysin activity (such as the inhibition of aggrecanase) is shown by the following in vitro assay tests.

MMP Assays

Collagenase-3 (matrix metalloproteinase-13) selective inhibitors as used herein refer to agents which exhibit at least a 100 fold selectivity for the inhibition of collagenase-3 enzyme activity over collagenase-1 enzyme activity and a potency of less than 100 nM as defined by the IC., results from the MMP-13/MMP-1 fluorescence assays described below. Collagenase-3 selective inhibitors can be identified by screening the inhibitors of the present invention through the MMP-13/MMP-1 fluorescence assays described below and selecting those agents with MMP-13/MMP-1 inhibition $IC_{50}$ ratios of 100 or greater and potency of less than 100 nM.

Non-selective collagenase inhibitors as used herein refer to agents which exhibit less than a 100 fold selectivity for the inhibition of collagenase-3 enzyme activity and/or Aggrecanase activity over collagenase-1 enzyme activity or a potency of more than 10 $\mu$M, more preferably 1 $\mu$M, most preferably 100 nM, as defined by the $IC_{50}$ results from the MMP-13 fluorescence assay and/or Aggrecanase in vitro assay described below.

The ability of collagenase inhibitors to inhibit collagenase activity is well known in the art. The following assays may be used to identify matrix metalloproteinase inhibitors.

Inhibition of Human Collagenase (MMP-1)

Human recombinant collagenase is activated with trypsin. The amount of trypsin is optimized for each lot of collagenase-1 but a typical reaction uses the following ratio: 5 μg trypsin per 100 μg of collagenase. The trypsin and collagenase are incubated at room temperature for 10 minutes then a five fold excess (50 mg/10 mg trypsin) of soybean trypsin inhibitor is added.

Stock solutions (10 mM) of inhibitors are made up in dimethylsulfoxide and then diluted using the following scheme:

10 mM→120 μM→12 μM→1.2 μM→0.12 μM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D7–D12 and negative controls (no enzyme, no inhibitors) are set in wells D1–D6.

Collagenase-1 is diluted to 240 ng/ml and 25 μl is then added to appropriate wells of the microfluor plate. Final concentration of collagenase in the assay is 60 ng/ml.

Substrate (DNP-Pro-Cha-Gly-Cys(Me)-His-Ala-Lys (NMA)—$NH_2$) is made as a 5 mM stock in dimethylsulfoxide and then diluted to 20 μM in assay buffer. The assay is initiated by the addition of 50 μl substrate per well of the microfluor plate to give a final concentration of 10 μM.

Fluorescence readings (360 nM excitation, 460 nm emission) are taken at time 0 and then at 20 minute intervals. The assay is conducted at room temperature with a typical assay time of 3 hours Fluorescence versus time is then plotted for both the blank and collagenase containing samples (data from triplicate determinations is averaged). A time point that provides a good signal (at least five fold over the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration versus % control (inhibitor fluorescence divided by fluorescence of collagenase alone× 100). $IC_{50}$'s are determined from the concentration of inhibitor that gives a signal that is 50% of the control.

If $IC_{50}$'s are reported to be less than 0.03 μM then the inhibitors are assayed at concentrations of 0.3 μM, 0.03 μM, and 0.003 μM.

Inhibition of Gelatinase (MMP-2)

Human recombinant 72 kD gelatinase (MMP-2, gelatinase A) is activated for 16–18 hours with 1 mM p-aminophenyl-mercuric acetate (from a freshly prepared 100 mM stock in 0.2 N NaOH) at 4° C., rocking gently.

10 mM dimethylsulfoxide stock solutions of inhibitors are diluted serially in assay buffer (50 mM TRIS, pH 7.5, 200 mM NaCl, 5 mM $CaCl_2$, 20 μM $ZnCl_2$ and 0.02% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 100 ng/mL in assay buffer, 25 μL per well is added to appropriate wells of the microplate. Final enzyme concentration in the assay is 25 ng/mL (0.34 nM).

A five mM dimethylsulfoxide stock solution of substrate (Mca-Pro-Leu-Gly-Leu-Dpa-Ala-Arg-$NH_2$) is diluted in assay buffer to 20 μM. The assay is initiated by addition of 50 μL of diluted substrate yielding a final assay concentration of 10 μM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of Stromelysin Activity (MMP-3)

Human recombinant stromelysin (MMP-3, stromelysin-1) is activated for 20–22 hours with 2 mM p-aminophenylmercuric acetate (from a freshly prepared 100 mM stock in 0.2 N NaOH) at 37° C.

10 mM dimethylsulfoxide stock solutions of inhibitors are diluted serially in assay buffer (50 mM TRIS, pH 7.5, 150 mM NaCl, 10 mM $CaCl_2$ and 0.05% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 200 ng/mL in assay buffer, 25 μL per well is added to appropriate wells of the microplate. Final enzyme concentration in the assay is 50 ng/mL (0.875 nM).

A ten mM dimethylsulfoxide stock solution of substrate (Mca-Arg-Pro-Lys-Pro-Val-Glu-Nva-Trp-Arg-Lys(Dnp)-$NH_2$) is diluted in assay buffer to 6 μM. The assay is initiated by addition of 50 μL of diluted substrate yielding a final assay concentration of 3 μM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of Human 92 kD Gelatinase (MMP-9)

Inhibition of 92 kD gelatinase (MMP-9) activity is assayed using the Mca-Pro-Leu-Gly-Leu-Dpa-Ala-Arg- NH$_2$ substrate (10 μM) under similar conditions as described above for the inhibition of human collagenase (MMP-1).

Human recombinant 92 kD gelatinase (MMP-9, gelatinase B) is activated for 2 hours with 1 mM p-aminophenylmercuric acetate (from a freshly prepared 100 mM stock in 0.2 N NaOH) at 37 C.

10 mM dimethylsulfoxide stock solutions of inhibitors are diluted serially in assay buffer (50 mM TRIS, pH 7.5, 200 mM NaCl, 5 mM CaCl$_2$, 20 μM ZnCl$_2$, 0.02% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 100 ng/mL in assay buffer, 25 μL per well is added to appropriate wells of the microplate. Final enzyme concentration in the assay is 25 ng/mL (0.27 nM).

A five mM dimethylsulfoxide stock solution of substrate (Mca-Pro-Leu-Gly-Leu-Dpa-Ala-Arg-NH$_2$) is diluted in assay buffer to 20 μM. The assay is initiated by addition of 50 μL of diluted substrate yielding a final assay concentration of 10 μM substrate. A 0 time fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for IC$_{50}$ determinations. The 0 time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. IC$_{50}$'s are defined as the concentration of inhibitor that gives a signal that is 50% of the positive enzyme control.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 μM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 μM, 3 μM, 0.3 μM, and 0.03 μM.

Substrate (Dnp-Pro-Cha-Gly-Cys(Me)-His-Ala-Lys (NMA)-NH$_2$) is prepared as for inhibition of human collagenase (MMP-1) and 50 μl is added to each well to give a final assay concentration of 10 μM. Fluorescence readings (360 nM excitation; 450 emission) are taken at time 0 and every 5 minutes for 1 hour.

Positive controls consist of enzyme and substrate with no inhibitor and blanks consist of substrate only.

IC$_{50}$'s are determined as per inhibition of human collagenase (MMP-1). If IC$_{50}$'s are reported to be less than 0.03 μM, inhibitors are then assayed at final concentrations of 0.3 μM, 0.03 μM, 0.003 μM and 0.0003 μM.

Collagen film MMP-13 Assay

Rat type I collagen is radiolabeled with $^{14}$C acetic anhydride (T. E. Cawston and A. J. Barrett, *Anal. Biochem.*, 99, 340–345 (1979)) and used to prepare 96 well plates containing radiolabeled collagen films (Barbara Johnson-Wint, *Anal. Biochem.*, 104, 175–181 (1980)). When a solution containing collagenase is added to the well, the enzyme cleaves the insoluble collagen which unwinds and is thus solubilized. Collagenase activity is directly proportional to the amount of collagen solubilized, determined by the proportion of radioactivity released into the supernatant as measured in a standard scintillation counter. Collagenase inhibitors are, therefore, compounds which reduce the radioactive counts released with respect to the controls with no inhibitor present. One specific embodiment of this assay is described in detail below.

For determining the selectivity of compounds for MMP-13 versus MMP-1 using collagen as a substrate, the following procedure is used Recombinant human proMMP-13 or proMMP-1 is activated according to the procedures outlined above. The activated MMP-13 or MMP-1 is diluted to 0.6 ug/ml with buffer (50 mM Tris pH 7.5, 150 mM NaCl, 10 mM CaCl$_2$, 1 uM ZnCl$_2$, 0.05% Brij-35, 0.02% sodium azide).

Stock solutions of test compound (10 mM) in dimethylsulfoxide are prepared. Dilutions of the test compounds in the Tris buffer, above, are made to 0.2, 2.0, 20, 200, 2000 and 20000 nM.

100 μl of appropriate drug dilution and 100 μl of diluted enzyme are pipetted into wells of a 96 well plate containing collagen films labeled with $^{14}$C-collagen. The final enzyme concentration is 0.3 μg/ml while the final drug concentration is 0.1, 1.0, 10, 100, 1000 nM. Each drug concentration and control is analyzed in triplicate. Triplicate controls are also run for the conditions in which no enzyme is present and for enzyme in the absence of any compound.

The plates are incubated at 37° C. for a time period such that around 30–50% of the available collagen is solubilized-determined by counting additional control wells at various time points. In most cases around 9 hours of incubation are required. When the assay has progressed sufficiently, the supernatant from each well is removed and counted in a scintillation counter. The background counts (determined by the counts in the wells with no enzyme) are subtracted from each sample and the % release calculated in relation to the wells with enzyme only and no inhibitor. The triplicate values for each point are averaged and the data graphed as percent release versus drug concentration. IC$_{50}$'s are determined from the point at which 50% inhibition of release of radiolabeled collagen is obtained.

To determine the identity of the active collagenases in cartilage conditioned medium, assays were carried out using collagen as a substrate, cartilage conditioned medium containing collagenase activity and inhibitors of varying selectivity. The cartilage conditioned medium was collected during the time at which collagen degradation was occurring and thus is representative of the collagenases responsible for the collagen breakdown. Assays were carried out as outlined above except that instead of using recombinant MMP-13 or recombinant MMP-1, cartilage conditioned medium was the enzyme source.

IL-1 Induced Cartilage Collagen Degradation From Bovine Nasal Cartilage

This assay uses bovine nasal cartilage explants which are commonly used to test the efficacy of various compounds to inhibit either IL-1 induced proteoglycan degradation or IL-1 induced collagen degradation. Bovine nasal cartilage is a tissue that is very similar to articular cartilage, i.e. chondrocytes surrounded by a matrix that is primarily type 11 collagen and aggrecan. The tissue is used because it: (1) is very similar to articular cartilage, (2) is readily available, (3) is relatively homogeneous, and (4) degrades with predictable kinetics after IL-1 stimulation.

Two variations of this assay have been used to assay compounds. Both variations give similar data. The two variations are described below:

Variation 1

Three plugs of bovine nasal cartilage (approximately 2 mm diameter×1.5 mm long) are placed into each well of a 24 well tissue culture plate. One ml of serumless medium is then added to each well. Compounds are prepared as 10 mM stock solutions in DMSO and then diluted appropriately in serumless medium to final concentrations, e.g., 50, 500 and 5000 nM. Each concentration is assayed in triplicate.

Human recombinant IL-1α (5 ng/mL) (IL-1) is added to triplicate control wells and to each well containing drug. Triplicate control wells are also set up in which neither drug nor IL-1 are added. The medium is removed and fresh medium containing IL-1 and the appropriate drug concentrations is added on days 6, 12, 18 and 24 or every 3–4 days if necessary. The media removed at each time point is stored at −20° C. for later analysis. When the cartilage in the IL-1 alone wells has almost completely resorbed (about day 21), the experiment is terminated. The medium, is removed and stored. Aliquots (100 ul) from each well at each time point are pooled, digested with papain and then analyzed for hydroxyproline content. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot.

Variation 2

The experimental set-up is the same as outlined above in Variation 1, until day 12. On day 12, the conditioned medium from each well is removed and frozen. Then one ml of phosphate buffered saline (PBS) containing 0.5 µg/ml trypsin is added to each well and incubation continued for a further 48 hours at 37° C. After 48 hours incubation in trypsin, the PBS solution is removed. Aliquots (50 µl) of the PBS/trypsin solution and the previous two time points (days 6 and 12) are pooled, hydrolyzed and hydroxyproline content determined. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot. In this variation, the time course of the experiment is shortened considerably. The addition of trypsin for 48 hours after 12 days of IL-1 stimulation likely releases any type 11 collagen that has been damaged by collagenase activity but not yet released from the cartilage matrix. In the absence of IL-1 stimulation, trypsin treatment produces only low background levels of collagen degradation in the cartilage explants.

Inhibition of TNF Production

The ability of the compounds or the pharmaceutically acceptable salts thereof to inhibit the production of TNF and, consequently, demonstrate their effectiveness for treating diseases involving the production of TNF is shown by the following in vitro assay:

Human Monocyte Assay

Human mononuclear cells were isolated from anti-coagulated human blood using a one-step Ficoll-hypaque separation technique. (2) The mononuclear cells were washed three times in Hanks balanced salt solution (HBSS) with divalent cations and resuspended to a density of $2 \times 10^6$/ml in HBSS containing 1% BSA. Differential counts determined using the Abbott Cell Dyn 3500 analyzer indicated that monocytes ranged from 17 to 24% of the total cells in these preparations.

180 µl of the cell suspension was aliquoted into flat bottom 96 well plates (Costar). Additions of compounds and LPS (100 ng/ml final concentration) gave a final volume of 200 µl. All conditions were performed in triplicate. After a four hour incubation at 37° C. in an humidified $CO_2$ incubator, plates were removed and centrifuged (10 minutes at approximately 250×g) and the supernatants removed and assayed for TNFa using the R&D ELISA Kit.

Aggrecanase Assay

Primary porcine chondrocytes from articular joint cartilage are isolated by sequential trypsin and collagenase digestion followed by collagenase digestion overnight and are plated at $2 \times 10^5$ cells per well into 48 well plates with 5 µCi/ml$^{35}$S (1000 Ci/mmol) sulphur in type I collagen coated plates. Cells are allowed to incorporate label into their proteoglycan matrix (approximately 1 week) at 37° C., under an atmosphere of 5% $CO_2$.

The night before initiating the assay, chondrocyte monolayers are washed two times in DMEM/1% PSF/G and then allowed to incubate in fresh DMEM/1% FBS overnight.

The following morning chondrocytes are washed once in DMEM/1% PSF/G. The final wash is allowed to sit on the plates in the incubator while making dilutions.

Media and dilutions can be made as described in the Table below.

| | |
|---|---|
| Control Media | DMEM alone (control media) |
| IL-1 Media | DMEM + IL-1 (5 ng/ml) |
| Drug Dilutions | Make all compounds stocks at 10 mM in DMSO. Make a 100 uM stock of each compound in DMEM in 96 well plate. Store in freezer overnight. The next day perform serial dilutions in DMEM with IL-1 to 5 uM, 500 nM, and 50 nM. Aspirate final wash from wells and add 50 ul of compound from above dilutions to 450 ul of IL-1 media in appropriate wells of the 48 well plates. Final compound concentrations equal 500 nM, 50 nM, and 5 nM. All samples completed in triplicate with Control and IL-1 alone samples on each plate. |

Plates are labeled and only the interior 24 wells of the plate are used. On one of the plates, several columns are designated as IL-1 (no drug) and Control (no IL-1, no drug). These control columns are periodically counted to monitor 35S-proteoglycan release. Control and IL-1 media are added to wells (450 ul) followed by compound (50 ul) so as to initiate the assay. Plates are incubated at 37° C., with a 5% $CO_2$ atmosphere.

At 40–50% release (when CPM from IL-1 media is 4–5 times control media) as assessed by liquid scintillation counting (LSC) of media samples, the assay is terminated (9–12 hours). Media is removed from all wells and placed in scintillation tubes. Scintillate is added and radioactive counts are acquired (LSC). To solubilize cell layers, 500 µl of papain digestion buffer (0.2 M Tris, pH 7.0, 5 mM EDTA, 5 mM DTT, and 1 mg/ml papain) is added to each well. Plates with digestion solution are incubated at 60° C. overnight. The cell layer is removed from the plates the next day and placed in scintillation tubes. Scintillate is then added, and samples counted (LSC).

The percent of released counts from the total present in each well is determined. Averages of the triplicates are made with control background subtracted from each well. The percent of compound inhibition is based on IL-1 samples as 0% inhibition (100% of total counts).

IN VIVO ASSAYS

Female golden Syrian hamsters (*Mesocricetus auratus*) strain LAK.LVG(SYR) can be purchased from Charles River Laboratories (Kingston, N.Y.) at 100–110 g weight. They can be maintained on a 10/14 hr light/dark cycle with food and water ad libitum and acclimatized for approximately one week in standard housing before studies are initiated.

For induction of arthritis, groups of 6 hamsters arre anesthetized with sodium pentobarbital (80–100 mg/kg i.p.). Knees arre cleaned and injected intraarticularly with an arthritogen (40 ng of IL-1α or 2 µg activated MMP-1 in 20 µl of normal saline) through the patellar tendon into each knee joint using a 50 µl syringe fitted with a 30 gauge needle. Oral administration of a compound of formula I is performed either after a certain period (e.g.,3 hours IL-1) or is predosed (e.g., 2 hours before MMP-13 arthritogen injection). A control group was untreated. After an additional three hours, the hamsters are sacrificed with a sodium pentobarbital overdose and the synovial fluid lavaged. After surgically exposing the articular joint, three washes of 15 µl of saline are used to lavage the synovial fluid. The lavage fluid from both knees is pooled for each animal in a 500 µl conical tube and placed on ice. After centrifuging at 500×G to remove cells and debris, the samples can be frozen until assayed.

For IL-1, proteoglycan and hyaluronan can be determined on a 50 µl aliquot of the papain-digested synovial fluid. An aliquot is transferred to a 0.5 ml polypropylene microcentrifuge tube, and 200 µl of 50 mM phosphate buffer at pH 6.5, containing 1 mM EDTA, added. The sample is passed through a 30×0.78 cm TSK-GEL G5000PWXL column (TosoHass, Montgomeryville, Pa.) and the column effluent monitored at 206 nm. The first high molecular weight peak is hyaluronan. The sample is mixed post column with a solution containing 16 mg DMMB, 3.04 gm glycine, 2.37 gm sodium chloride, and 1.58 ml 6N HCl in 1 liter, and the amount of aggrecan read at 540 nm. Chondroitin sulfate is used as a standard for quantitation of aggrecan. The amount of aggrecan in a sample is expressed as µg/ml of chondroitin sulfate standard.

To determine the effect of a drug on aggrecanase induced inflammation, the average concentration of aggrecan in the drug treated group was compared to the amount of aggrecan in the untreated group and a percentage inhibition calculated for each drug.

For MMP-13 an aliquot of synovial fluid is assayed by ELISA using an anitbody to the neoepitope such as described in U.S. Pat. No. 6,030,792.

For determination of TACE inhibition, 15 rats are separated into 3 groups. Each rat is dosed with drug or vehicle. Sixty minutes later, each rat is anesthetized with halothane and injected with 0.05 ml of 200 ug/ml PG-PS (Lee Laboratories product lot#126633) using a 1 cc syringe with a 30 g needle into the synovial cavity of both knees. Ninety minutes later, the rats are sacrificed. Each knee joint is exposed by surgery and lavaged with 0.3 ml lavage solution in 0.1 ml aliquots. The lavage solution is suctioned off the joint with glass disposable pipettes. The lavage is put in separate labeled 0.3 ml microfuge tubes and put on ice. The tubes are spun at 6000 rpm for 10 minutes in an Eppendorf centrifuge 5402. A portion of the supernatant (200 ul) was pipetted off and put into fresh, labeled tubes and frozen at −20° C. until assayed for TNFα levels using an ELISA test.

The compounds of the present invention that were tested all have $IC_{50}$'s in at least one of the above assays of less than 100 µM preferably less than 100 nM. Certain preferred groups of compounds possess differential selectivity toward the various MMP's or ADAMs. One group of preferred compounds possess selective activity towards MMP-13 over MMP-1. Another preferred group of compounds possess selective aggrecanase activity over MMP-1. Another preferred group of compounds possess selective aggrecanase and MMP-13 activity over MMP-1. Another preferred group of compounds possess selective aggrecanase and MMP-13 activity over MMP-1 and TACE.

For administration to mammals, including humans, for the inhibition of matrix metalloproteinases or mammalian reprolysin (preferably inhibition of Aggrecanase), a variety of conventional routes may be used including orally, parenterally and topically. In general, the active compound will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The following Examples illustrate the preparation of the compounds of the present invention. Melting points are uncorrected. NMR data are reported in parts per million (δ) and are referenced to the deuterium lock signal from the sample solvent (deuteriodimethylsulfoxide unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

EXAMPLE 1

4-[4-(2-Chloro-benzyloxy)-benzenesulfonyl]-3-hydroxy-tetrahydro-pyran-3-carboxylic Acid Hydroxyamide Step 1: 4-Benzyloxy-benzenethiol Zinc dust (13.1 g) was added to a mixture of 4-Benzyloxy-benzenesulfonyl chloride (I) (10 g, 35.2 mmoles), sulfuric acid (26.2 g) and ice (78.6 g) at 0° C. The mixture was warmed to ambient temperature, stirred for 1 hour, refluxed for 2 hours and then cooled to ambient temperature. The mixture was extracted twice with ethyl acetate and the combined organic layers were dried over sodium sulfate, filtered and concentrated in vacuo to yield the title compound. $^1$H NMR (CDCl$_3$, 400 MHz) δ 5.03 (s, 2H), 6.89 (d, J=8.92 Hz, 2H), 7.38 (d, J=8.93 Hz, 2H), 7.3–7.4 (m, 5H).

Step 2: (3,7-Dioxa-bicyclo[4.1.0]hept-1-yl)-methanol

Tert-butyl hydroperoxide (5.5M, 4.73 mmoles) was added to a mixture of vanadyl acetoacetonate (0.058 g, 0.22 mmoles) and hydroxymethyldihydro-pyran (0.5 g, 4.38 mmoles) in 16.2 ml of toluene at 85° C. After stirring for 5 minutes, TLC showed the reaction to be complete. The mixture was diluted with ethyl acetate and washed with 1 M hydrochloric acid followed by a wash with a saturated sodium bicarbonate solution. The ethyl acetate layer was dried over sodium sulfate, filtered and concentrated in vacuo to yield a light yellow oil (0.4 g, 70%). $^1$H NMR (D$_6$ acetone, 400 MHz) δ 3.21 (bs, 1H), 3.36–3.42 (m, 2H), 3.48 (dd, J=6.64 Hz and 12.04 Hz, 1H), 3.6 (dd, J=5.61 Hz and 12.04 Hz, 1H), 3.74 (d, J=13.07 Hz, 1H), 3.87 (dd, J=5.6 Hz and 6.64 Hz, 1H), 4.02 (d, J=13.07 Hz, 1H).

Step 3: 4-(4-Benzyloxy-phenylsulfanyl)-3-hydroxymethyl-tetrahydro-pyran-3-ol

A mixture of benzyloxy benzenethiol (1.5 g, 11.5 mmoles) and 30 ml of THF at 0° C. was treated with sodium hydride (0.48 g, 11.9 mmoles). After stirring for 20 minutes, an additional 20 ml of THF was added to reduce viscosity. The mixture was then treated with the product from Step 2, above, (5.01 g, 23 mmoles), and was stirred for 2 hours at ambient temperature. The mixture was diluted with saturated ammonium chloride solution, and extracted three times with ethyl acetate. The organic layers where combined, dried with sodium sulfate, filtered and concentrated in vacuo. The residue was filtered through a pad of silica elute with 20% ethyl acetate in hexanes to remove the undesirable material, followed by ethyl acetate to elute the desired product. Concentration in vacuo yielded a colorless solid (2.6 g, 65%). $^1$H NMR (CDCl$_3$, 400 MHz) δ 1.70–1.79 (m, 1H), 2.0–2.08 (m, 1H), 2.2 (bs, 2H), 3.21 (dd, J=4.57 Hz and 9.14 Hz, 1H), 3.27 (d, J=11.63 Hz, 1H), 3.46–3.52 (m, 1H), 3.8 (dd, J=11.63 Hz and 15.79 Hz, 2H), 3.87–3.94 (m, 2H), 5.04 (s, 2H), 6.91 (d, J=9.14 Hz, 1H), 7.31–7.42 (m, 7H).

Step 4: 4-(4-Benzyloxy-benzenesulfonyl)-3-hydroxymethyl-tetrahydro-pyran-3-ol

Peracetic acid (5.8 g, 24.27 mmoles) was added to a mixture of the product from the previous step (2.8 g, 8.09 mmoles) and sodium acetate (5.7 g, 70 mmoles) in 42 ml of methylene chloride at ambient temperature. (Caution: exothermic reaction). After stirring for 2 hours, the mixture was diluted with water and saturated sodium bicarbonate solution, then extracted with three portions of ethyl acetate. The combined organic layers where combined, dried with sodium sulfate, filtered and concentrated in vacuo to yield the title compound (2.5 g, 85%). $^1$H NMR (CDCl$_3$, 400 MHz) δ 1.61 (bd, 1H), 1.97–2.08 (m, 2H), 3.03 (d, J=11.41 Hz, 1H), 3.27–3.36 (m, 2H), 3.90 (d, J=12.24 Hz, 1H), 4.02 (dd, J=4.89 Hz and 11.21 Hz, 1H), 4.06 (d, J=11.41 Hz, 1H), 4.32 (d, J=12.24 Hz, 1H), 7.10 (d, J=8.93 Hz, 1H), 7.3–7.44 (m, 5H), 7.81 (d, J=8.92 Hz, 1H).

Step 5: 4-(4-Hydroxy-benzenesulfonyl)-3-hydroxymethyl-tetrahydro-pyran-3-ol

A mixture of the product from the previous step (0.2 g, 0.53 mmoles) dissolved in 10 ml of methyl alcohol charged with 50 mg of palladium hydroxide on carbon, was shaken under a hydrogen atmosphere at 50 psi for 18 hours. The mixture was filtered through Celite® and concentrated in vacuo to yield the title compound (0.15 g, 98%).

Step 5: HNMR (CD$_3$OD) δ 1.76–1.77 (m, 1H), 1.94–2.04 (m, 1H), 2.94 (d, J=11.20 Hz, 1H), 3.40 (dd, J=2.80 Hz and 11.51 Hz, 1H), 3.50 (dd, J=4.36 Hz and 12.13 Hz, 1H), 3.97 (d, J=11.85 Hz, 1H), 3.98–4.02 (m, 1H), 4.13 (d, J=11.20 Hz, 1H), 4.19 (d, J=12.13 Hz, 1H), 6.99 (d, J=9.02 Hz, 2H), 7.77 (d, J=8.71 Hz, 2H).

Step 6: 4-[4-(2-Chloro-benzyloxy)-benzenesulfonyl]-3-hydroxy-tetrahydro-pyran-3-carboxylic Acid To a mixture of the product from the previous step (115 mg, 0.4 mmoles) and cesium carbonate (260 mg, 0.8 mmoles) in 1 ml DMF at ambient temperature was added 2-chlorobenzyl bromide (98 mg, 0.48 mmoles). After stirring for 18 hours the mixture was diluted with 1 M hydrochloric acid and extracted with ethyl acetate. The organic layer was dried with sodium sulfate, filtered and concentrated in vacuo. The residue was dissolved in 2 ml of acetonitrile and 1.5 ml of pH 7 phosphate buffer then added at ambient temperature in the following order, sodium chlorite 80% (0.8 mmoles), TEMPO (4 mg, 0.03 mmoles), and sodium hypochlorite 4% solution (0.22 ml, 0.1 mmoles).

The reaction mixture was heated to 35° C. for 3 hours, then removed heat and stirred an additional 18 hours. The reaction mixture was then quenched with 1N sodium hydroxide and some solid sodium sulfite. The mixture was poured into ether and extracted twice with 1 N sodium hydroxide. The combined aqueous layers were acidified with 6N hydrochloric acid and then extracted 3 times with ethyl acetate. The ethyl acetate layers were combined, dried with sodium sulfate, filtered and concentrated in vacuo to yield the title compound (165 mg, 97%).

Step 6: HMNR (CD$_3$OD) δ 2.01–2.03 (m, 1H), 2.43–2.61 (m, 1H), 3.21 (d, J=11.51 Hz, 1H), 3.41–3.56 (m, 1H), 3.63 (dd, J=4.98 Hz and 12.75 Hz, 1H), 3.83 (d, J=11.82 Hz, 1H), 4.08–4.13 (m, 1H), 5.30 (s, 2H), 7.21 (d, J =9.02 Hz, 2H), 7.35–7.38 (m, 2H), 7.47–7.51 (m, 1H), 7.57–7.60 (m, 1H), 7.88 (d, J=9.02 Hz, 2H).

Step 7: 4-[4-(2-Chloro-benzyloxy)-benzenesulfonyl]-3-hydroxy-tetrahydro-pyran-3-carboxylic Acid Hydroxyamide To a mixture of the product from the previous step (160 mg, 0.4 mmoles), 1-hydroxybenzotriazole hydrate (76 mg, 0.6 mmoles), allyl hydroxylamine hydrochloride (62 mg, 0.6 mmoles), diisopropylethylamine (0.13 ml, 0.7 mmoles) in 2 ml of anhydrous methylene chloride at room temperature, was added 1-(3-dimethylaminopropyl)-3-ethylcarbodiimide (EDCI). After stirring for 48 hours, the mixture was diluted with ethyl acetate, washed with 1 M hydrochloric acid, sodium bicarbonate solution and brine, dried over anhydrous sodium sulfate, filtered and concentrated in vacuo. The residue was dissolved in 4 ml of 20% water in acetonitrile and was treated with 1.6 g of 5:2 (v/v) formic acid-triethylamine and 44 mg of tetrakis(triphenylphosphine) palladium(0) (Pd(PPh$_3$)$_4$). After being shaken at 85° C. for 30 minutes, the mixture was diluted with ether and extracted 4 times into 1 M sodium hydroxide. The combined aqueous layers were washed 3 times with ether, acidified to pH 1 with 6M hydrochloric acid and were extracted 3 times into ethyl acetate. The combined ethyl acetate extracts were dried over sodium sulfate, filtered and concentrated in vacuo. The compound was purified by preparative TLC plate eluting with 10% methanol in methylene chloride. The silica was washed with 20% methanol in methylene chloride with 1% acetic acid, the filtrate concentrated in vacuo. After trituration and collection with isopropyl ether the product was isolated as a colorless solid (30 mg, 18%).

Step 7: HMNR (CD$_3$OD) δ 1.92–1.96 (m, 1H), 2.54–2.60 (m, 1H), 3.22 (d, J=11.51 Hz, 1H), 3.41–3.49 (m, 1H), 3.56 (dd, J=4.35 Hz and 12.75 Hz, 1H), 3.86 (d, J=11.50 Hz, 1H), 4.10 (dd, J=4.98 Hz and 11.20 Hz, 1H), 5.31 (s, 2H), 7.23 (d, J=8.71 Hz, 2H), 7.36–7.39 (m, 2H), 7.47–7.48 (m, 1H), 7.58–7.6 (m, 1H), 7.90 (d, J=8.71 Hz, 2H).

The compounds of Table 1 were prepared by the method of Example 1 substituting the appropriate benzyl halide in step 6.

TABLE 1

| Example | Structure | Name | Yield (%) | Mass Spec ([M + H]$^+$) |
|---|---|---|---|---|
| 2 | 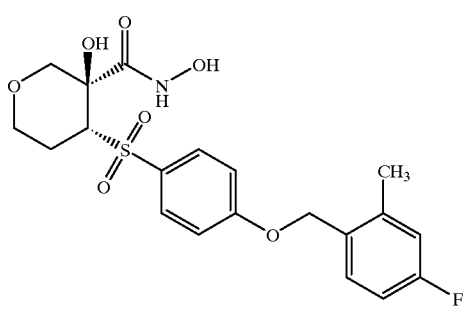 | 4-[4-(4-Fluoro-2-methyl-benzyloxy)-benzenesulfonyl]-3-hydroxy-tetrahydro-pyran-3-carboxylic acid hydroxyamide | 25 | 440 |
| 3 | 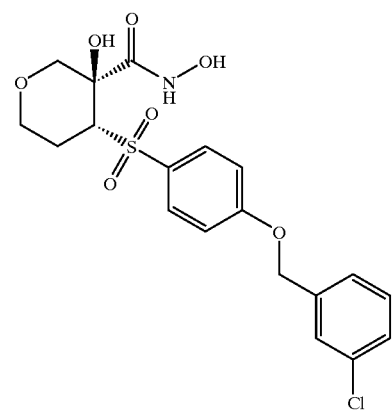 | 4-[4-(3-Chloro-benzyloxy)-benzenesulfonyl]-3-hydroxy-tetrahydro-pyran-3-carboxylic acid hydroxyamide | 13 | 442 |

TABLE 1-continued

| Example | Structure | Name | Yield (%) | Mass Spec ([M + H]+) |
|---------|-----------|------|-----------|----------------------|
| 4 | 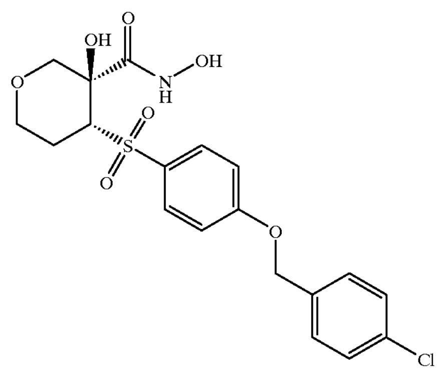 | 4-[4-(4-Chloro-benzyloxy)-benzenesulfonyl]-3-hydroxy-tetrahydro-pyran-3-carboxylic acid hydroxyamide | 14 | 442 |
| 5 | 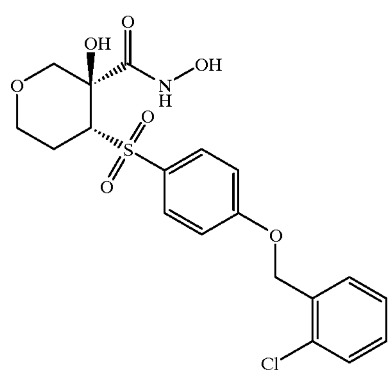 | 4-[4-(2-Chloro-benzyloxy)-benzenesulfonyl]-3-hydroxy-tetrahydro-pyran-3-carboxylic acid hydroxyamide | 17 | 442 |
| 6 | 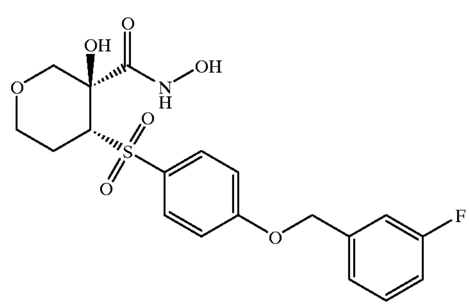 | 4-[4-(3-Fluoro-benzyloxy)-benzenesulfonyl]-3-hydroxy-tetrahydro-pyran-3-carboxylic acid hydroxyamide | 18 | 426 |
| 7 | 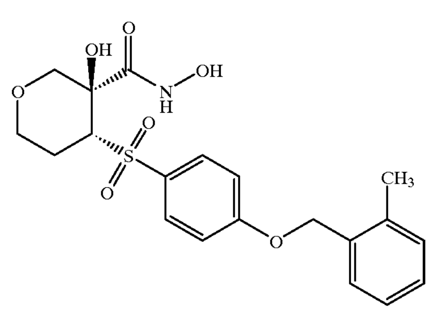 | 3-Hydroxy-4-[4-(2-methyl-benzyloxy)-benzenesulfonyl]-tetrahydro-pyran-3-carboxylic acid hydroxyamide | 34 | 422 |

TABLE 1-continued

| Example | Structure | Name | Yield (%) | Mass Spec ([M + H]⁺) |
|---|---|---|---|---|
| 8 | 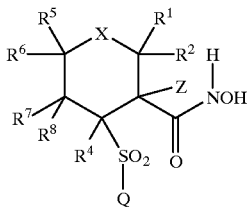 | 4-[4-(4-Fluoro-2-methyl-benzyloxy)-benzenesulfonyl]-3-hydroxy-tetrahydro-pyran-3-carboxylic acid hydroxyamide | 46 | 440 |

What is claimed is:

1. A compound of the formula $$\text{I}$$

or a pharmaceutically acceptable salt thereof, wherein

X is oxygen;

Z is $-OR^{11}$, $-NR^{12}R^{13}$ or $(C_1-C_6)$alkyl optionally substituted with one to three substituents independently selected from the group consisting of halo, hydroxy, $-CN$, $(C_1-C_6)$alkyl, $(C_2-C_6)$alkenyl, $(C_6-C_{10})$aryl $(C_2-C_6)$alkenyl, $(C_1-C_9)$heteroaryl$(C_2-C_6)$alkenyl, $(C_2-C_6)$alkynyl, $(C_6-C_{10})$aryl$(C_2-C_6)$alkynyl, $(C_1-C_9)$heteroaryl$(C_2-C_6)$alkynyl, amino, $(C_1-C_6)$alkylamino, $[(C_1-C_6)$alkyl$]_2$amino, mercapto, $(C_1-C_6)$alkylthio, $(C_1-C_6)$alkoxy, perfluoro$(C_1-C_6)$alkyl, perfluoro$(C_1-C_6)$alkoxy, $(C_6-C_{10})$aryl, $(C_1-C_9)$heteroaryl, $(C_3-C_9)$heterocyclic, $(C_3-C_9)$cycloalkyl, $(C_6-C_{10})$arylamino, $(C_6-C_{10})$arylthio, $(C_6-C_{10})$aryloxy, $(C_1-C_9)$heteroarylamino, $(C_1-C_9)$heteroarylthio, $(C_1-C_9)$heteroaryloxy, $(C_3-C_9)$heterocyclic-amino, $(C_3-C_9)$heterocyclic-S—, $(C_3-C_9)$heterocyclic-O—, $(C_3-C_9)$cycloalkylamino, $(C_3-C_9)$cycloalkyl-S—, $(C_3-C_9)$cycloalkyl-O—, $(C_1-C_6)$alkyl-$(C=O)$—, $(C_1-C_6)$alkyl-$(C=O)$—NH—, $(C_1-C_6)$alkyl-$(C=O)$—S—, $(C_1-C_6)$alkyl-$(C=O)$—O—, $(C_1-C_6)$alkoxy-$(C=O)$—, $-CO_2H$, $H_2N-(C=O)$—, $(C_1-C_6)$alkyl-NH—$(C=O)$— and $[(C_1-C_6)$alkyl$]_2$-N—$(C=O)$—;

$R^1$, $R^2$, $R^5$ and $R^6$ are each independently selected from the group consisting of hydrogen, $-CN$, $(C_1-C_6)$alkyl, $(C_2-C_6)$alkenyl, $(C_6-C_{10})$aryl$(C_2-C_6)$alkenyl, $(C_1-C_9)$heteroaryl$(C_2-C_6)$alkenyl, $(C_2-C_6)$alkynyl, $(C_6-C_{10})$aryl$(C_2-C_6)$alkynyl, $(C_1-C_9)$heteroaryl$(C_2-C_6)$alkynyl, perfluoro$(C_1-C_6)$alkyl, $(C_6-C_{10})$aryl, $(C_1-C_9)$heteroaryl, $(C_3-C_9)$cycloalkyl, $(C_3-C_9)$heterocyclic, $(C_1-C_6)$alkyl$(C=O)$—, $(C_1-C_6)$alkoxy-$(C=O)$—, $-CO_2H$, $H_2N-(C=O)$—, $(C_1-C_6)$alkyl-NH—$(C=O)$— and $[(C_1-C_6)$alkyl$]_2$-N—$(C=O)$—;

wherein said $R^1$, $R^2$, $R^5$ and $R^6$ $(C_1-C_6)$alkyl groups are each independently optionally substituted by one to three groups selected from halo, trifluoromethyl, hydroxy, amino, $-CN$, $(C_1-C_6)$alkylthio, $(C_1-C_6)$alkoxy, $(C_6-C_{10})$aryl, $(C_1-C_9)$heteroaryl, $(C_3-C_6)$cycloalkyl, $(C_3-C_9)$heterocyclic, $(C_6-C_{10})$arylamino, $(C_6-C_{10})$arylthio, $(C_6-C_{10})$aryloxy, $(C_1-C_9)$heteroarylamino,$(C_1-C_9)$heteroarylthio, $(C_1-C_9)$heteroaryloxy, $(C_3-C_9)$heterocyclic-amino, $(C_3-C_9)$heterocyclic-S—,$(C_3-C_9)$heterocyclic-O—, $(C_3-C_9)$cycloalkylamino, $(C_3-C_9)$cycloalkyl-S—, $(C_3-C_9)$cycloalkyl-O—,$(C_6-C_{10})$aryl$(C_1-C_2)$alkoxy, $(C_1-C_9)$heteroaryl$(C_1-C_2)$alkoxy, $(C_1-C_6)$alkyl-$(C=O)$—NH—, $(C_1-C_6)$alkyl-$(C=O)$—S—, $(C_1-C_6)$alkyl-$(C=O)$—O—, $(C_1-C_6)$alkylsulfinyl, $(C_6-C_{10})$arylsulfinyl, $(C_1-C_6)$alkylsulfonyl, $(C_6-C_{10})$arylsulfonyl, $(C_1-C_6)$alkylamino, or $((C_1-C_6)$alkyl$)_2$amino;

$R^3$ is hydrogen; $(C_1-C_6)$alkyl optionally substituted by one or more of $-CN$, perfluoro$(C_1-C_6)$alkyl, $(C_6-C_{10})$aryl, $(C_3-C_6)$cycloalkyl, $(C_1-C_6)$alkyl$(C=O)$—, $(C_1-C_6)$alkoxy-$(C=O)$—, $-CO_2H$, $(C_1-C_6)$alkyl-NH—$(C=O)$—, and $[(C_1-C_6)$alkyl$]_2$-N—$(C=O)$—; $(C_6-C_{10})$arylsulfonyl; $(C_1-C_6)$alkylsulfonyl; $(C_1-C_6)$alkyl-NH—$(C=O)$—; $[(C_1-C_6)$alkyl$]_2$-N—$(C=O)$—; or $(R^{10}R^9N)$—$(C=O)$— wherein $R^9$ and $R^{10}$ are taken together with the nitrogen to which they are attached to form a ring selected from azetidinyl, pyrrolidinyl, piperidinyl, morpholinyl and thiomorpholinyl;

$R^4$ is hydrogen or $(C_1-C_4)$alkyl;

$R^7$ and $R^8$ are each independently selected from the group consisting of hydrogen, hydroxy, halo, $-CN$, $(C_1-C_9)$alkyl, $(C_2-C_6)$alkenyl, $(C_2-C_6)$alkynyl, amino, $(C_1-C_6)$alkylamino, $[(C_1-C_6)$alkyl$]_2$amino, $(C_1-C_6)$alkylthio, $(C_1-C_6)$alkoxy, perfluoro$(C_1-C_6)$alkyl, perfluoro$(C_1-C_6)$alkoxy, $(C_3-C_6)$cycloalkyl, $(C_6-C_{10})$aryl, $(C_3-C_9)$heterocyclic, $(C_1-C_9)$heteroaryl, $(C_6-C_{10})$arylamino, $(C_6-C_{10})$arylthio, $(C_6-C_{10})$aryloxy, $(C_1-C_9)$heteroarylamino, $(C_1-C_9)$heteroarylthio, $(C_1-C_9)$heteroaryloxy, $(C_3-C_9)$heterocyclic-amino, $(C_3-C_9)$heterocyclic-S—, $C_3-C_9)$heterocyclic-O—,$(C_3-C_9)$cycloalkylamino, $(C_3-C_9)$cycloalkyl-S—, $(C_3-C_9)$cycloalkyl-O—, $(C_1-C_9)$aryl$(C_2-C_6)$alkenyl, $(C_1-C_9)$heteroaryl$(C_2-C_6)$alkenyl, $(C_6-C_{10})$aryl$(C_2-C_6)$alkynyl, $(C_1-C_9)$heteroaryl$(C_2-C_6)$alkynyl, $(C_1-C_6)$alkyl$(C=O)$—, $(C_1-C_6)$alkyl$(C=O)$—NH—, $(C_1-C_6)$alkyl$(C=O)$—S—, $(C_1-C_6)$ alkyl(C=O)—O—, ($C_1$-$C_6$)alkoxy-(C=O)—, —$CO_2$H, $H_2$N—(C=O)—, ($C_1$-$C_6$)alkyl-NH—(C=O)— and [($C_1$-$C_9$)alkyl]$_2$-N—(C=O)—;

wherein each of said $R^7$ and $R^8$ ($C_1$-$C_6$)alkyl group are independently optionally substituted by one to three substituents independently selected from halo, hydroxy, —CN, ($C_1$-$C_6$)alkoxy, ($C_1$-$C_6$)alkylthio, trifluoromethyl, ($C_3$-$C_6$)cycloalkyl, ($C_6$-$C_{10}$)aryl, ($C_3$-$C_9$)heterocyclic,($C_1$-$C_9$)heteroaryl, ($C_6$-$C_{10}$) arylamino, ($C_6$-$C_1$)arylthio, ($C_6$-$C_{10}$)aryloxy, ($C_1$-$C_9$) heteroarylamino,($C_1$-$C_9$)heteroarylthio, ($C_1$-$C_9$) heteroaryloxy, ($C_3$-$C_9$)heterocyclic-amino, ($C_3$-$C_9$) heterocyclic-S—,($C_3$-$C_9$)heterocyclic-O—, ($C_3$-$C_9$) cycloalkylamino, ($C_3$-$C_9$)cycloalkyl-S—, ($C_3$-$C_9$) cycloalkyl-O—,($C_6$-$C_{10}$)aryl($C_1$-$C_2$)alkoxy, ($C_1$-$C_9$) heteroaryl($C_1$-$C_2$)alkoxy, ($C_1$-$C_6$)alkyl(C=O)—NH—, ($C_1$-$C_6$)alkyl(C=O)—S—, ($C_1$-$C_6$)alkyl (C=O)—O—, ($C_1$-$C_6$)alkylsulfinyl, ($C_6$-$C_{10}$) arylsulfinyl, ($C_1$-$C_6$)alkylsulfonyl, ($C_6$-$C_{10}$) arylsulfonyl, amino, ($C_1$-$C_6$)alkylamino and (($C_1$-$C_6$) alkyl)$_2$amino;

or $R^1$ and $R^2$, $R^5$ and $R^6$ or $R^7$ and $R^8$ may be taken together to form a carbonyl group or an optionally substituted ($C_3$-$C_6$)cycloalkyl ring optionally containing 1 or 2 heteroatoms; wherein said heteroatoms may be selected from the group consisting of —S—, —O— or >NH or >N($C_1$-$C_6$)alkyl; and said optional substituents (i.e. 1–3 substituents per ring) may be selected from ($C_1$-$C_4$)alkyl, fluoro, chloro, hydroxy, ($C_1$-$C_4$) alkoxy and —$NR^{14}R^{15}$;

or $R^5$ and $R^7$, $R^5$ and $R^8$, $R^6$ and $R^7$ or $R^6$ and $R^8$ may be taken together to form an optionally substituted ($C_4$-$C_6$)cycloalkyl ring optionally containing 1 or 2 heteroatoms; wherein said heteroatoms may be selected from the group consisting of —S—, —O— or >NH or >N($C_1$-$C_6$)alkyl; and said optional substituents (i.e. 1–3 substituents) may be selected from ($C_1$-$C_4$)alkyl, fluoro, chloro, hydroxy, ($C_1$-$C_4$)alkoxy and —$NR^{14}R^{15}$;

$R^{11}$ is hydrogen, ($C_1$-$C_6$)alkyl, ($C_2$-$C_6$)alkenyl, ($C_6$-$C_{10}$) aryl($C_2$-$C_6$)alkenyl, ($C_2$-$C_9$)heteroaryl($C_2$-$C_6$) alkenyl, ($C_2$-$C_6$)alkynyl, ($C_6$-$C_{10}$)aryl($C_2$-$C_6$)alkynyl, ($C_1$-$C_9$)heteroaryl($C_2$-$C_6$)alkynyl, perfluoro($C_1$-$C_6$) alkyl, ($C_6$-$C_{10}$)aryl, ($C_1$-$C_9$)heteroaryl, ($C_3$-$C_6$) cycloalkyl, ($C_3$-$C_9$)heterocyclic, ($C_1$-$C_6$)alkyl-(C=O)—, ($C_1$-$C_6$)alkoxy-(C=O)—, ($C_1$-$C_6$)alkyl-NH—(C=O)— and [($C_1$-$C_6$) alkyl]$_2$-N—(C=O)—;

$R^{12}$ is hydrogen, ($C_1$-$C_6$)alkyl, ($C_2$-$C_6$)alkenyl, ($C_1$-$C_{10}$) aryl($C_2$-$C_6$)alkenyl, ($C_1$-$C_9$)heteroaryl($C_2$-$C_6$) alkenyl, ($C_2$-$C_6$)alkynyl, ($C_6$-$C_{10}$)aryl($C_2$-$C_6$)alkynyl, ($C_1$-$C_9$)heteroaryl($C_2$-$C_6$)alkynyl, perfluoro($C_1$-$C_6$) alkyl, ($C_6$-$C_{10}$)aryl, ($C_1$-$C_9$)heteroaryl, ($C_3$-$C_6$) cycloalkyl, ($C_3$-$C_9$)heterocyclic, ($C_1$-$C_6$)alkyl-(C=O)—, ($C_1$-$C_6$)alkoxy-(C=O)—, $H_2$N—(C=O)—, ($C_1$-$C_6$)alkyl-NH—(C=O)— and [($C_1$-$C_6$)alkyl]$_2$-N—(C=O)—;

$R^{13}$ is hydrogen, ($C_1$-$C_6$)alkyl, ($C_2$-$C_6$)alkenyl, ($C_6$-$C_{10}$) aryl($C_2$-$C_6$)alkenyl, ($C_1$-$C_9$)heteroaryl($C_2$-$C_6$) alkenyl, ($C_2$-$C_6$)alkynyl, ($C_6$-$C_{10}$)aryl($C_2$-$C_6$)alkynyl, ($C_1$-$C_9$)heteroaryl($C_2$-$C_6$)alkynyl, perfluoro($C_1$-$C_6$) alkyl, ($C_6$-$C_{10}$)aryl, ($C_1$-$C_9$)heteroaryl, ($C_3$-$C_6$) cycloalkyl or ($C_3$-$C_9$)heterocyclic;

$R^{14}$ is hydrogen, ($C_1$-$C_6$)alkyl, ($C_2$-$C_6$)alkenyl, ($C_1$-$C_{10}$) aryl($C_2$-$C_6$)alkenyl, ($C_1$-$C_9$)heteroaryl($C_2$-$C_6$) alkenyl, ($C_2$-$C_6$)alkynyl, ($C_6$-$C_{10}$)aryl($C_2$-$C_6$)alkynyl, ($C_1$-$C_9$)heteroaryl($C_2$-$C_6$)alkynyl, perfluoro($C_1$-$C_6$) alkyl, ($C_6$-$C_{10}$)aryl, ($C_1$-$C_9$)heteroaryl, ($C_3$-$C_6$) cycloalkyl, ($C_3$-$C_9$)heterocyclic, ($C_1$-$C_6$)alkyl-(C=O)—, ($C_1$-$C_6$)alkoxy-(C=O)—, $H_2$N—(C=O)—, ($C_1$-$C_6$)alkyl-NH—(C=O)— and [($C_1$-$C_6$)alkyl]$_2$-N—(C=O)—;

$R^{15}$ is hydrogen, ($C_1$-$C_6$)alkyl, ($C_2$-$C_6$)alkenyl, ($C_6$-$C_{10}$) aryl($C_2$-$C_6$)alkenyl, ($C_1$-$C_9$)heteroaryl($C_2$-$C_6$) alkenyl, ($C_2$-$C_6$)alkynyl, ($C_6$-$C_{10}$)aryl($C_2$-$C_6$)alkynyl, ($C_1$-$C_9$)heteroaryl($C_2$-$C_6$)alkynyl, perfluoro($C_1$-$C_6$) alkyl, ($C_6$-$C_{10}$)aryl, ($C_1$-$C_9$)heteroaryl, ($C_3$-$C_6$) cycloalkyl or ($C_3$-$C_9$)heterocyclic;

Q is ($C_1$-$C_9$)alkyl, ($C_6$-$C_{10}$)aryl, ($C_1$-$C_9$)heteroaryl, ($C_3$-$C_9$)heterocyclic, ($C_6$-$C_{10}$)aryl($C_1$-$C_6$)alkyl, ($C_1$-$C_9$)heteroaryl($C_1$-$C_6$)alkyl, ($C_3$-$C_9$)heterocyclic ($C_1$-$C_6$)alkyl, ($C_6$-$C_{10}$)aryl($C_6$-$C_{10}$)aryl, ($C_6$-$C_{10}$)aryl ($C_1$-$C_9$)heteroaryl, ($C_6$-$C_{10}$)aryl($C_3$-$C_9$)heterocyclic, ($C_1$-$C_9$)heteroaryl($C_6$-$C_{10}$)aryl, ($C_1$-$C_9$)heteroaryl ($C_1$-$C_9$)heteroaryl, ($C_1$-$C_9$)heteroaryl($C_3$-$C_9$) heterocyclic, ($C_3$-$C_9$)heterocyclic($C_1$-$C_{10}$)aryl, ($C_3$-$C_9$)heterocyclic($C_1$-$C_9$)heteroaryl, ($C_3$-$C_9$) heterocyclic($C_3$-$C_9$)heterocyclic, ($C_6$-$C_{10}$)aryloxy ($C_1$-$C_9$)alkyl, ($C_6$-$C_{10}$)aryloxy($C_6$-$C_{10}$)aryl, ($C_6$-$C_{10}$) aryloxy($C_1$-$C_9$)heteroaryl, ($C_6$-$C_{10}$)aryloxy($C_3$-$C_9$) heterocyclic, ($C_1$-$C_9$)heteroaryloxy($C_1$-$C_6$)alkyl, ($C_1$-$C_9$)heteroaryloxy($C_6$-$C_{10}$)aryl, ($C_1$-$C_9$) heteroaryloxy($C_1$-$C_9$)heteroaryl, ($C_1$-$C_9$) heteroaryloxy($C_3$-$C_9$)heterocyclic, ($C_3$-$C_9$) heterocyclic-O—($C_1$-$C_6$)alkyl, ($C_3$-$C_9$)heterocyclic-O—($C_6$-$C_{10}$)aryl, ($C_3$-$C_9$)heterocyclic-O—($C_1$-$C_9$) heteroaryl, ($C_3$-$C_9$)heterocyclic-O—($C_3$-$C_9$) heterocyclic, ($C_6$-$C_{10}$)aryl($C_1$-$C_6$)alkyl($C_6$-$C_{10}$)aryl, ($C_6$-$C_{10}$)aryl($C_1$-$C_6$)alkyl($C_1$-$C_9$)heteroaryl, ($C_6$-$C_{10}$) aryl($C_1$-$C_6$)alkyl($C_3$-$C_9$)heterocyclic, ($C_6$-$C_{10}$)aryl ($C_1$-$C_6$)alkoxy($C_6$-$C_{10}$)aryl, ($C_6$-$C_{10}$)aryl($C_1$-$C_6$) alkoxy($C_1$-$C_9$)heteroaryl, ($C_6$-$C_{10}$)aryl($C_1$-$C_6$)alkoxy ($C_3$-$C_9$)heterocyclic, ($C_6$-$C_{10}$)aryloxy($C_1$-$C_6$)alkyl ($C_6$-$C_{10}$)aryl, ($C_6$-$C_{10}$)aryloxy($C_1$-$C_6$)alkyl($C_1$-$C_9$) heteroaryl, ($C_6$-$C_{10}$)aryloxy($C_1$-$C_6$)alkyl($C_3$-$C_9$) heterocyclic, ($C_1$-$C_9$)heteroaryl($C_1$-$C_6$)alkyl($C_6$-$C_{10}$) aryl, ($C_1$-$C_9$)heteroaryl($C_1$-$C_6$)alkyl($C_1$-$C_9$) heteroaryl, ($C_1$-$C_9$)heteroaryl($C_1$-$C_6$)alkyl($C_3$-$C_9$) heterocyclic, ($C_1$-$C_9$)heteroaryl($C_1$-$C_6$)alkoxy ($C_6$-$C_{10}$)aryl, ($C_1$-$C_9$)heteroaryl($C_1$-$C_9$)alkoxy ($C_1$-$C_9$)heteroaryl, ($C_1$-$C_9$)heteroaryl($C_1$-$C_6$)alkoxy ($C_3$-$C_9$)heterocyclic, ($C_1$-$C_9$)heteroaryloxy($C_1$-$C_6$) alkyl($C_6$-$C_{10}$)aryl, ($C_1$-$C_9$)heteroaryloxy($C_1$-$C_6$)alkyl ($C_1$-$C_9$)heteroaryl, ($C_1$-$C_9$)heteroaryloxy($C_1$-$C_6$)alkyl ($C_3$-$C_9$)heterocyclic, ($C_3$-$C_9$)heterocyclic($C_1$-$C_6$) alkyl($C_6$-$C_{10}$)aryl, ($C_3$-$C_9$)heterocyclic($C_1$-$C_6$)alkyl ($C_1$-$C_9$)heteroaryl, ($C_3$-$C_9$)heterocyclic($C_1$-$C_6$)alkyl ($C_3$-$C_9$)heterocyclic, ($C_3$-$C_9$)heterocyclic($C_1$-$C_6$) alkoxy($C_6$-$C_1$-$C_9$)aryl, ($C_3$-$C_9$)heterocyclic($C_1$-$C_6$) alkoxy($C_1$-$C_9$)heteroaryl, ($C_3$-$C_9$)heterocyclic($C_1$-$C_6$) alkoxy($C_3$-$C_9$)heterocyclic, ($C_3$-$C_9$)heterocyclic-O—($C_1$-$C_6$)alkyl($C_1$-$C_{10}$)aryl, ($C_3$-$C_9$)heterocyclic-O—($C_1$-$C_6$)alkyl($C_1$-$C_9$)heteroaryl, ($C_3$-$C_9$)heterocyclic-O—($C_1$-$C_6$)alkyl($C_3$-$C_9$)heterocyclic, ($C_6$-$C_{10}$)aryl ($C_6$-$C_{10}$)aryl($C_1$-$C_6$)alkyl, ($C_6$-$C_{10}$)aryl-NH—($C_1$-$C_6$)alkyl, ($C_6$-$C_{10}$)aryl-NH—($C_6$-$C_{10}$)aryl, ($C_6$-$C_{10}$)aryl-NH—($C_1$-$C_9$)heteroaryl, ($C_6$-$C_{10}$)aryl-NH—($C_3$-$C_9$)heterocyclic, ($C_1$-$C_9$)heteroaryl-NH—($C_1$-$C_6$)alkyl, ($C_1$-$C_9$)heteroaryl-NH—($C_6$-$C_{10}$)aryl, ($C_1$-$C_9$)heteroaryl-NH—($C_1$-$C_9$)heteroaryl, ($C_1$-$C_9$) heteroaryl-NH—($C_3$-$C_9$)heterocyclic, ($C_3$-$C_9$) heterocyclic-NH—($C_1$-$C_6$)alkyl, ($C_3$-$C_9$)heterocyclic-NH—($C_6$-$C_{10}$)aryl, ($C_3$-$C_9$)heterocyclic-NH—($C_1$-$C_9$)heteroaryl, ($C_3$-$C_9$)heterocyclic-NH—($C_3$-$C_9$)

heterocyclic, $(C_6-C_{10})$aryl$(C_1-C_6)$alkyl-NH—$(C_6-C_{10})$aryl, $(C_6-C_{10})$aryl$(C_1-C_6)$alkyl-NH—$(C_1-C_9)$heteroaryl, $(C_6-C_{10})$aryl$(C_1-C_6)$alkyl-NH—$(C_3-C_9)$heterocyclic, $(C_6-C_{10})$aryl-NH—$(C_1-C_6)$alkyl$(C_6-C_{10})$aryl, $(C_6-C_{10})$aryl-NH—$(C_1-C_6)$alkyl$(C_1-C_9)$heteroaryl, $(C_6-C_{10})$aryl-NH—$(C_1-C_6)$alkyl$(C_3-C_9)$heterocyclic, $(C_1-C_9)$heteroaryl$(C_1-C_9)$alkyl-NH—$(C_6-C_{10})$aryl, $(C_1-C_9)$heteroaryl$(C_1-C_6)$alkyl-NH—$(C_1-C_9)$heteroaryl, $(C_1-C_9)$heteroaryl$(C_1-C_6)$alkyl-NH—$(C_3-C_9)$heterocyclic, $(C_1-C_9)$heteroaryl-NH—$(C_1-C_6)$alkyl$(C_6-C_{10})$aryl, $(C_1-C_9)$heteroaryl-NH—$(C_1-C_6)$alkyl$(C_1-C_9)$heteroaryl, $(C_1-C_9)$heteroaryl-NH—$(C_1-C_6)$alkyl$(C_3-C_9)$heterocyclic, $(C_3-C_9)$heterocyclic$(C_1-C_6)$alkyl-NH—$(C_6-C_{10})$aryl, $(C_3-C_9)$heterocyclic$(C_1-C_6)$alkyl-NH—$(C_1-C_9)$heteroaryl, $(C_3-C_9)$heterocyclic$(C_1-C_6)$alkyl-NH—$(C_3-C_9)$heterocyclic, $(C_3-C_9)$heterocyclic-NH—$(C_1-C_6)$alkyl$(C_6-C_{10})$aryl, $(C_3-C_9)$heterocyclic-NH—$(C_1-C_6)$alkyl$(C_1-C_9)$heteroaryl, $(C_3-C_9)$heterocyclic-NH—$(C_1-C_6)$alkyl$(C_3-C_9)$heterocyclic, $(C_6-C_{10})$aryl$(C_1-C_6)$alkyl-NH—$(C_1-C_6)$alkyl or $(C_6-C_{10})$aryl$(C_1-C_6)$alkoxy$(C_1-C_6)$alkyl, wherein each of said $(C_6-C_{10})$aryl, $(C_1-C_9)$heteroaryl or $(C_3-C_9)$heterocyclic groups may optionally be substituted by one or more substituents, independently selected from the group consisting of halo, —CN, $(C_1-C_6)$alkyl optionally substituted with one or more fluorine atoms, hydroxy, hydroxy-$(C_1-C_6)$alkyl, $(C_1-C_6)$alkoxy optionally substituted with one or more fluorine atoms, $(C_1-C_6)$alkoxy$(C_1-C_6)$alkyl, HO—(C=O)—,$(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—,$(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_9)$alkyl(O=C)—$(C_1-C_6)$alkyl, $NO_2$, amino, $(C_1-C_6)$alkylamino, $[(C_1-C_9)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_9)$alkyl, H(O=C)—NH—, $(C_1-C_6)$alkyl(C=O)—NH, $(C_1-C_6)$alkyl(C=O)— [NH]$(C_1-C_6)$alkyl, $(C_1-C_6)$alkyl(C=O)— [N$(C_1-C_6)$alkyl]$(C_1-C_6)$alkyl, $(C_1-C_6)$alkyl-S—$(C_1-C_6)$alkyl-(S=O)—, $(C_1-C_6)$alkyl-$SO_2$—, $(C_1-C_6)$alkyl-$SO_2$—NH—, $(C_1-C_6)$alkyl-$SO_2$-[N—$(C_1-C_6)$alkyl]-, $H_2N$—$SO_2$—, $H_2N$—$SO_2$—$(C_1-C_6)$alkyl, $(C_1-C_6)$alkyl HN—$SO_2$—$(C_1-C_6)$alkyl, $[(C_1-C_9)$alkyl$]_2N$—$SO_2$—$(C_1-C_9)$alkyl, $CF_3SO_2$—, $(C_1-C_6)$alkyl-$SO_2$—, phenyl, phenyl$(C_1-C_9)$alkyl, $(C_3-C_{10})$cycloalkyl, $(C_1-C_9)$heterocycloalkyl, and $(C_1-C_9)$heteroaryl.

2. A compound according to claim 1, wherein Z is —$OR^{11}$.

3. A compound according to claim 1, wherein Z is —$NR^{12}R^{13}$.

4. A compound according to claim 1, wherein Q is 4-(($C_6-C_{10}$)aryl($C_1-C_6$)alkoxy)-($C_6-C_{10}$)aryl, 4-(($C_6-C_{10}$)aryl($C_1-C_6$)alkoxy)-($C_2-C_9$)heteroaryl, 4-(($C_2-C_9$)heteroaryl($C_1-C_6$)alkoxy)-($C_6-C_{10}$)aryl, 4-(($C_2-C_9$)heteroaryl($C_1-C_6$)alkoxy)-($C_2-C_9$)heteroaryl, optionally substituted by one or more substituents independently selected from halo, ($C_1-C_6$)alkyl, ($C_1-C_6$)alkoxy or perfluoro($C_1-C_3$)alkyl.

5. A compound according to claim 1, wherein Q is piperidinyl, piperazinyl, pyrrolidino, morpholinyl, thiomorpholinyl, ($C_1-C_6$)alkylpiperidinyl, ($C_6-C_{10}$)arylpiperidinyl, ($C_1-C_9$)heteroaryl piperidinyl, ($C_1-C_6$)alkoxypiperidinyl, 4-(($C_6-C_{10}$)aryloxy)-piperidinyl, 4-(($C_1-C_9$)heteroaryloxy)-piperidinyl, 4-(($C_1-C_{10}$)aryl ($C_1-C_6$)alkoxy)-piperidinyl, 4-(($C_1-C_9$)heteroaryl($C_1-C_6$) alkoxy)-piperidinyl, ($C_1-C_6$)alkyl piperazinyl, 4-($C_6-C_{10}$) aryl-piperazinyl, 4-(($C_1-C_9$)heteroaryl)-piperazinyl optionally substituted by one or more substituents independently selected from halo, ($C_1-C_6$)alkyl, ($C_1-C_6$)alkoxy or perfluoro($C_1-C_3$)alkyl.

6. A compound according to claim 1, wherein Q is 4-(($C_6-C_{10}$)arylmethoxy)-($C_6-C_{10}$)aryl, 4-(($C_6-C_{10}$)arylmethoxy($C_2-C_9$))-heteroaryl, 4-(($C_2-C_9$)heteroarylmethoxy)-($C_6-C_{10}$)aryl or 4-(($C_2-C_9$)heteroarylmethoxy)-($C_2-C_9$)heteroaryl optionally substituted by one or more substituents independently selected from halo, ($C_1-C_6$)alkyl, ($C_1-C_6$)alkoxy or perfluoro($C_1-C_3$)alkyl.

7. A compound according to claim 1, wherein Q is optionally substituted 4-(($C_6-C_{10}$)arylmethoxy)-phenyl, 4-(pyridylmethoxy)-phenyl, 4-(furylmethoxy)-phenyl, 4-(pyroylmethoxy)-phenyl, 4-(thienylmethoxy)-phenyl, 4-(isothiazolylmethoxy)-phenyl, 4-(imidazolylmethoxy)-phenyl, 4-(benzimidazolyl methoxy)-phenyl, 4-(tetrazolylmethoxy)-phenyl, 4-(pyrazinylmethoxy)-phenyl, 4-(pyrimidylmethoxy)-phenyl, 4-(quinolylmethoxy)-phenyl, 4-(isoquinolylmethoxy)-phenyl, 4-(benzofurylmethoxy)-phenyl, 4-(isobenzofurylmethoxy)-phenyl, 4-(benzothienylmethoxy)-phenyl, 4-(pyrazolylmethoxy)-phenyl, 4-(indolylmethoxy)-phenyl, 4-(isoindolylmethoxy)-phenyl, 4-(purinylmethoxy)-phenyl, 4-(carbazolylmethoxy)-phenyl, 4-(isoxazolylmethoxy)-phenyl, 4-(thiazolylmethoxy)-phenyl, 4-(oxazolylmethoxy)-phenyl, 4-(benzthiazolylmethoxy)-phenyl, 4-(benzoxazolylmethoxy)-phenyl.

8. A compound according to claim 1, wherein Q is 4-(($C_6-C_{10}$)arylmethoxy)-($C_6$)aryl optionally substituted by one or more substituents independently selected from halo, ($C_1-C_6$)alkyl, ($C_1-C_6$)alkoxy or perfluoro($C_1-C_3$)alkyl.

9. A compound according to claim 1, wherein Q is para-(($C_6-C_{10}$)arylmethoxy)-($C_2-C_9$)heteroaryl optionally substituted by one or more substituents independently selected from halo, ($C_1-C_6$)alkyl, ($C_1-C_6$)alkoxy or perfluoro($C_1-C_3$)alkyl.

10. A compound according to claim 1, wherein Q is 4-(($C_2-C_9$)heteroarylmethoxy)-($C_6$)aryl optionally substituted by one or more substituents independently selected from halo, ($C_1-C_6$)alkyl, ($C_1-C_6$)alkoxy or perfluoro ($C_1-C_3$)alkyl.

11. A compound according to claim 1, wherein Q is para-(($C_2-C_9$)heteroarylmethoxy)-($C_2-C_9$)heteroaryl optionally substituted by one or more substituents independently selected from halo, ($C_1-C_6$)alkyl, ($C_1-C_6$)alkoxy or perfluoro($C_1-C_3$)alkyl.

12. A compound according to claim 1, wherein $R^1$, $R^2$, $R^5$ and $R^6$ are each independently selected from the group consisting of hydrogen, ($C_1-C_6$)alkyl, ($C_2-C_6$)alkenyl, perfluoro($C_1-C_6$)alkyl, ($C_1-C_6$)alkyl(C=O)—, ($C_1-C_6$)alkoxy-(C=O)—, ($C_1-C_6$)alkyl-NH—(C=O)—, and [($C_1-C_6$)alkyl]$_2$-N—(C=O)—; wherein each of said ($C_1-C_6$)alkyl groups are each independently optionally substituted by one to two groups selected from halo, trifluoromethyl, hydroxy, amino, ($C_1-C_6$)alkoxy, ($C_6-C_{10}$)aryl, ($C_1-C_9$)heteroaryl, ($C_3-C_6$)cycloalkyl, ($C_3-C_9$)heterocyclic, ($C_1-C_6$)alkyl-(C=O)—NH—, ($C_1-C_6$)alkyl-(C=O)—O—, ($C_1-C_6$)alkylamino or (($C_1-C_6$)alkyl)$_2$ amino.

13. A compound according to claim 1, wherein $R^7$ and $R^8$ are each independently selected from the group consisting of hydrogen, hydroxy, halo, $(C_1-C_9)$alkyl, $(C_2-C_6)$alkenyl, amino, $(C_1-C_6)$alkylamino, $[(C_1-C_6)alkyl]_2$amino, $(C_1-C_6)$alkoxy, perfluoro$(C_1-C_6)$alkyl and perfluoro$(C_1-C_6)$alkoxy.

14. A compound according to claim 1, wherein one of $R^1$ and $R^2$, $R^5$ and $R^6$ or $R^7$ and $R^8$ is taken together to form a carbonyl group.

15. A compound according to claim 1, wherein one of $R^1$ and $R^2$, $R^5$ and $R^6$ or $R^7$ and $R^8$ is taken together to form an optionally substituted $(C_3-C_6)$cycloalkyl ring.

16. A compound according to claim 1, wherein one of $R^5$ and $R^7$, $R^5$ and $R^8$, $R^6$ and $R^7$ or $R^6$ and $R^8$ is taken together to form an optionally substituted $(C_4)$cycloalkyl ring.

17. A compound according to claim 1, wherein $R^1$ or $R^2$ are hydrogen.

18. A compound according to claim 1, wherein at least one of $R^1$ or $R^2$ is other than hydrogen.

19. A compound according to claim 1, wherein at least one of $R^1-R^6$ is hydrogen or $(C_1-C_6)$alkyl.

20. A compound according to claim 1, wherein $R^1$ and $R^2$ are each hydrogen or $(C_1-C_6)$alkyl.

21. A compound according to claim 1, wherein $R^1-R^8$ are all each hydrogen.

22. A compound according to claim 1, wherein said compound is selected from the group consisting of:

4-[4-(4-Fluoro-2-methyl-benzyloxy)-benzenesulfonyl]-3-hydroxy-tetrahydro-pyran-3-carboxylic acid hydroxyamide;

4-[4-(3-Chloro-benzyloxy)-benzenesulfonyl]-3-hydroxy-tetrahydro-pyran-3-carboxylic acid hydroxyamide;

4-[4-(4-Chloro-benzyloxy)-benzenesulfonyl]-3-hydroxy-tetrahydro-pyran-3-carboxylic acid hydroxyamide;

4-[4-(2-Chloro-benzyloxy)-benzenesulfonyl]-3-hydroxy-tetrahydro-pyran-3-carboxylic acid hydroxyamide;

4-[4-(3-Fluoro-benzyloxy)-benzenesulfonyl]-3-hydroxy-tetrahydro-pyran-3-carboxylic acid hydroxyamide;

3-Hydroxy-4-[4-(2-methyl-benzyloxy)-benzenesulfonyl]-tetrahydro-pyran-3-carboxylic acid hydroxyamide; and 4-[4-(4-Fluoro-2-methyl-benzyloxy)-benzenesulfonyl]-3-hydroxy-tetrahydro-pyran-3-carboxylic acid hydroxyamide.

23. A pharmaceutical composition for the treatment of a condition which can be treated by the inhibition of a matrix metalloproteinase in a mammal, comprising an amount of a compound of claim 1 effective in such treatment and a pharmaceutically acceptable carrier.

24. A pharmaceutical composition for the treatment of a condition which can be treated by the inhibition of a mammalian reprolysin in a mammal, comprising an amount of a compound of claim 1 effective in such treatment and a pharmaceutically acceptable carrier.

25. A pharmaceutical composition for the treatment of arthritis, inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis, aortic aneurysm, congestive heart failure, myocardial infarction, stroke, cerebral ischemia, head trauma, spinal cord injury, neuro-degenerative disorders, autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, comprising an amount of a compound of claim 1 or a pharmaceutically acceptable salt thereof, effective in such treatments or inhibition and a pharmaceutically acceptable carrier.

26. A method for the treatment of a condition which can be treated by the inhibition of a matrix metalloproteinase in a mammal, comprising administering to said mammal an amount of a compound of claim 1, effective in treating such a condition.

27. A method for the treatment of a condition which can be treated by the inhibition of a mammalian reprolysin in a mammal, comprising administering to said mammal an amount of a compound of claim 1, effective in treating such a condition.

28. A method for treating a condition selected from the group consisting of arthritis, inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis, aortic aneurysm, congestive heart failure, myocardial infarction, stroke, cerebral ischemia, head trauma, spinal cord injury, neuro-degenerative disorders, autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scieritis, AIDS, sepsis and septic shock in a mammal, comprising administering to said mammal an amount of a compound of claim 1, effective in treating such a condition.

* * * * *